US006326201B1

(12) United States Patent
Fung et al.

(10) Patent No.: US 6,326,201 B1
(45) Date of Patent: Dec. 4, 2001

(54) PANCREATIC PROGENITOR CELLS, METHODS AND USES RELATED THERETO

(75) Inventors: Brenda Fung; Kevin Pang, both of Belmont; David Kagan, Brighton, all of MA (US)

(73) Assignee: Curis, Inc., Cambridge, MA (US)

( * ) Notice: Subject to any disclaimer, the term of this patent is extended or adjusted under 35 U.S.C. 154(b) by 0 days.

(21) Appl. No.: 09/499,362

(22) Filed: Feb. 10, 2000

Related U.S. Application Data

(60) Provisional application No. 60/171,338, filed on Dec. 21, 1999, provisional application No. 60/142,305, filed on Jul. 2, 1999, and provisional application No. 60/119,576, filed on Feb. 10, 1999.

(51) Int. Cl.[7] .............................. C12N 5/02; C12N 5/00; C12N 5/08
(52) U.S. Cl. ......................... 435/377; 435/325; 435/371; 435/378
(58) Field of Search .................................... 435/325, 366, 435/375, 378, 379, 381, 377, 371

(56) References Cited

U.S. PATENT DOCUMENTS

| | | | | |
|---|---|---|---|---|
| 5,888,705 | * | 3/1999 | Rubin et al. | 435/366 |
| 6,001,647 | * | 12/1999 | Peck et al. | 435/325 |

OTHER PUBLICATIONS

Song et al. Gastroenterology 117:1416–1426 1999.*

* cited by examiner

*Primary Examiner*—Robert A. Schwartzman
*Assistant Examiner*—Katharine F Davis
(74) *Attorney, Agent, or Firm*—Matthew P. Vincent; David P. Halstead; Ropes & Gray

(57) ABSTRACT

The present invention relates to a substantially pure population of viable pancreatic progenitor cells, and methods for isolating such cells. The present invention further concerns certain therapeutic uses for such progenitor cells, and their progeny.

39 Claims, 44 Drawing Sheets

|  | E13 | | E14 | | | E15 | | | E16 | | |
|---|---|---|---|---|---|---|---|---|---|---|---|
|  | #6 | #7 | #11 | #4 | #8 | #14 | #7 | #8 | #14 | #23 | #24 | #30 |
| INSULIN | - | - | + | + | + | - | + | + | - | + | + | - |
| PDX-1 | + | + | - | + | - | - | + | - | - | - | - | - |
| GLUCAGON | ± | + | ± | + | ± | - | - | - | - | - | - | - |
| AMYLASE | + | ± | ± | + | + | ± | + | + | + | ± | + | + |
| ACTIN | + | + | + | + | + | + | + | + | + | + | + | + |
| CYCLOPHILIN | + | + | + | + | + | + | + | + | + | + | + | - |

Fig. 21

|   | 1 | 2 | 3 | 4 | 5 | 6 | 7 | 8 | 9 | 10 | 11 | 12 |
|---|---|---|---|---|---|---|---|---|---|----|----|----|
| A | actin | HexoK | PYY | TyrH | SHH | Wnt3 | delta | IGF1 | TNFR2 | PICK1 | amphy2 | Rho-GDI |
| B | G3PDH | SubPR | NPY | Rab3A | Patch-1 | Wnt5 | Jagged | PKA | Pw1 | PCTA-RE1 | OSF-1 | Sez-12 |
| C | G6PDH | insulin | NPYR | activin | SMO | frizzled | DLK | Is1-1 | HNF1α | Gli | GP106 | SelenoP |
| D | RPs6 | glucagon | Secretin | follistatin | TGFβ1 | sFRP-1 | notch1 | beta2 | DCoH | P48 | HCNGP | Surf-1 |
| E | Glut4 | SomS | nestin | activinR | TGFβ2 | EGF | notch2 | PDX1 | HNF3β | ID-1 | clusterin | VASP |
| F | albumin | PP | ChromograninA | BMB4 | TGFβR1 | EGFR | FGF6 | Pax4 | HNF4α | IDR | Cab45b | UK-2 |
| G | amylase | IAPP | GLP-1R | BMB4R | PTHrP | SCF | FGF9 | Pax6 | Nkx2.2 | MITF | HBP | UK-4 |
| H | CarbP | Glut2 | CK19 | BMB6 | PTHR | c-Kit | FGFR1 | COUP-TFII | Nkx6.1 | SUG1 | RP2 | UK-6 |

Fig. 22

| GENE NAME | ISLET/E15 INS+ | ISLET/Bb INS+ |
|---|---|---|
| Secretin | 16 | 8 |
| insulin | 13 | 4 |
| glucagon | 3 | 2 |
| IGF1 | 6 | 6 |
| nestin | 5 | 3 |
| Rab3A | 5 | 2 |
| Glut2 | 2 | 1.3 |
| ChromograninA | 4 | 3 |
| PDX1 | 3 | 2 |
| Isl-1 | 2 | 2 |
| EGF | 4 | 2 |
| NPYR | 4 | 1.3 |
| TGFb1 | 4 | 3 |
| TGFbR1 | 6 | 2 |
| delta | 26 | 18 |
| DLK | 3 | 4 |
| Wnt3 | 3 | 2 |
| Gli | 2 | 2 |
| SMO | 4 | 6 |
| COUP-TFII | 0.9 | 1.1 |

Fig. 29

PANCREATIC PROGENITOR CELLS, METHODS AND USES RELATED THERETO

RELATED APPLICATIONS

This application claims priority to U.S. Provisional Applications: U.S. Ser. No. 60/119,576 filed Feb. 10, 1999; U.S. Ser. No. 60/142,305 filed Jul. 2, 1999; and U.S. Ser. No. 60/171,338 filed Dec. 21, 1999. The specifications of which are incorporated by reference herein.

BACKGROUND OF THE INVENTION

Insulin-dependent diabetes mellitus (IDDM) is a disease characterized by elevated blood glucose and the absence of the hormone insulin. The cause of the raised sugar levels is insufficient secretion of the hormone insulin by the pancreas. In the absence of this hormone, the body's cells are not able to absorb sugar from the blood stream in normal fashion, and the excess sugar accumulates in the blood. Chronically elevated blood glucose damages tissues and organs. IDDM is treated with insulin injections. The size and timing of insulin injections are influenced by measurements of blood sugar.

There are over 400 million diabetics in the world today. For instance, diabetes is one of the most prevalent chronic diseases in the United States, and a leading cause of death. Estimates based on the 1993 National Health Interview Survey (NHIS) indicate that diabetes has been diagnosed in 1% of the U.S. population age <45 years, 6.2% of those age 45–64 years, and 10.4% of those age >65 years. In other terms, in 1993 an estimated 7.8 million persons in the United States were reported to have this chronic condition. In addition, based on the annual incidence rates for diabetes, it is estimated that about 625,000 new cases of diabetes are diagnosed each year, including 595,000 cases of non-insulin-dependent diabetes mellitus (NIDDM) and 30,000 cases of insulin-dependent diabetes mellitus (IDDM).

The total cost of diabetes in the United States has been estimated at $92 billion annually, including expenditures on medical products, hospitalization and the value of lost work. Substantial costs to both society and its citizens are incurred not only for direct costs of medical care for diabetes, but also for indirect costs, including lost productivity resulting from diabetes-related morbidity and premature mortality. Persons with diabetes are at risk for major complications, including diabetic ketoacidosis, end-stage renal disease, diabetic retinopathy and amputation. There are also a host of less directly related conditions, such as hypertension, heart disease, peripheral vascular disease and infections, for which persons with diabetes are at substantially increased risk.

While medications such as injectable insulin and oral hypoglycemics allow diabetics to live longer, diabetes remains the third major killer, after heart disease and cancer. Diabetes is also a very disabling disease, because medications do not control blood sugar levels well enough to prevent swinging between high and low blood sugar levels, with resulting damage to the kidneys, eyes, and blood vessels.

Studies have documented that medical costs for persons with diabetes are higher because they visit physician's offices, hospital outpatient departments, and emergency rooms more frequently than their nondiabetic counterparts, and are more likely to be admitted to the hospital. Americans with diabetes have two to five times higher per capita total medical expenditures and per capita out-of-pocket expenses than people without diabetes. These expenses and their associated loss of productivity have impact not only on diabetic patients and their families, but on federal and state governments and society as a whole.

Data from the Diabetes Control and Complications Trial (DCCT) show that intensive control of blood glucose significantly delays complications of diabetes, such as retinopathy, nephropathy, and neuropathy, compared with conventional therapy consisting of one or two insulin injections per day. Intensive therapy in the DCCT included multiple injection of insulin three or more times per day or continuous subcutaneous insulin infusion (CSII) by external pump. Insulin pumps are one of a variety of alternative approaches to subcutaneous multiple daily injections (MDI) for approximating physiological replacement of insulin.

Replenishment of functional glucose-sensing, insulin-secreting pancreatic beta cells through islet transplantation has been a longstanding therapeutic target. The limiting factor in this approach is the availability of an islet source that is safe, reproducible, and abundant. Current methodologies use either cadaverous material or porcine islets as transplant substrates (Korbutt et al., 1997). However, significant problems to overcome are the low availability of donor tissue, the variability and low yield of islets obtained via dissociation, and the enzymatic and physical damage that may occur as a result of the isolation process (reviewed by Secchi et al., 1997; Sutherland et al., 1998). In addition are issues of immune rejection and current concerns with xenotransplantation using porcine islets (reviewed by Weir & Bonner-Weir, 1997).

It is an object of the present invention to create functional beta cells in vitro by expansion and differentiation of a pancreatic stem/progenitor cell. Advantages lie in obviating the need for physical dissociation of tissue in order to obtain islets, and the potential for greater reproducibility and control of the process. Successful achievement requires the differentiation and maturation of glucose-sensing, insulin-secreting beta cells from an expandable precursor population.

SUMMARY OF THE INVENTION

The present invention relates to substantially pure preparations of viable pancreatic progenitor cells, and methods for isolating such cells from pancreatic ductal tissues, notably intralobular ductal tissue. The present invention further concerns certain uses for such progenitor cells, and their progeny.

In general, the invention features a cellular composition including, as the cellular component, a substantially pure population of viable pancreatic progenitor cells which progenitor cells are capable of proliferation in a culture medium. In a preferred embodiment, the cellular composition has fewer than about 20%, more preferably fewer than about 10%, most preferably fewer than about 5% of lineage committed cells.

In one embodiment, the progenitor cells of the present invention are characterized by an ability for self-regeneration in a culture medium and differentiation to pancreatic lineages. In a preferred embodiment, the progenitor cells are inducible to differentiate into pancreatic islet cells, e.g., $\beta$ islet cells, $\alpha$ islet cells, $\delta$ islet cells, or $\phi$ islet cells. Such pancreatic progenitor cells may be characterized in certain circumstances by the expression of one or more of: homeodomain type transcription factors such as STF-1; PAX gene(s) such as PAX6; PTF-1; hXBP-1; HNF genes(s); villin; tyrosine hydroxylase; insulin; glucagon; and/or neuropeptide Y. The pancreatic progenitor cells of the present invention may also be characterized by binding to lectin(s), and preferably to a plant lectin, and more preferably to peanut agglutinin. In certain preferred embodiments, the progenitor cells are PDX1+, e.g., by FACS sorting, and capable of differentiation into glucose-responsive insulin secreting cells.

In certain preferred embodiments, the progenitor cells are PDX1+ and Glut2+. In certain preferred embodiments, the progenitor cells are PDX1$^+$, Glut2$^+$ and stain with PNA.

In certain preferred embodiments, the subject pancreatic progenitor cells will have one or more of the following characteristics: (i) able to grow in 2–5 percent fetal calf serum; (ii) able to grow on plastic, e.g., no need to use matrigel; (iii) no statistically significant induction of cells to proliferate or differentiate when treated with TGFβ5 (GenBank accession P16176) at concenrates up to 30 pg/ml.

In yet another embodiment, the invention features a pharmaceutical composition including as the cellular component, a substantially pure population of viable pancreatic progenitor cells, which progenitor cells are capable of proliferation in a culture medium.

In general, the preferred progenitor cells will be of mammalian origin, e.g., cells isolated from a primate such as a human, from a miniature swine, or from a transgenic mammal, or are the cell culture progeny of such cells. In one embodiment, pancreatic ductal tissue is isolated from a patient and subjected to the present method in order to provide a resulting culture of pancreatic progenitor cells (or differentiated cells derived therefrom). Gene replacement or other gene therapy is carried out ex vivo, and the isolated cells are transplanted back into the initial donor patient or into a second host patient.

In another aspect, the invention features a cellular composition comprising, as a cellular population, at least 75% (though more preferably at least 80, 90 or 95%) progenitor cells and capable of self-regeneration in a culture medium.

In yet another aspect, the invention features a cellular composition consisting essentially of, as the cellular population, viable pancreatic progenitor cells capable of self-regeneration in a culture medium and differentiation to pancreatic lineages. For instance, in certain embodiments the progenitor cells are isolated from pancreatic intralobular duct explants, e.g. isolated by biopsy, or are the cell culture progeny of such cells.

One aspect of the invention features a method for isolating pancreatic progenitor cells from a sample of pancreatic duct. In general, the method provides for a culture system that allows reproducible expansion of pancreatic ductal epithelium while maintaining "stemmedness" and the ability to differentiate into endocrine and exocrine cells. As illustrated below, in a preferred embodiment, pancreatic ductal epithelium is obtained, e.g., by explant or enzymatic digestion, and cultured to confluence. The confluent cell population is contacted with an agent, e.g., a trophic agent such as a growth factor, which causes differentiation of progenitor cells in the cultured population. Subsequently, progenitor cells from the explant that proliferate in response to the agent are isolated, such as by direct mechanical separation of newly emerging buds from the rest of the explant or by dissolution of all or a portion of the explant and subsequent isolation of the progenitor cell population.

In certain embodiments, the culture is contacted with a cAMP elevating agents, such as 8-(4-chlorophenylthio)-adenosine-3':5'-cyclic-monophosphate (CPT-cAMP) (see, for example, Koike *Prog. Neuro-Psychopharmacol. and Biol. Psychiat.* 16 95–106 (1992)), CPT-cAMP, forskolin, Na-Butyrate, isobutyl methylxanthine (IBMX) and cholera toxin (see Martin et al. *J. Neurobiol.* 23 1205–1220 (1992)) and 8-bromo-cAMP, dibutyryl-cAMP and dioctanoyl-cAMP (e.g., see Rydel et al. *PNAS* 85:1257 (1988)).

In certain embodiments, the culture is contacted with a growth factor, e.g., a mitogenic growth factor, e.g., the growth factor is selected from a group consisting of IGF, TGF, FGF, EGF, HGF, hedgehog or VEGF. In other embodiments, the growth factor is a member of the TGFβ superfamily, preferably of the DVR (dpp and vg1 related) family, e.g., BMP2 and/or BMP7.

In certain embodiments, the culture is contacted with a steroid or corticosteroid such as, for example, hydrocortisone, deoxyhydrocortisone, fludrocortisone, prednisolone, methylprednisolone, prednisone, triamcinolone, dexamethasone, betamethasone and paramethasone. See, generally, The Merck Manual of Diagnosis and Therapy, 15th Ed., pp. 1239–1267 and 2497–2506, Berkow et al., eds., Rahay, N.J., 1987).

In a preferred embodiment, the cultures are contacted with a cAMP elevating agent, a growth factor and a steroid or corticosteroid, e.g., with the DCE cocktail described herein.

In another aspect, the invention features, a method for screening a compound for ability to modulate one of growth, proliferation, and/or differentiation of progenitor cells obtained by the subject method, including: (i) establishing an isolated population of pancreatic progenitor cells; (ii) contacting the population of cells with a test compound; and (iii) detecting one of growth, proliferation, and/or differentiation of the progenitor cells in the population, wherein a statistically significant change in the extent of one of growth, proliferation, and/or differentiation in the presence of the test compound relative to the extent of one of growth, proliferation, and/or differentiation in the absence of the test compound indicates the ability of the test compound to modulate one of the growth, proliferation, and/or differentiation.

In another aspect, the invention features, a method for treating a disorder characterized by insufficient insulin activity, in a subject, including introducing into the subject a pharmaceutical composition including pancreatic progenitor cells derived by the subject method, or differentiated cells arising therefrom, and a pharmaceutically acceptable carrier. In preferred embodiments, the progenitor cells are derived from a donor source (which may also be the transplant patient), and expanded at least order of magnitude prior to implantation. As shown in FIG. 40, the subject cellular compositions can be used to rescue diabetic mice.

In a preferred embodiment the subject is a mammal, e.g., a primate, e.g, a human.

In another preferred embodiment the disorder is an insulin dependent diabetes, e.g, type I diabetes.

In yet another embodiment, the pancreatic progenitor cells are induced to differentiate into pancreatic islet cells, e.g., β islet cells, α islet cells, δ islet cells, or φ islet cells, subsequent to being introduced into the subject.

In other embodiments, the pancreatic progenitors cells are induced to differentiate into pancreatic islet, e.g., β islet cells, α islet cells, δ islet cells, or φ islet cells, in culture prior to introduction into the subject.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors* For *Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following detailed description, and from the claims.

DETAILED DESCRITION OF THE DRAWINGS

FIG. 1. Isolation of pancreatic ducts. The cartoon illustrates the process by which the ducts under study were obtained. Pancreatic tissue from 2–3 week old rats was dissociated in collagenase solution and ductal material was obtained by handpicking. Clean ducts were placed in culture on plastic. Within 3–5 days a monolayer was obtained, from which NACs were produced upon exposure to an inductive medium. Shown below the cartoon is a series of photographs showing the various stages of duct isolation and purity. The first panel shows the primary digest, and the second panel shows the result of the first round of handpicking. Note that there is still some contaminating exocrine tissue. After the second round of selection, the ducts are free of both islet and exocrine tissue.

FIG. 2. Culture and insulin staining of pancreatic ducts. Depicted is a time series of single ducts in culture from time zero plating (T0) to day five (T5) in culture. The upper panel shows examples of Cy3-labelled immunocytochemical staining for insulin, and the lower panel shows the combined brightfield and fluorescence images. At T0 there are no insulin-expressing cells. Within 24 hours of culture, the duct begins to distend and disintegrate, with cells moving toward the periphery. Proliferating cells are present primarily in the outgrowing monolayer of mesenchymal cells, although ductal epithelial cells do also incorporate BrdU (not shown). Insulin-positive cells emerged spontaneously from the duct over time in culture, but their overall replication rate is slow (not shown). By T5 some monolayers contained sizable clusters of insulin-positive cells; typically these contained 20 cells or less.

FIGS. 3A–3G. The duct monolayer expresses multiple progenitor cell markers. Monolayers were stained for both insulin (A) and amylase (B). Panel C is a composite showing that some cells express both insulin and amylase. Two morphologically distinct cell types are present, those that are adherent and flat, and cells that are semi-adherent and round. Arrowheads denote* rounded semi-adherent cells that may coexpress both insulin and amylase. Panels D and E show staining for glucagon and PYY, respectively, and Panel F is a composite showing that one of the glucagon-bright cells also expresses PYY. Panel G shows a composite of nuclear PDX-1 (Cy3) and cytoplasmic insulin (FITC) staining. Arrowheads indicate cells that express PDX-1 but not insulin or vice versa.

FIGS. 4A–4D. Factor addition influences the appearance of the nonadherent cell (NAC) type. Hoffmnan modulation contrast photographs were taken of cultures treated with various factors. Cultures were grown in 5% FBS for five days until a confluent monolayer was obtained; factors were then added for an additional 48 hours and the cultures were photographed. NACs were observed in all conditions. Panel A shows the control culture grown in FBS; panel B, culture treated with DCE (1 $\mu$M Dexamethasone, 100 ng/ml Cholera toxin, 10 ng/ml EGF); Panel C, HGF (10 ng/ml), and Panel D, TGFP$\beta$1 (10 ng/ml). Arrow 1 in Panel A indicates the adherent and confluent monolayer and the Arrow 2 points to a pair of rounded loosely or non-adherent cells. The HGF and TGF$\beta$1 treated cultures also contained semi- and non-adherent cells. However, the pharmacological cocktail DCE induced, on average, at least 8-fold more NACs than all other conditions tried. BrdU pulsing experiments showed strong proliferation and a confluent monolayer even after 48 hours of DCE exposure, indicating perhaps asymmetric division as opposed to simple loss of cell adherence. The inset in Panel B illustrates the morphology and granularity of NACs.

FIGS. 5A–5G. Multiple hormone-containing cell types are detected in the NAC population. NACs were collected from DCE-stimulated monolayer cultures and analyzed immunocytochemically for endocrine marker expression. Cells expressing insulin (A, C), PDX-1 (D), glucagon (E), somatostatin (F), and pancreatic polypeptide (G) were all present in the NAC population. Markers were visualized with FITC or Cy3 immunofluorescence and the nuclei counterstained with DAPI (C–G). Panel A shows a 10× objective field magnification of insulin staining. Heterogeneous signal strength was observed; shown here are one brightly stained cell and many dimly stained cells along with negative cells. Panel B shows staining with normal preimmune serum. Note that the dim cells in A are significantly above background, yet contain much less insulin than the bright cell observed. Panel C shows higher magnification (20× objective) of another insulin staining (Cy3) showing dim and negative cells. In this field and others approximately 40–50% of the cells test insulin-positive. Panels D, E, F, and G show PDX-1, glucagon, somatostatin and pancreatic polypeptide staining, respectively (60× objective). Arrows indicate DAPI-stained, hormone-negative cells.

FIGS. 6A–6D. Single cell PCR (SC-PCR) analysis of PDX-1, insulin and glucagon expression in NACs. Forty cells were selected from a random population of NACs and processed for cDNA as described in the Methods section. These cDNAs were then analyzed for insulin (B), glucagon (C), and PDX-1 (D) message. Panel A shows the ethidium bromide staining of the cDNA on a 1.2% agarose gel. The bulk of cDNA product fell within the targeted 500–1000 bp range. Panel B shows that there is variation in the amount of insulin message per cell, with some cells giving much stronger signal than others. $15/40$ (37%) of the cells tested positive for insulin mRNA. Of these, one was also positive for glucagon, and both messages were relatively weak compared to the other cells that expressed insulin only. Panel C shows that $2/40$ (5%) of the cells contained glucagon message, a result that correlates well with the immunocytochemistry data. Panel D shows that many of the picked cells contained PDX-1 mRNA. Note that a significant fraction of cells express PDX-1 mRNA only, with no insulin or glucagon.

FIG. 7. Insulin content and glucose response of cultured ducts. Freshly isolated ducts (T=0), ducts cultured for one week (T=7), and NACs harvested from the DCE-induced duct culture were all tested for glucose-stimulated insulin secretion (GSIS) and also extracted for total insulin content. The time zero ducts contained no detectable insulin by RIA. In contrast, the cultured ducts did have a discernible increase in insulin content, but no glucose response. In this representative experiment, the isolated NACs showed an insulin content that was 18-fold greater than the DCE-treated monolayer when normalized to a per cell level. In addition, the NACs demonstrated a strong 3-fold GSIS response, well within the 3–5 fold physiological range observed with adult islets. ML=monolayer, n.d.=not detectable.

FIGS. 8A–8B. Glucose-induced calcium currents in NACs. Glucose induces an inward calcium current in the NAC population. Changes in intracellular calcium at the single cell level were monitored using Fluo-3 and confocal microscopy. A, In this representative experiment (n>10) approximately one-third of the population initiated a robust calcium influx in response to glucose administration, and 58% of the cells showed no response to glucose. In every experiment, approximately 6–10% of the cells begin with a high intracellular calcium content that decreases with time; these were judged to be dying cells. 80 cells were analyzed in this experiment. B, The reversibility of the induced calcium current is demonstrated. In this representative experiment (n>6), the glucose-stimulated calcium current could be washed out with Krebs Ringer Phosphate (KRP) solution. A second calcium current could then be stimulated by readministration of 17 mM glucose. Washout of the glucose followed by tolbutamide stimulation, a SUR-linked potassium channel blocker, also stimulated a calcium current, as expected. Arrows indicate times of administration. A total of 123 cells were analyzed in this experiment. 7–13% of the cells gave rise to calcium currents in response to the stimulus (shown in red) whereas 45–65% of the cells showed no response to any of the stimuli (shown in blue). The remaining 35% of cells exhibited varying amplitudes and kinetics in response to challenge, indicating a complex population.

FIG. 9. Graph showing induction of differentiation by DCE

FIG. 10. Graph showing effect of Forskolin, Dibutyrl cAMP and Na-Butyrate on induction of differentiation.

FIGS. 11 and 12. Graphs illustrating the effect of secretin on induction of floating progenitor cells.

FIG. 13. Graph demonstrates that Vasoactive Intestinal Peptide (VIP) also differentiates duct monolayers by inducing the appearance of floating progenitor cells.

FIG. 14. Graph showing that insulin diminishes secretin-induced differentiation.

FIGS. 15–17. Micrographs that illustate the phenotype of cells which have been cultured for two weeks after being sorted on the basis of PNA staining.

FIGS. 18 and 19. Micrographs that illustrate the specificity of PNA in adult and embryonic pancreas.

FIG. 20. Electrophoretic gel showing the results of typical single cell mRNA PCR amplification reactions.

FIG. 21. Table illustrating the changes in the gene expression during pancreatic development.

FIG. 22. Chart illustrating one embodiment of an array of markers for detecting beta cells and precursors thereof.

FIG. 23. Autoradiographs profiling gene expression in adult and embryonic pancreatic tissue, and heart.

FIG. 24. Graph demonstating how quantatitve analysis of gene expression can be carried out as part of a determination of the gene expression profile of a cell.

FIG. 25. Autoradiographs profiling gene expression in embryonic pancreatic tissue at different stages and after different stimulus.

FIG. 26. Graphs illustating the quantatitve analysis of the autoradiagraphs.

FIG. 27. Autoradiographs profiling gene expression in the so-called floating progenitor cells.

FIG. 28. Graph illustating the quantatitve analysis of the autoradiagraphs of FIG. 27.

FIG. 29. Table showing the relative levels of expression of certain genes between adult islets and during pancreatis development.

FIGS. 30–31. Micrographs that illustrate the binding of certain lectins to adult rat pancreas.

FIGS. 32–39. Micrographs that illustrate the binding of certain lectins to adult human pancreas.

FIG. 40. Implanted cells from a pancreatic duct-derived culture transiently rescues the diabetic state. A heterogeneous population containing functional beta cells derived from the non-adherent portion of a differentiated pancreatic duct monolayer was implanted into streptozotocin (STZ)-treated diabetic mice. SCID mice injected with STZ became diabetic within 48 hours. Insulin containing pellets were then implanted subcutaneously to stabilize the blood glucose and create a more stable environment for cell implantation. The insulin pellet was designed to expire 7 days post-implantation at T=11 days (T11). Within 48 hours of pellet implant the fasting blood glucose of these animals were reduced from a range of 280–380 mg/dl blood glucose to less than 50 mg/dl. In test groups either cells or adult islets as positive control were then implanted under the renal capsule. One week later (T13) fasting blood glucose was measured and again at days 16, 21, and 28. Black squares represent placebo group (n=5 mice) and as expected, in the absence of insulin, the blood glucose slowly climbed over time to well over 300 mg/dl. Animals (n=5) implanted with insulin pellets only and no cell implants also performed as expected, with a transient rescue followed by diabetic rebound after the insulin release tablet had expired (red diamonds). Animals receiving islets (blue triangles, n=5, 400 islets per animal) showed perfect long term rescue with fasting blood glucose being maintained at approximately 100 mg/dl. The single surviving animal receiving duct-derived cells (green circles, n=1 of 7) showed a transient rescue of the diabetic state. The single animal demonstrated a 4–5 day lowering of >150 mg/dl blood glucose before rebounding to pre-implant blood glucose levels.

DETAILED DESCRIPTION OF THE INVENTION

(i) Overview

The existence within the adult pancreas of a progenitor cell that is capable of giving rise to the endocrine islet was proposed long ago (e.g., Bensley, 1911). A number of regeneration models provide early in vivo evidence for islet neogenesis in the adult organ (Shaw and Latimer, 1925, Waren and Root 1925). Histological studies indicated a physical attachment between what was assumed to be newly forming islets and the ductal network. From these and more recent work (Bonner-Weir et al. 1993; Gu et al. 1994; Fernandes et al. 1997) developed the now widely held belief that islet progenitor cells derive from a subpopulation of the pancreatic duct epithelium.

The ductal network is one of three functional components of the adult pancreas (the other two being the exocrine acini and the endocrine islets), and is responsible for fluid secretion and delivery of digestive enzymes into the small intestine. Estimates of pancreatic ductal mass in the rat average 11%. The exocrine acini, which produce the digestive enzymes, make up by far the greatest portion of the adult pancreas, accounting for approximately 77–89% of overall tissue mass. The islets contain the insulin-secreting beta cells and are responsible for hormonal regulation of glucose metabolism; they comprise less than 5% of total organ mass (reviewed by Githens, 1988).

Pancreatic regeneration models such as 90% pancreatectomy (Bonner-Weir et al. 1993, Lampeter et al, 1995), duct ligation (Wang et al. 1995, Rosenberg 1995), and transgenic mice (Gu and Sarvetnick, 1993), all provide further in vivo evidence that islet tissue arises de novo from duct-associated pancreatic progenitor cells. A common observation in each of these injury models is the rapid appearance of endocrine cells in the proliferating ductal epithelium after experimental insult, and the subsequent appearance over the course of weeks of presumably newly formed islets in the periductular space. In addition, cells that appear to express both insulin and amylase, which mark endocrine and exocrine cells, respectively, have been observed during the regenerative process and it is thought that these cells might represent activated progenitor cells (Melmed, 1979; Cossel, 1984; Gu et al. 1994). The exact origin of these activated cells, whether ductal, acinar, or otherwise, and the mechanism of their activation, from progenitor cells or through selective dedifferentiation, remains to be determined. Despite these uncertainties, these studies underscore the potential islet neogenic capacity of the mature pancreas.

It has been proposed that during pancreatic development, early expression of PDX-1, a transcription factor that regulates expression of insulin and other beta cell components marks progenitor cells capable of giving rise to both the exocrine and endocrine compartments ((Ohlsson et al. 1993; Offield et al. 1996; Ahlgren et al. 1996, and reviewed by Madsen et al. 1996 and Edlund, 1998). Developmental mechanisms may also play a role in adult beta cell neogenesis. Indeed, Fernandes et al. (1997) describe the appearance of PDX-1 expressing cells in adult pancreatic ducts after streptozotocin insult. Another embryonic product is the hormone PYY, whose expression is also postulated to mark committed endocrine progenitor cells (Upchurch et al. 1994). Both of these cell types are found in islets as well as early in pancreatic development, and it is not yet clear if they contribute directly to islet formation. However they provide early markers against which regenerative systems can be analyzed.

Long-term in vitro culture of purified adult pancreatic duct epithelium has been largely unsuccessful. The work of Githens and his colleagues represents the best attempt to date (Githens et al. 1989; Githens et al. 1987). Their approach was to purify the ductal epithelium away from stromal components during culture, and the results demonstrated that the enriched epithelial fraction could maintain normal epithelial cell secretory function for a limited time (approximately 1 week) in culture. In addition these cells could express specific pancreatic epithelial markers. However, long term cultures were not possible and the authors did not report on any observed increase in the formation of endocrine cell types.

Using a different approach, we chose to culture isolated pancreatic ducts in their entirety, reasoning that the duct fragment inclusive of its component epithelium and mesenchyme would be the basic biological unit that contains endocrine progenitor cell activity. The dependence of pancreatic epithelium on its surrounding mesenchyme for survival and growth during development was first demonstrated by the early work of Goloslow and Grobstein (1962) and others (Wessels and Cohen, 1967). More recent work using gene knockout technology demonstrated that the loss of dorsal pancreatic mesenchyme correlated with the loss of the developing pancreatic epithelium (Ahlgren, et al. 1997) and consequently the absence of pancreas formation from the dorsal bud. Respecification of pancreatic mesenchyme identity to smooth muscle by sonic hedgehog protein also resulted in deranged pancreatic epithelial outgrowth (Apelqvist et al. 1997). From these results in the developing pancreas, it was hypothesized that the relationship between mesenchyme and epithelium may continue to be functionally important in the adult pancreas, particularly with respect to islet neogenesis and regrowth.

Freshly isolated duct fragments are comprised of a single epithelial layer surrounded by mesenchymal stroma and contain few, if any, differentiated endocrine cells. After the ducts are grown in culture, we observed the presence of multiple endocrine cell types and also potential progenitor cells coexpressing markers such as insulin and amylase, which might contribute to the formation of differentiated beta cells. In addition, we observed the emergence of a nonadherent cell type previously undescribed in pancreatic cell culture. The number and properties of this novel cell type are affected by the addition of various factors, one combination of which reproducibly leads to the formation of functional, glucose-responsive beta-like cells. Our data thus suggest the presence and induction of pancreatic progenitor cell activities in this duct culture system, which now makes possible the in vitro study of beta cell neogenesis and also provides a first step in the process of producing beta cells for the treatment of insulin-dependent diabetes.

This shows for the first time that functional beta-like cells can be obtained via in vitro duct culture, suggests the presence and activation of a progenitor cell from pancreatic ducts, and provides a system for the isolation and manipulation of those cells. In one preferred embodiment, the subject method can be used to produce islet-like cell clusters ("ICC") containing a high percentage of $\beta$-epithelial cells with increased insulin production.

Moreover, as demonstrated in the appended examples, the subject cellular compositions can be used to rescue diabetic mice.

Accordingly, certain aspects of the present invention relate to isolated populations of progenitor cells capable of subsequent differentiation to distinct pancreatic lineages, methods for isolating such cells and therapeutic uses for such cells.

In one embodiment, the invention provides a method for isolating pancreatic progenitor cells. In general, the method includes the steps of obtaining pancreatic ductal cells; culturing the pancreatic cells in a suitable nutrient medium; isolating a population of progenitor cells from said culture. In preferred embodiment, the ductal epithelial cells are obtained from intralobular ducts. For instance, the pancreatic ductal epithelial cells can be obtained by enzymatic digestion or other mechanical separation of ductal fragments. The pancreatic ductal cells are grown to confluence, e.g., preferably in a monolayer. Viable, non-adherent cells can be isolated from the culture, optionally after treatment of the culture with an agent(s) that induce proliferation/ differentiation of pancreatic progenitor cells from the adherent epithelial cells. As described below, the non-adherent cell population is enriched for pancreatic progenitor cells.

Another aspect of the invention relates to cellular compositions enriched for pancreatic progenitor cells, or the progeny thereof. In certain embodiments, the cells will be provided as part of a pharmaceutical preparation, e.g., a sterile, free of the presence of unwanted virus, bacteria and other (human) pathogens, as well as pyrogen-free preparation. That is, for human administration, the subject cell preparations should meet sterility, pyrogenicity, general safety and purity standards as required by FDA Office of Biologics standards.

In certain embodiments, such cellular compositions can be used for transplantation into animals, preferably mammals, and even more preferably humans. The cells can be autologous, allogeneic or xenogeneic with respect to the transplantation host. In one aspect, the present invention relates to transplantation of fetal or mature pancreatic cells to treat Type 1 diabetes mellitus.

Another aspect of the present invention relates to our finding that cAMP elevating agents can be used to proliferation and differentiation of pancreatic progenitor cells. In this regard, the invention relates to the use of a cAMP elevating agents to induce ex vivo the proliferation and differentiation of pancreatic cells prior to their transplantation into a diabetic subject. In yet other embodiments, the invention contemplates the in vivo administration of cAMP agonists to patients which have been transplanted with pancreatic tissue, as well as to patients which have a need for improved pancreatic performance, or are at risk for developing functional deficits in the organ, especially of glucose-dependent insulin secretion, e.g., the subject method can be used prophylactically.

(ii) Definitions

For convenience, certain terms employed in the specification, examples, and appended claims are collected here.

As used herein the term "animal" refers to mammals, preferably mammals such as humans. Likewise, a "patient" or "subject" to be treated by the method of the invention can mean either a human or non-human animal.

As used herein, the term "cellular composition" refers to a preparation of cells, which preparation may include, in addition to the cells, non-cellular components such as cell culture media, e.g. proteins, amino acids, nucleic acids, nucleotides, co-enzyme, anti-oxidants, metals and the like. Furthermore, the cellular composition can have components which do not affect the growth or viability of the cellular component, but which are used to provide the cells in a particular format, e.g., as polymeric matrix for encapsulation or a pharmaceutical preparation.

The term "culture medium" is recognized in the art, and refers generally to any substance or preparation used for the cultivation of living cells. Accordingly, a "tissue culture" refers to the maintenance or growth of tissue, e.g., explants of organ primordia or of an adult organ in vitro so as to preserve its architecture and function. A "cell culture" refers to a growth of cells in vitro; although the cells proliferate they do not organize into tissue per se.

Tissue and cell culture preparations of the subject microorgan explants and amplified progenitor cell populations can take on a variey of formats. For instance, a "suspension culture" refers to a culture in which cells multiply while suspended in a suitable medium. Likewise, a "continuous flow culture" refers to the the cultivation of cells or ductal explants in a continuous flow of fresh medium to maintain cell growth, e.g. viablity. The term "conditioned media" refers to the supernatant, e.g. free of the cultured cells/tissue, resulting after a period of time in contact with the cultured cells such that the media has been altered to include certain paracrine and/or autocrine factors produced by the cells and secreted into the culture.

"Differentiation" in the present context means increased numbers of islet-like cell clusters containing an increased proportion of beta-epithelial cells that produce increased amounts of insulin.

The term "$ED_{50}$" means the dose of a drug which produces 50% of its maximum response or effect.

An "effective amount" of, e.g., a cAMP regulator, with respect to the subject method, refers to an amount of a cAMP elevating agent which, when added to the subject pancreatic cells cultures, brings about a change in the rate of cell proliferation and/or the state of differentiation of a cell.

The term "explant" refers to a portion of an organ taken from the body and grown in an artificial medium.

By "ex vivo" is meant cells that have been taken from a body, temporarily cultured in vitro, and returned to a body.

The term "lineage committed cell" refers to a progenitor cell that is no longer pluripotent but has been induced to differentiate into a specific cell type, e.g., a pancreatic, cell.

The term "organ" refers to two or more adjacent layers of tissue, which layers of tissue maintain some form of cell-cell and/or cell-matrix interaction to form a microarchitecture.

The term "primary culture" denotes a mixed cell population of human pancreatic cells that permits interaction of epithelial and mesenchymal cells within ICC. The word "primary" takes its usual meaning in the art of tissue culture.

The term "progenitor cell" refers to an undifferentiated cell which is capable of proliferation and giving rise to more progenitor cells having the ability to generate a large number of mother cells that can in turn give rise to differentiated, or differentiable daughter cells. As used herein, the term "progenitor cell" is also intended to encompass a cell which is sometimes referred to in the art as a "stem cell". In a preferred embodiment, the term "progenitor cell" refers to a generalized mother cell whose descendants (progeny) specialize, often in different directions, by differentiation, e.g., by acquiring completely individual characters, as occurs in progressive diversification of embryonic cells and tissues. "Progenitor cells" refers to progenitor cells arising in tissue of a pancreatic intralobular duct and giving rise to such differentiated progeny as, for example, B cell lineages.

"Proliferation" indicates an increase in cell number.

The term "tissue" refers to a group or layer of similarly specialized cells which together perform certain special functions.

The term "pancreas" is art recognized, and refers generally to a large, elongated, racemose gland situated transversely behind the stomach, between the spleen and duodenum. The pancreatic exocrine function, e.g., external secretion, provides a source of digestive enzymes. Indeed, "pancreatin" refers to a substance from the pancreas containing enzymes, principally amylase, protease, and lipase, which substance is used as a digestive aid. The exocrine portion is composed of several serous cells surrounding a lumen. These cells synthesize and secrete digestive enzymes such as trypsinogen, chymotrypsinogen, carboxypeptidase, ribonuclease, deoxyribonuclease, triacylglycerol lipase, phospholipase $A_2$, elastase, and amylase.

The endocrine portion of the pancreas is composed of the islets of Langerhans. The islets of Langerhans appear as rounded clusters of cells embedded within the exocrine pancreas. Four different types of cells-$\alpha$, $\beta$, $\delta$, and $\phi$-have been identified in the islets. The a cells constitute about 20% of the cells found in pancreatic islets and produce the hormone glucagon. Glucagon acts on several tissues to make energy available in the intervals between feeding. In the liver, glucagon causes breakdown of glycogen and promotes gluconeogenesis from amino acid precursors. The 6 cells produce somatostatin which acts in the pancreas to inhibit glucagon release and to decrease pancreatic exocrine secretion. The hormone pancreatic polypeptide is produced in the $\phi$cells. This hormone inhibits pancreatic exocrine secretion of bicarbonate and enzymes, causes relaxation of the gallbladder, and decreases bile secretion. The most abundant cell in the islets, constituting 60–80% of the cells, is the $\beta$ cell, which produces insulin. Insulin is known to cause the storage of excess nutrients arising during and shortly after feeding. The major target organs for insulin are the liver, muscle, and fat-organs specialized for storage of energy.

The term "pancreatic duct" includes the accessory pancreatic duct, dorsal pancreatic duct, main pancreatic duct and ventral pancreatic duct. Serous glands have extensions of the lumen between adjacent secretory cells, and these are called intercellular canaliculi. The term "interlobular ducts" refers to intercalated ducts and striated ducts found within lobules of secretory units in the pancreas. The "intercalated ducts" refers to the first duct segment draining a secretory acinus or tubule. Intercalated ducts often have carbonic anhydrase activity, such that bicarbonate ion may be added to the secretions at this level. "Striated ducts" are the largest of the intralobular duct components and are capable of modifing the ionic composition of secretions.

The term "pancreatic progenitor cell" refers to a cell which can differentiate into a cell of pancreatic lineage, e.g. a cell which can produce a hormone or enzyme normally produced by a pancreatic cell. For instance, a pancreatic progenitor cell may be caused to differentiate, at least partially, into $\alpha$, $\beta$, $\delta$, or $\phi$ islet cell, or a cell of exocrine fate. The pancreatic progenitor cells of the invention can also be cultured prior to administration to a subject under conditions which promote cell proliferation and differentiation. These conditions include culturing the cells to allow proliferation and confluence in vitro at which time the cells can be made to form pseudo islet-like aggregates or clusters and secrete insulin, glucagon, and somatostatin.

The term "substantially pure", with respect to progenitor cells, refers to a population of progenitor cells that is at least about 75%, preferably at least about 85%, more preferably at least about 90%, and most preferably at least about 95% pure, with respect to progenitor cells making up a total cell population. Recast, the term "substantially pure" refers to a population of progenitor cell of the present invention that contain fewer than about 20%, more preferably fewer than about 10%, most preferably fewer than about 5%, of lineage committed cells in the original unamplified and isolated population prior to subsequent culturing and amplification.

(iii) Exemplary Embodiments

Certain terms being set out above, it is noted that one aspect of the present invention features a method for isolating pancreatic progenitor cells, and differentiated progeny thereof, from pancreatic tissue explants, e.g., ductal tissue explants.

One salient feature of the subject method is that the starting material can be adult pancreatic tissue. Moreover, the method can be practiced with relatively small amounts of starting material. Accordingly, small samples of pancreatic tissue from a donor can be obtained without sacrificing or seriously injuring the donor. The progenitor cells of the present invention can be amplified, and subsequently isolated from the epithelial explant, based on a proliferative response upon, for example, addition of defined growth factors or biological extracts to the culture.

Another salient feature of certain embodiments of the subject method concerns the use of defined culture conditions for isolating and propagating discrete pancreatic progenitor cell populations.

For instance, as described below, the progenitor source ductal tissue explants preferably are digested or otherwise teased apart, thereby providing purified ductal properties, which in turn are placed in the culture medium and grown. The pancreatic duct preparations are permitted to expand and form monolayer of cells in culture, e.g., a ductal epithelial monolayer. In preferred embodiments, the majority (e.g., >25 percent, more preferably >10%) of the cells are vimentin-positive, non-endocrine and proliferative. Viable non-adherent cells (NACs) can be isolated from the culture of otherwise adherent pancreatic cells. As described below, these NAC preparations are enriched for pancreatic progenitor cells.

We have also discovered that ductal cells of the subject cultures, and the NACs arising in the culture, can be purified based on binding to lectins. For example, fluorescently labeled lectins can be used to, e.g., facilitate FACS or other cell sorting. In other embodiments, the lectin can be derivatized for immobilization, e.g., on a solid surface such as a filter or bead, and used for affinity purification of the cells. Exemplary lectins for these purposes include the fluorescent lectins, peroxidase conjugated lectins and biotinylated lectins marketed by Vector Laboratories, Inc. of Burlingame, Calif. In preferred embodiments, the lecting is a plant lectin, and more preferably to peanut agglutinin. In other embodiments, the lectin is selected from the group consisting of Aleuria Aurantia Lectin (AAL); Amaranthus Caudatus Lectin (ACL, ACA); Bauhinia Purpurea Lectin (BPL, BPA); Concanavalin A (Con A); Succinylated Concanavalin A (Con A); Datura Stramonium Lectin (DSL); Dolichos Biflorus Agglutinin (DBA); Erythrina Cristagalli Lectin (ECL, ECA); Euonymus Europaeus Lectin (EEL); Galanthus Nivalis Lectin (GNL); Griffonia (Bandeiraea) Simplicifolia Lectin I (GSL I, BSL I); Isolectin-B4; Griffonia (Bandeiraea) Simplicifolia Lectin II (GSL II, BSL II); Hippeastrum Hybrid Lectin (HHL, AL); Lens Culinaris Agglutinin (LCA, LcH); Lotus Tetragonolobus Lectin (LTL); Lycopersicon Esculentum (Tomato) Lectin (LEL, TL); Maackia Amurensis Lectin I (MAL I); Maackia Amurensis Lectin II (MAL II); Maclura Pomifera Lectin (MPL); Narcissus Pseudonarcissus Lectin (NPL, NPA, DL); Peanut Agglutinin (PNA); Phaseolus Vulgaris Agglutinin (PHA); Pisum Sativum (PSA); Psophocarpus Tetragonolobus Lectin I (PTL I, WBA I); Psophocarpus Tetragonolobus Lectin II (PTL II, WBA II); Ricinus Communis Agglutinin I (RCA I, RCA120); Ricinus Communis Agglutinin II (RCA II, RCA60, ricin); Sambucus Nigra (EBL, SNA); Solanum Tuberosum (Potato) Lectin (STL, PL); Sophora Japonica Agglutinin (SJA); Soybean Agglutinin (SBA); Ulex Europaeus Agglutinin I (UEA I); Ulex Europaeus Aggluutinin II (UEA II); Vicia Villosa Lectin (VVA, VVL); Wheat Germ Agglutinin (WGA); Succinylated Wheat Germ Agglutinin; and Wisteria Floribunda Lectin (WFA, WFL).

In certain embodiments, the dissociated monolayers derived from the ductal explants can be sorted by presence of A2B5 epitope, e.g., the ability to be bound by the A2B5 monoclonal antibody (Eisenbarth et al., (1979) PNAS 76:4913), or other glycolipids present on astrocytes, such as gangliosides like GM3 or GD3.

Moreover, we have unexpectedly found that a combination of growing such cells as monolayers, with treatment of such cultures with cAMP elevating agents produces an increased induction of NACs, e.g., pancreatic progenitor cells. Accordingly, when the ductal cells have grown to confluence (cells covering the surface of a culture plate), the cells cans be treated with a cAMP elevating agent in order to cause differentiation of certain cells in the culture into progenitor cells, and subsequently into insulin-producing or other endocrine or exocrine cells. Accordingly, carefully defined conditions can be acquired in the culture so as selectively activate discrete populations of cells in the tissue explant. The progenitor and differentiated cells of the present invention can be amplified, and subsequently isolated from the culture.

In general, the pancreatic tissue is prepared using any suitable method, such as by gently teasing apart the excised tissue or by digestion of excised tissue with collagenase (for example, collagenase A), via, to illustrate, perfusion through a duct or simple incubation of, for example, teased tissue in a collagenase-containing buffer of suitable pH and tonic strength. The prepared tissue may then, optionally, be concentrated using suitable methods and materials, such as centrifugation through ficol gradients for concentration (and partial purification). The concentrated tissue then is resuspended into any suitable vessel, such as tissue culture glassware or plasticware. In preferred embodiments, the ductal samples are allowed to form a confluent monolayer culture, from which NACs are formed.

In certain embodiments, the culture is contacted with a cAMP elevating agents, such as 8-(4-chlorophenylthio)-adenosine-3':5'-cyclic-monophosphate (CPT-cAMP) (see, for example, Koike Prog. Neuro-Psychopharmacol. and Biol. Psychiat. 16 95–106 (1992)), CPT-cAMP, forskolin, Na-Butyrate, isobutyl methylxanthine (IBMX) and cholera toxin (see Martin et al. J. Neurobiol. 23 1205–1220 (1992)) and 8-bromo-cAMP, dibutyryl-cAMP and dioctanoyl-cAMP (e.g., see Rydel et al. PNAS 85:1257 (1988)).

In certain embodiments, the culture is contacted with a growth factor, e.g., a mitogenic growth factor, e.g., the growth factor is selected from a group consisting of IGF, TGF, FGF, EGF, HGF, hedgehog or VEGF. In other embodiments, the growth factor is a member of the TGFβ superfamily, preferably of the DVR (dpp and vg1 related) family, e.g., BMP2 and/or BMP7.

In certain embodiments, the culture is contacted with a steroid or corticosteroid such as, for example, hydrocortisone, deoxyhydrocortisone, fludrocortisone, prednisolone, methylprednisolone, prednisone, triamcinolone, dexamethasone, betamethasone and paramethasone. See, generally, The Merck Manual of Diagnosis and Therapy, 15th Ed., pp. 1239–1267 and 2497–2506, Berkow et al., eds., Rahay, N.J., 1987).

In a preferred embodiment, the cultures are contacted with a cAMP elevating agent, a growth factor and a steroid or corticosteroid, e.g., with the DCE cocktail described herein.

A salient feature of the subject method concerns the use of defined explants as sources from which discrete progenitor cell populations can be amplified. Thus, in certain embodiments progenitor cells from the explant that proliferate in response to the agent can be isolated, such as by direct mechanical separation from the rest of the explant or by dissolution of all or a portion of the explant and subsequent isolation of the progenitor cell population. Moreover, the subject method generally does not require much starting material. Accordingly, small samples of pancreatic tissue from a donor can be obtained without sacrificing or seriously injuring the donor. The progenitor cells of the present invention can be amplified, and subsequently isolated from the epithelial explant, based on a proliferative response upon, for example, addition of defmed growth factors or biological extracts to the culture.

Alternatively, or in addition, treatment with cAMP upregulating agents can be used as described above to induce differentiation. The cell products of such a method can include insulin-producing cells, and more preferably, glucose-responsive insulin-producing cells.

There are a large number of tissue culture media that exist for culturing tissue from animals. Some of these are complex and some are simple. While it is expected that the ductal epithelial explants may grow in complex media, it will generally be preferred that the explants be maintained in a simple medium, such as Dulbecco's Minimal Essential Media (DMEM), in order to effect more precise control over the activation of certain progenitor populations in the explant. In a preferred embodiment, the pancreatic ductal epithelium is cultured in Isocave modified MEM cell culture medium with 5% FBS. Moreover, the explants can be maintained in the absence of sera for extended periods of time. In preferred embodiments of the invention, the growth factors or other mitogenic agents are not included in the primary media for maintenance of the cultures in vitro, but are used subsequently to cause proliferation of distinct populations of progenitor cells. See the appended examples.

In general, in such an expanded culture procedure a commercial-sized bioreactor, such as the OPTICAL TM culture system, Model 5300E (Charles River Labs.; Wilmington, Mass.), or the CELLMAX TM QUAD cell culture system (Celico, Inc.; Germantown, Md.), is seeded with a primary culture of human pancreatic cells. The bioreactor is perfused with a suitable, complete growth medium supplemented with an appropriately effective concentration of mitogens, and as appropriate, cAMP elevating agents. The β-epithelial cell-containing islet-like clusters can then be harvested. Cells may be cryopreserved prior to use as described, for example, by Beattie et al., Transplantation 56: 1340 (1993).

The cultures may be maintained in any suitable culture vessel, such as a 12 or 24 well microplate, and may be maintained under typical culture conditions for cells isolated from the same animal, e.g., such as 37° C. in 5% $CO_2$. The cultures may be shaken for improved aeration, the speed of shaking being, for example, 12 rpm.

In order to isolate progenitor cells from the ductal cultures, it will generally be desirable to contact the explant with an agent which causes proliferation of one or more populations of progenitor cells in the explant. For instance, a mitogen, e.g., a substance that induces mitosis and cell transformation, can be used to detect a progenitor cell population in the explant, and where desirable, to cause the amplification of that population. To illustrate, a purified or semi-purified preparation of a growth factor can be applied to the culture. Induction of progenitor cells which respond to the applied growth factor can be detected by proliferation of the progenitor cells. However, as described below, amplification of the population need not occur to a large extent in order to use certain techniques for isolating the responsive population.

In yet other embodiments, the ductal explants and/or amplified progenitor cells can be cultured on feeder layers, e.g., layers of feeder cells which secrete inductive factors or polymeric layers containing inductive factors. For example, a matrigel layer can be used to induce hematopoietic progenitor cell expansion, as described in the appended examples. Matrigel (Collaborative Research, Inc., Bedford, Mass.) is a complex mixture of matrix and associated materials derived as an extract of murine basement membrane proteins, consisting predominantly of laminin, collagen IV, heparin sulfate proteoglycan, and nidogen and entactin was prepared from the EHS tumor as described Kleinman et al, "Basement Membrane Complexes with Biological Activity", Biochemistry, Vol. 25 (1986), pages 312–318. Other such matrixes can be provided, such as Humatrix. Likewise, natural and recombinantly engineered cells can be provided as feeder layers to the instant cultures.

As described in further detail below, it is contemplated that the subject methods can be carried out using cyclic AMP (cAMP) agonists to iduce differentiation of the cultures cells of endocrine or exocrine phenotypes. In yet other embodiments, the invention contemplates the in vivo administration of cAMP agonists to patients which have been transplanted with pancreatic tissue, as well as to patients which have a need for improved pancreatic performance, especially of glucose-dependent insulin secretion.

In light of the present disclosure, it will be apparent to those in the art that a variety of different small molecules can be readily identified, for example, by routine drug screening assays, which upregulate cAMP-dependent activities. For example, the subject method can be carried out using compounds which may activate adenylate cyclase include forskolin (FK), cholera toxin (CT), pertussis toxin (PT), prostaglandins (e.g., PGE-1 and PGE-2), colforsin and β-adrenergic receptor agonists. β-Adrenergic receptor agonists (sometimes referred to herein as "β-adrenergic agonists") include albuterol, bambuterol, bitolterol, carbuterol, clenbuterol, clorprenaline, denopamine, dioxethedrine, dopexamine, ephedrine, epinephrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, prenalterol, procaterol, protokylol, reproterol, rimiterol, ritodrine, soterenol, salmeterol, terbutaline, tretoquinol, tulobuterol, and xamoterol.

Compounds which may inhibit cAMP phosphodiesterase (s), and thereby increase the half-life of cAMP, are also useful in the subject method. Such compounds include amrinone, milrinone, xanthine, methylxanthine, anagrelide, cilostamide, medorinone, indolidan, rolipram, 3-isobutyl-1-methylxanthine (IBMX), chelerythrine, cilostazol, glucocorticoids, griseolic acid, etazolate, caffeine, indomethacin, theophylline, papverine, methyl isobutylxanthine (MIX), and fenoxamine.

Certain analogs of cAMP, e.g., which are agonists of cAMP, can also be used Exemplary cAMP analogs which may be useful in the present method include dibutyryl-cAMP (db-cAMP), (8-(4)-chlorophenylthio)-cAMP (cpt-cAMP), 8-[(4-bromo-2,3-dioxobutyl)thio]-cAMP, 2-[(4-bromo-2,3-dioxobutyl)thio]-cAMP, 8-bromo-cAMP, dioctanoyl-cAMP, Sp-adenosine 3':5'-cyclic phosphorothioate, 8-piperidino-cAMP, $N^6$-phenyl-cAMP, 8-methylamino-cAMP, 8-(6-aminohexyl)amino-cAMP, 2'-deoxy-cAMP, $N^6$,2'-O-dibutryl-cAMP, $N^6$,2'-O-disuccinyl-cAMP, $N^6$-monobutyryl-cAMP, 2'-O-monobutyryl-cAMP, 2'-O-monobutryl-8-bromo-cAMP, $N^6$-monobutryl-2'-deoxy-cAMP, and 2'-O-monosuccinyl-cAMP.

Above-listed compounds useful in the subject methods may be modified to increase the bioavailability, activity, or other pharmacologically relevant property of the compound. For example, forskolin has the formula:

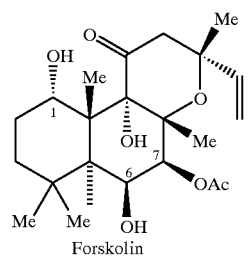

Forskolin

Modifications of forskolin which have been found to increase the hydrophilic character of forskolin without severly attenuating the desired biological activity include acylation of the hydroxyls at C6 and/or C7 (after removal of the acetyl group) with hydrophilic acyl groups. In compounds wherein C6 is acylated with a hydrophilic acyl group, C7 may optionally be deacetylated. Suitable hydrophilic acyl groups include groups having the structure —$(CO)(CH2)_nX$, wherein X is OH or $NR_2$; R is hydrogen, a $C_1$–$C_4$ alkyl group, or two Rs taken together form a ring comprising 3–8 atoms, preferably 5–7 atoms, which may include heteroatoms (e.g., piperazine or morpholine rings); and n is an integer from 1–6, preferably from 1–4, even more preferably from 1–2. Other suitable hydrophilic acyl groups include hydrophilic amino acids or derivatives thereof, such as aspartic acid, glutamic acid, asparagine, glutamine, serine, threonine, tyrosine, etc., including amino acids having a heterocyclic side chain. Forskolin, or other compounds listed above, modified by other possible hydrophilic acyl side chains known to those of skill in the art may be readily synthesized and tested for activity in the present method.

Similarly, variants or derivatives of any of the above-listed compounds may be effective as cAMP agonists in the subject method. Those skilled in the art will readily be able to synthesize and test such derivatives for suitable activity.

In certain embodiments, the subject cAMP agonists can be chosen on the basis of their selectivity for cAMP activation.

In certain embodiments, it may be advantageous to administer two or more of the above cAMP agonists, preferably of different types. For example, use of an adenylate cyclase agonist in conjunction with a cAMP phosphodiesterase antagonist may have an advantageous or synergistic effect.

In certain preferred embodiments, the subject agents raise effective cAMP levels with an $ED_{50}$ of 1 mM or less, more preferably of 1 μM or less, and even more preferably of 1 nM or less.

In certain embodiments of the subject method, it will be desirable to monitor the growth state of cells in the culture, e.g., cell proliferation, differentiation and/or cell death. Methods of measuring cell proliferation are well known in the art and most commonly include determining DNA synthesis characteristic of cell replication. There are numerous methods in the art for measuring DNA synthesis, any of which may be used according to the invention. In an embodiment of the invention, DNA synthesis has been determined using a radioactive label ($^3$H-thymidine) or labeled nucleotide analogues (BrdU) for detection by immunofluorescence.

However, in addition to measuring DNA synthesis, morphological changes can be, and preferably will be, relied on as the basis for isolating responsive progenitor cell populations. For instance, as described in the appended examples, we have observed that certain growth factors cause amplification of progenitor cells in ductal explants so as to form structures that can be easily detected by the naked eye or microscopy. In an exemplary embodiment, those progenitor cells which respond to growth factors by proliferation and subsequent formation of outgrowths from the explant, e.g., buds or blebs, can be easily detected. In another illustrative embodiment, other structural changes, e.g., changes in optical density of proliferating cells, can be detected via contrast microscopy.

To further illustrate, ICCs can be incubated with bromodeoxyuridine ("BrdU"), fixed in formaldehyde, embedded in paraffin and sectioned. Sections can be stained for insulin using an immunoalkaline phosphatase technique described, for exampole, by Erber et al., Am. J. Clin. Path. 88: 43 (1987), using polyclonal guinea pig anti-porcine insulin (Chemicon; El Sequndo, Calif.) as the primary antibody.

Cell nuclei that have incorporated BrdU during DNA synthesis can be identified using mouse monoclonal anti-BrdU (Dako; Carpintaria, Calif.), detected with the immunoperoxidase technique of Sternberger et al., J. Histochem., Cytochem. 18: 315 (1970), followed by hematoxylin counterstaining.

Epithelial cells can be identified on separate sections using a mouse monoclonal anti-epithelial antigen antibody (Ber-EP4, Dako, above) as the primary antibody.

Surface areas of insulin-positive and epithelial cells, calculated as percent of the total ICC area, can be quantified with a computerized image analyzer (American Innovision; San Diego, Calif.). The same method can be used for the determination of the BrdU labeling index. Cells positive for both insulin and BrdU may also be recorded in separate sections of the same samples after double staining of the two antigens.

Mean cell size can be calculated by the ratio of total ICC area to the number of nuclei.

Mean beta-cell size can be estimated by measuring the surface area of individual insulin-positive cells.

A sufficient number of ICC sections (at least 15) and nuclei (at least 1000) should be analyzed for each sample to correct for biological and experimental variability of the samples.

Various techniques may be employed to isolate the activated progenitor cells of treated explant. Preferred isolation procedures for progenitor cells are the ones that result in as little cell death as possible. For example, the activated progenitor cells can be removed from the explant sample by mechanical means, e.g., mechanically sheared off with a pipette. In other instances, it will be possible to dissociate the progenitor cells from the entire explant, or sub-portion thereof, e.g., by enzymatic digestion of the explant, followed by isolation of the activated progenitor cell population based on specific cellular markers, e.g., using affinity separation techniques or fluorescence activated cell sorting (FACS).

To further illustrate, the examples below demonstrate that ductal explants contain growth factor responsive progenitor cell types. It is further demonstrated that different growth factors can induce/amplify distinct populations of progenitor cells within the ductal tissue explant to proliferate. This indicates the presence of specific growth factor receptors on the surface of distinct progenitor cell populations. This is important because the expression of these receptors marks the progenitor cell populations of interest. Monoclonal antibodies are particularly useful for identifying markers (surface membrane proteins, e.g., receptors) associated with particular cell lineages and/or stages of differentiation. Procedures for separation of the subject progenitor cell may include magnetic separation, using antibody coated magnetic beads, affinity chromatography, and "panning" with antibody attached to a solid matrix, e.g., plate, or other convenient technique. Techniques providing accurate separation include fluorescence activated cell sorting, which can have varying degrees of sophistication, e.g., a plurality of color channels, low angle and obtuse light scattering detecting channels, impedance channels, etc.

Conveniently, the antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the cells.

In an illustrative embodiment, some of the antibodies for growth factor receptors that exist on the subject progenitor cells are commercially available (e.g., antibodies for EGF receptors, FGF receptors and/or TGF receptors), and for other growth factor receptors, antibodies can be made by methods well known to one skilled in the art. In addition to using antibodies to isolate progenitor cells of interest, one skilled in the art can also use the growth factors themselves to label the cells, for example, to permit "panning" processes.

Upon isolation, the progenitor cells of the present invention can be further characterized in the following manner: responsiveness to growth factors, specific gene expression, antigenic markers on the surface of such cells, and/or basic morphology.

For example, extent of growth factor responsivity, e.g., the concentration range of growth factor to which they will respond to, the maximal and minimal responses, and to what other growth factors and conditions to which they might respond, can be used to characterize the subject progenitor cells.

Furthermore, the isolated progenitor cells can be characterized by the expression of genes known to mark the developing (i.e., stem or progenitor) cells for the pancreas.

In an illustrative embodiment, the hepatocyte nuclear factor (HNF) transcription factor family, e.g., HNF1–4, are known to be expressed in various cell types at various times during pancreas development. For example, the progenitor cell may express one or more HNF protein such as HNF1α, HNF2β, HNF2β, HNF3γ, and/or HNF4. The glucose transporter Glut2 is also a marker for both early pancreatic cells. Certain of the "forkhead" transcription factors, such as fkh-1 or the like, are understood to be markers in early gut tissue.

In another illustrative embodiment, homeodomain type transcription factors such as STF-1 (also known as IPF-1, IDX-1 or PDX) have recently been shown to mark different populations of the developing pancreas. Some LIM genes have also been shown to regulate insulin gene expression and would also be markers for protodifferentiated β islet cells. Likewise, certain of the PAX genes, such as PAX6, are expressed during pancreas formation and may be used to characterize certain pancreatic progenitor cell populations. Other markers of pancreatic progenitor cells include the pancreas specific transcription factor PTF-1, and hXBP-1 and the like. Moreover, certain of the HNF proteins are expressed during early pancrease development and may used as markers for pancreatic progenitor cells.

Progenitor cells giving rise to pancreatic cells may also express such as markers as villin and/or tyrosine hydroxylase, as well as secrete such factors as insulin, glucagon and/or neuropeptide Y.

Other markers which can be scored in the NACs include: Rab3A (Zahraoui et al. (1989) *J. Biol. Chem.* 12:394; Baldini et al. (1995) *PNAS* 92:4284); vesicle-associated membrane protein 2 (VAMP2, Fujita-Yoshigaki et al. (1996) *J. Biol. Chem.* 271:13130; and Nielsen et al. (1995) *J Clin Invest* 96:1834); amylin, and/or A2B5 (Eisenbarth et al., (1979) *PNAS* 76:4913).

In other embodiments, the subject cultures of small ductal epithelial cells, as well as possibly the pancreatic progenitor cells arsing therefrom, are characterized by binding to lectin(s), and preferably to a plant lectin, and more preferably to peanut agglutinin. In a preferred embodiment, the lectin is peanut agglutinin. In other embodiments, the lectin is selected from the group consisting of Aleuria Aurantia Lectin (AAL); Amaranthus Caudatus Lectin (ACL, ACA); Bauhinia Purpurea Lectin (BPL, BPA); Concanavalin A (Con A); Succinylated Concanavalin A (Con A); Datura Stramonium Lectin (DSL); Dolichos Biflorus Agglutinin (DBA); Erythrina Cristagalli Lectin (ECL, ECA); Euonymus Europaeus Lectin (EEL); Galanthus Nivalis Lectin (GNL); Griffonia (Bandeiraea) Simplicifolia Lectin I (GSL I, BSL I); Isolectin-B4; Griffonia (Bandeiraea) Simplicifolia Lectin II (GSL II, BSL II); Hippeastrum Hybrid Lectin (HHL, AL); Lens Culinaris Agglutinin (LCA, LcH); Lotus Tetragonolobus Lectin (LTL); Lycopersicon Esculentum (Tomato) Lectin (LEL, TL); Maackia Amurensis Lectin I (MAL I); Maackia Amurensis Lectin II (MAL II); Maclura Pomifera Lectin (MPL); Narcissus Pseudonarcissus Lectin (NPL, NPA, DL); Peanut Agglutinin (PNA); Phaseolus Vulgaris Agglutinin (PHA); Pisum Sativum (PSA); Psophocarpus Tetragonolobus Lectin I (PTL I, WBA I); Psophocarpus Tetragonolobus Lectin II (PTL II, WBA II); Ricinus Communis Agglutinin I (RCA I, RCA120); Ricinus Communis Agglutinin II (RCA 11, RCA60, ricin); Sambucus Nigra (EBL, SNA); Solanum Tuberosum (Potato) Lectin (STL, PL); Sophora Japonica Agglutinin (SJA); Soybean Agglutinin (SBA); Ulex Europaeus Agglutinin I (UEA I); Ulex Europaeus Agglutinin II (UEA II); Vicia Villosa Lectin (VVA, VVL); Wheat Germ Agglutinin (WGA); Succinylated Wheat Germ Agglutinin; and Wisteria Floribunda Lectin (WFA, WFL).

For instance, as shown the attached figures, various components of human pancreas can be marked by different lectins. DSL marks inter- and intralobular ducts. LCA appears to mark mesenchyme. ECL marks intralobular ducts without marking larger ducts. Succinylated-Wheat Germ Agglutinin marks a subset of main duct cells and is quite restricted compared to WGA.

Once isolated and characterized, the subject progenitor cells can be cultured under conditions which allow further differentiation into specific cell lineages. This can be achieved through a paradigm of induction that can be developed. For example, the subject progenitor cells can be recombined with the corresponding embryonic tissue to see if the embryonic tissue can instruct the adult cells to codevelop and codifferentiate. Alternatively, the progenitor cells can be contacted with one or more growth or differentiation factors which can induce differentiation of the cells. For instance, the cells can be treated with an agent such as Forskolin, Di-butyrl cAMP, Na-Butyrate, dexamethasone or cholera toxin, or a growth factor such as TGFβ, such as DVR sub-family member.

In another preferred embodiment, the subject progenitor cells can be implanted into one of a number of regeneration models used in the art, e.g., a host animal which has undergone partial pancreatectomy or streptozocin treatment of a host animal.

Accordingly, another aspect of the present invention pertains to the progeny of the subject progenitor cells, e.g. those cells which have been derived from the cells of the initial explant culture. Such progeny can include subsequent generations of progenitor cells, as well as lineage committed cells generated by inducing differentiation of the subject progenitor cells after their isolation from the explant, e.g., induced in vitro.

Yet another aspect of the present invention concerns cellular compositions which include, as a cellular component, substantially pure preparations of the subject progenitor cells, or the progeny thereof. Cellular compositions of the present invention include not only substantially pure populations of the progenitor cells, but can also include cell culture components, e.g., culture media including amino acids, metals, coenzyme factors, as well as small populations of non-progenitor cells, e.g, some of which may arise by subsequent differentiation of isolated progenitor cells of the invention. Furthermore, other non-cellular components include those which render the cellular component suitable for support under particular circumstances, e.g., implantation, e.g., continuous culture.

As common methods of administering the progenitor cells of the present invention to subjects, particularly human subjects, which are described in detail herein, include injection or implantation of the cells into target sites in the subjects, the cells of the invention can be inserted into a delivery device which facilitates introduction by, injection or implantation, of the cells into the subjects. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The progenitor cells of the invention can be inserted into such a delivery device, e.g., a syringe, in different forms. For example, the cells can be suspended in a solution or embedded in a support matrix when contained in such a delivery device. As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating progenitor cells as described herein in a pharmaceutically acceptable carrier or diluent and, as required, other ingredients enumerated above, followed by filtered sterilization.

Support matrices in which the progenitor cells can be incorporated or embedded include matrices which are recipient-compatible and which degrade into products which are not harmful to the recipient. Natural and/or synthetic biodegradable matrices are examples of such matrices. Natural biodegradable matrices include plasma clots, e.g., derived from a mammal, and collagen matrices. Synthetic biodegradable matrices include synthetic polymers such as polyanhydrides, polyorthoesters, and polylactic acid. Other examples of synthetic polymers and methods of incorporating or embedding cells into these matrices are known in the art. See e.g., U.S. Pat. No. 4,298,002 and U.S. Pat. No. 5,308,701. These matrices provide support and protection for the fragile progenitor cells in vivo and are, therefore, the preferred form in which the progenitor cells are introduced into the recipient subjects.

The present invention also provides substantially pure progenitor cells which can be used therapeutically for treatment of various disorders associated with insufficient functioning of the pancreas.

To illustrate, the subject progenitor cells can be used in the treatment or prophylaxis of a variety of pancreatic disorders, both exocrine and endocrine. For instance, the progenitor cells can be used to produce populations of differentiated pancreatic cells for repair subsequent to partial pancreatectomy, e.g., excision of a portion of the pancreas. Likewise, such cell populations can be used to regenerate or replace pancreatic tissue loss due to, pancreatolysis, e.g., destruction of pancreatic tissue, such as pancreatitis, e.g., a condition due to autolysis of pancreatic tissue caused by escape of enzymes into the substance.

In an exemplary embodiment, the subject progenitor cells can be provided for patients suffering from any insulin-deficiency disorder. For instance, each year, over 728,000 new cases of diabetes are diagnosed and 150,000 Americans die from the disease and its complications; the total yearly cost in the United States is over 20 billion dollars (Langer et al. (1993) *Science* 260:920–926). Diabetes is characterized by pancreatic islet destruction or dysfunction leading to loss of glucose control. Diabetes mellitus is a metabolic disorder defined by the presence of chronically elevated levels of blood glucose (hyperglycemia). Insulin-dependent (Type 1) diabetes mellitus ("IDDM") results from an autoimmune-mediated destruction of the pancreatic β-cells with consequent loss of insulin production, which results in hyperglycemia. Type 1 diabetics require insulin replacement therapy to ensure survival. Non-insulin-dependent (Type 2) diabetes mellitus ("NIDDM") is initially characterized by hyperglycemia in the presence of higher-than-normal levels of plasma insulin (hyperinsulinemia). In Type 2 diabetes, tissue processes which control carbohydrate metabolism are believed to have decreased sensitivity to insulin. Progression of the Type 2 diabetic state is associated with increasing concentrations of blood glucose, and coupled with a relative decrease in the rate of glucose-induced insulin secretion.

The primary aim of treatment in both forms of diabetes mellitus is the same, namely, the reduction of blood glucose levels to as near normal as possible. Treatment of Type 1 diabetes involves administration of replacement doses of insulin. In contrast, treatment of Type 2 diabetes frequently does not require administration of insulin. For example, initial therapy of Type 2 diabetes may be based on diet and lifestyle changes augmented by therapy with oral hypoglycemic agents such as sulfonylurea. Insulin therapy may be required, however, especially in the later stages of the disease, to produce control of hyperglycemia in an attempt to minimize complications of the disease, which may arise from islet exhaustion.

More recently, tissue-engineering approaches to treatment have focused on transplanting healthy pancreatic islets, usually encapsulated in a membrane to avoid immune rejection. Three general approaches have been tested in animal models. In the first, a tubular membrane is coiled in a housing that contained islets. The membrane is connected to a polymer graph that in turn connects the device to blood vessels. By manipulation of the membrane permeability, so as to allow free diffusion of glucose and insulin back and forth through the membrane, yet block passage of antibodies and lymphocytes, normoglycemia was maintained in pancreatectomized animals treated with this device (Sullivan et al. (1991) *Science* 252:718).

In a second approach, hollow fibers containing islet cells were immobilized in the polysaccharide alginate. When the device was place intraperitoneally in diabetic animals, blood glucose levels were lowered and good tissue compatibility was observed (Lacey et al. (1991) *Science* 254:1782).

Finally, islets have been placed in microcapsules composed of alginate or polyacrylates. In some cases, animals treated with these microcapsules maintained normoglycemia for over two years (Lim et al. (1980) *Science* 210:908; O'Shea et al. (1984) *Biochim. Biochys. Acta.* 840:133; Sugamori et al. (1989) *Trans. Am. Soc. Artif Intern. Organs* 35:791; Levesque et al. (1992) *Endocrinology* 130:644; and Lim et al. (1992) *Transplantation* 53:1180). However, all of these transplantation strategies require a large, reliable source of donor islets.

The pancreatic progenitor cells of the invention can be used for treatment of diabetes because they have the ability to differentiate into cells of pancreatic lineage, e.g., β islet cells. The progenitor cells of the invention can be cultured in vitro under conditions which can further induce these cells to differentiate into mature pancreatic cells, or they can undergo differentiation in vivo once introduced into a subject. Many methods for encapsulating cells are known in the art. For example, a source of β islet cells producing insulin is encapsulated in implantable hollow fibers. Such fibers can be pre-spun and subsequently loaded with the β islet cells (Aebischer et al. U.S. Pat. No. 4,892,538; Aebischer et al. U.S. Pat. No. 5,106,627; Hoffman et al. (1990) *Expt. Neurobiol.* 110:39–44; Jaeger et al. (1990) *Prog. Brain Res.* 82:41–46; and Aebischer et al. (1991) *J. Biomech. Eng.* 113:178–183), or can be co-extruded with a polymer which acts to form a polymeric coat about the β islet cells (Lim U.S. Pat. No. 4,391,909; Sefton U.S. Pat. No. 4,353,888; Sugamori et al. (1989) *Trans. Am. Artif. Intern. Organs* 35:791–799; Sefton et al. (1987) *Biotehnol. Bioeng.* 29:1135–1143; and Aebischer et al. (1991) *Biomaterials* 12:50–55).

Moreover, in addition to providing a source of implantable cells, either in the form of the progenitor cell population of the differentiated progeny thereof, the subject cells can be used to produce cultures of pancreatic cells for production and purification of secreted factors. For instance, cultured cells can be provided as a source of insulin. Likewise, exocrine cultures can be provided as a source for pancreatin.

Yet another aspect of the present invention provides methods for screening various compounds for their ability to modulate growth, proliferation or differentiation of distinct progenitor cell populations from pancreatic ductal epithelial culture. In an illustrative embodiment, the subject progenitor cells, and their progeny, can be used to screen various compounds or natural products. Such explants can be maintained in minimal culture media for extended periods of time (e.g., for 7–21 days or longer) and can be contacted with any compound, e.g., small molecule or natural product, e.g., growth factor, to determine the effect of such compound on one of cellular growth, proliferation or differentiation of progenitor cells in the explant. Detection and quantification of growth, proliferation or differentiation of these cells in response to a given compound provides a means for determining the compound's efficacy at inducing one of the growth, proliferation or differentiation in a given ductal explant. Methods of measuring cell proliferation are well known in the art and most commonly include determining DNA synthesis characteristic of cell replication. There are numerous methods in the art for measuring DNA synthesis, any of which may be used according to the invention. In an embodiment of the invention, DNA synthesis has been determined using a radioactive label ($^3$H-thymidine) or labeled nucleotide analogues (BrdU) for detection by immunofluorescence. The efficacy of the compound can be assessed by generating dose response curves from data obtained using various concentrations of the compound. A control assay can also be performed to provide a baseline for comparison. Identification of the progenitor cell population (s) amplified in response to a given test agent can be carried out according to such phenotyping as described above.

(iv) Exemplification

The invention now being generally described, it will be more readily understood by reference to the following examples which are included merely for purposes of illustration of certain aspects and embodiments of the present invention, and are not intended to limit the invention.

EXAMPLE 1

Isolation of Pancreatic Progenitor Cells

METHODS

Duct Isolation and Culture

Pancreata from two litters of 2 week old Sprague-Dawley rat pups were isolated and placed into 10 ml of (1 U/ml in DMEM) Collagenase A (Boehringer-Mannheim, St. Louis) and digested for 40 min at 37° C. in a shaking water bath at 150–175 rpm. The digest was vortexed briefly and washed once with $C^{++}/Mg^{++}$-free HBSS (Gibeo BRL, Grand Island, N.Y.). The pellet was resuspended in HBSS and filtered through a 500 μm mesh (Costar Corning, Cambridge, Mass.) and washed again. The pellet was resuspended to 50 ml in HBSS; 10 ml was transferred to a 10 cm culture plate (Costa & Corning) and placed under a dissecting scope. Individual duct fragments were selected by aspiration with a micropipette and transferred to a plate containing medium with serum. The fragments were selected from this plate a second time, transferred to a fresh tube of medium and serum, and washed before being plated. Fragments were cultured on plastic in Iscoveis modified DMEM (Gibco-BRL) containing 5% FBS (Gibco-BRL), glutamine and 1% Pen/Strep (Gibco-BRL). For the study of individual duct fragments, ducts were grown on 8 well chamber slides (Lab-Tek, Naperville Ill.). For generating monolayers or NACs, duct fragments were plated to four 4-well plates (Nunc) per prep. Induction of NACs was achieved by a medium change after confluence (generally day 5 in culture) to Iscoveis DMEM supplemented with 5% FBS, glutamine, Pen/Strep and Dexamethasone (1 μM, Sigma), Cholera Toxin (100 ng/ml, Sigma), and EGF (10 ng/ml, Gibco). NACs were harvested after 48 hours.

Immunocytochemisty

Cultures, ducts, and non-adherent cells were fixed in 1% paraformaldehyde and permeabilized in PBS containing 0.3% TritonX-100 (PBST). Nonspecific binding sites were blocked by preincubation in a blocking buffer consisting of 5% normal donkey serum (Jackson ImmunoResearch) and 1% BSA (Sigma) in PBST. All antibodies were diluted in this blocking buffer. Incubations with primary antibody were carried out overnight at 4° C. in a humidified chamber. Primary antibodies used were: guinea pig anti-insulin (Linco, 1:2000); mouse anti-insulin/proinsulin (Biodesign, directly conjugated to biotin using a labeling kit from Boehringer Mannheim); guinea pig anti-glucagon (Linco, 1:2500), mouse anti-somatostatin (Biomeda, 1:50); rabbit anti-pancreatic polypeptide (Zymed, 1:50); rabbit anti-amylase (Sigma, 1: 1500), and rabbit anti-PDX-1 (gift of Christopher Wright, Vanderbilt, 1:2000). Secondary antibodies and tertiary reagents were: FITC-conjugated donkey anti-guinea pig IgG (Jackson ImmunoResearch, 1:200); Cy3-conjugated donkey anti-guinea pig, rabbit, or mouse IgG (Jackson, 1:1000); biotin-conjugated donkey anti-rabbit or mouse IgG (Jackson, 1:500); AvidinD-FITC (Vector Labs, 1:1000); streptavidin-Cy3 (Jackson, 1:1000). Cells were scored on a Nikon Eclipse E800 epifluorescent or Nikon Diaphot 300 inverted fluorescent/phase photomicroscope.

Single Cell cDNA Amplification and PCR Analysis cDNAs from single cells were amplified according to Brady et al. (1993) and Dulac and Axel (1995). Single NACs were randomly picked and transferred into PCR tubes containing ice-cold lysis buffer. The first strand cDNA synthesis and subsequent PCR amplification were performed exactly as described (Dulac and Axel, 1995) except that the PCR reactions were performed in a total volume of 50 μl instead of 100 μl. The amplified cDNAs were electrophoresed on a 1% agarose gel and the size of DNA fragments ranged from 0.5–1 kb as expected. The aliquots of individual cDNAs were then analyzed for marker genes by PCR using specific PCR primers. The PCR reactions were run for 35 cycles each at 94° C. for 30 sec, 55° C. for 1 min, and 72° C. for 2 min. Amplimer sequences were: ATGTCGTCCAGGC-CGCTCTGGACAAAATATGAATTCT$_{24}$ (SEQ ID NO.1); insulin: 5ı primer, CACAACTGGAGCTGGGTGGAG (SEQ ID NO.2); 3ı primer, CAAAGGCTTTATTCATTG-CAGAGG (SEQ ID NO.3); PDX-1: 5ı primer, GACCG-CAGGCTGAGGGTGAG (SEQ ID NO.4); 3ı primer, CAGAGGTCTGCCAGCATCTCG (SEQ ID NO.5); glucagon: 5ı primer, TCCCAGAAGAAGTCGCCATTG (SEQ ID NO.6); 3ı primer, TTCATTCCGCAGAGATGTTGRG (SEQ ID NO.7); beta-actin: 5' primer, AAG TCC CTC ACC CTC CCA AAA G (SEQ ID NO.8); 3' primer, AAC ACC TCA AAC CAC TCC CAG G (SEQ ID NO.9).

Insulin Release Assay

Insulin release was measured under static incubation conditions using NACs, isolated ducts, monolayer cells, or batches of 10 islets. Cells or islets were preincubated in Krebs Ringer Phosphate buffer (KRP) containing 3 mM Glucose (Sigma) and 0.2% BSA (Sigma) for 30 minutes at 37° C. Supernatant was collected and the cells washed once before further incubation in 17 mM glucose for 1 hour at 37° C. This supernatant was then collected and all samples were kept at −20° C. until the insulin-specific radioinunuoassay was performed using a RIA kit for rat C-peptide from Linco Research (St. Charles, Mo.). For insulin content measurements, cells were extracted in acid-ethanol and sonicated prior to assay.

Calcium Imaging

NACs were immobilized in 0.7% low melting agarose in Hanks buffer (GIBCO) and dye-loaded for 1 hour at room temperature with 5 μM Fluo-3 acetoxy-methyl (AM) ester (Molecular Probes) in standard Krebs Ringer Phosphate (KRP) buffer that additionally contained 0.1% pluronic acid (Molecular Probes) and 1% dimethyl sulfoxide (Sigma). Cells were then washed to remove excess dye and placed onto a heated microscope stage 30 (Olympus) and maintained at 32° C. Fluo-3 fluorescence intensity was used as an indicator of intracellular calcium concentration and was measured with a confocal laser-scanning microscope (Olympus). The excitation wavelength was set to 488 nm (argon ion laser) and a 40× water lens was used. The same parameters for laser scanning were set for each experiment, including confocal aperture and laser intensity. The laser scanning was performed as an XYT series with an interval of 10 seconds between each scan in order to resolve glucose-induced changes in intracellular calcium. The imaging files were stored and subsequently analyzed with FLUOVIEW software (Olympus). Cells of interest were circled and the mean intensity of the circled areas was plotted over time.

RESULTS

Isolation, Characterization and Culture of Pancreatic Ducts

In order to establish a defined in vitro culture system, a population of interlobular ducts was isolated and characterized. Adult tissue from 1–2 month old animals was initially used to establish the described culture system, but was eventually replaced with tissue from 2–3 week old rats which provide a more consistent and greater yield of clean ducts. Pancreatic tissue was harvested and subjected to collagenase digestion (Githens & Whelan, 1983; Githens et al. 1989). Digested tissue was then handpicked in multiple iterations until a pure population of ducts was obtained (FIG. 1). A typical experiment provided up to 200–300 fairly uniform duct fragments per 20 animals. Staining for tubulin beta III and acetylated-LDL-DiI showed that the selected duct population was free of neurons and blood vessels (not shown).

Characterization of the starting material was performed by analyzing single ducts for expression of insulin, PDX-1, PYY, and amylase. Table 1 shows that the majority of the handpicked ducts at time zero were free of these endocrine and exocrine markers. Greater than 92% of all ducts contained no insulin-immunopositive cells at the start of culture, and a similar proportion of all ducts had no immunohistochemically detectable PDX-1. Of those ducts that tested positive, almost all had only 1–2 cells that were insulin immunopositive. Analysis of dissociated ducts also showed that less than 0.05% of time zero duct cells were immunopositive for insulin and PDX-1 protein (not shown). Similarly, PYY-containing cells were rare, constituting no more than 0.015% of the counted cells. Amylase-positive cells constituted 0.02% of the initial population and probably represented exocrine carryover since they occurred in rare clusters. The number of cells expressing either PDX-1 or the endocrine markers insulin or PYY totaled much less than 0.1% of the cells (Table 1), corroborating the immunohistochemical observations on sections of adult pancreas that these cells are rare in mature ducts (data not shown). Since the average duct fragment contained 3450±1860 cells (n=10 determinations), and the average duct yield was 225 fragments, the initial number of insulin positive cells at the start of culture ranged from 80–400 per approximately 800,000 cells (Table 1).

Culturing was performed by placing single duct fragments within a 1 cm$^2$ well (FIG. 2) or multiple fragments into 4-well plates (1.9 cm$^2$/well). Various substrates were tested (Matrigel, collagen, hydrogels) but the cleanest and most interesting results were obtained by simply plating onto charged plastic. Iscoveis Modified Dulbeccois Media (IMDM) containing 5% fetal calf serum (FCS) was added to each well and the ducts cultured over 5 days. The top panel in FIG. 2 shows insulin staining in a time series of cultured ducts and the bottom panel the corresponding bright field images. An analysis of single duct populations indicated that whereas at time zero 8% of the duct fragments were positive for insulin (Table 1), in as short a time as 24 hours, the number of ducts containing insulin-positive cells had increased to 13% and to 17% by day two. These positives appeared most frequently as single cells or small foci of 2–4 cells (FIG. 2). By day five of individual culture 23–25% of the wells contained insulin-positive cells on the monolayer, with little change thereafter (through day seven, $^{46}/_{185}$ single duct cultures). One implication of these results is that non-insulin positive ducts become insulin-positive through culture.

Increasing the number of duct fragments per well resulted in a more rapid outgrowth and confluence of the monolayer generally within 5 days, suggesting that some cross-feeding takes place. We have standardized our platings to 16 wells (1.9 cm$^2$) per duct preparation as a balance between time and cell yield. At seven days of culture in FBS(T7), the monolayer contains an average of 25±20 (range 0–51) insulin-positive cells per well (0.02% of total cells) for a maximum expansion of 5-fold over the starting material. In this system, the majority of cells are vimentin-positive, non-endocrine and proliferative (as indicated by BrdU uptake), and probably arise from the stromal cells surrounding the epithelial layer of duct cells. The insulin-positive cells are capable of BrdU uptake but this occurs rarely (not shown). The bulk of BrdU uptake is by vimentin-positive fibroblasts. The slow growth rate of the early appearing insulin-positive cells on the monolayer agrees with observations from other investigators demonstrating that beta cells replicate very infrequently in vitro and in vivo (reviewed by Sjoholm, 1996; Nielsen et al. 1999). Further culture beyond seven days did not significantly increase either the number of wells containing insulin-positive cells or the number of insulin-positive cells.

In addition to an increase in the number of cells expressing insulin, we also observed that some wells in FBS culture contained a number of amylase-positive cells, often cells that coexpressed insulin (FIGS. 3A–C). Cells expressing both insulin and amylase have been documented to appear during pancreatic regeneration and are thought to be activated progenitor cells (Melmed, 1979, Ou et al. 1994). In addition, these cultures contained a rounded and semiadherent cell type, many of which appear to express both markers although the insulin is faint.

Cells that express PYY and/or glucagon are observed in our duct cultures (FIG. 3D–F). The coexpression of PYY and glucagon during early pancreatic development has been postulated to mark endocrine progenitor cell progression (Upchurch et al. 1994). In contrast to insulin, the number of PYY-positive cells did not change during culture (Table 2). Of cells that were insulin-positive on the monolayer, most but not all coexpressed PDX-1. Cells that expressed PDX-1 but did not yet express insulin and vice versa were also observed in culture (FIG. 3G, arrows). Thus cells representing various stages of differentiation and different developmental lineages appear in our cultures.

Appearance of a Non-adherent Cell Type

The number of insulin-positive cells did not increase significantly with culture beyond 5 days due to their slow replication rate and perhaps cell death. Factors were added to T5 cultures to determine if an increase in the number of insulin-positive cells could be induced. A number of factors that affect either epithelial cells or pancreatic development were tested: dexamethasone, cholera toxin, EGF, TGFα, PDGFα, HGF, TGFβ1, IL-1α, GLP-1, glucagon, gastrin, GIP, PYY, NPY, and PP were added to T5 cultures for 2 further days of incubation. When tested alone most of the factors did not significantly boost the number of observed insulin-positive cells (not shown). However, a cocktail of DCE, dexamethasone, cholera toxin and EGF, significantly increased the number of insulin-positive cells on the monolayer (an average increase of 2–3 fold over n=8 experiments, Table 1). In addition, the presence of DCE significantly enhanced the appearance of a population of non-adherent cells (NACs) over the course of 48 hours (FIG. 4). NACs were observed even in control cultures (FIG. 4A) as well as in growth factor-treated cultures (FIGS. 4C,D), but none of these conditions led to the level of induction seen with DCE. In the examples shown, HGF and TGFβ1 were tested for effects on the monolayer. HGF has been shown to stimulate the growth of fetal islets (Otonkoski et al. 1994) and TGFβ1 has been shown to inhibit the appearance of endocrine cells in in vitro pancreatic culture (Sanvito et al. 1994). In our system, HGF and TGFβ1 had only slight effects on culture phenotype or NAC production.

NACs appear spontaneously in confluent monolayer cultures. Both the number and rate of appearance of NACs are significantly increased (often >8-fold) by the addition of the DCE cocktail (FIG. 4B). These cells are characteristically phase-bright, possess a secretory appearance with high granularity, and generally range in size from 20–50 μm (FIG. 4 inset). True NACs most often appear as large round cells freely floating at the surface of the monolayer. Many others are often still attached and apparently in the process of emerging. An increase in NACs can be seen by 24 hours post-DCE addition, but appears maximal at 48 hours.

Repeated dosing of DCE into the cultures gave rise to successive waves of NAC formation but with successively fewer numbers (not shown).

DCE has previously been shown to promote the growth and function of primary purified pancreatic epithelial cultures (Githens et al. 1987, 1989), but no NACS or endocrine cell types were reported. Perhaps the effect of DCE is indirect; working on the stromal component of our mixed cell culture system to induce the differentiation of beta and other islet cell types. Subsequent testing in our cultures showed that neither dexamethasone not EGF alone had significant effects on NAC generation in comparison to controls, but that the majority of the activity was associated with the cAMP-elevating effects of the cholera toxin. In fact, many cAMP agonists also had this effect (data not shown; to be described elsewhere). The presence of dexamethasone and EGF appeared to enhance the effect of CT. The size and granularity of the cells within the NAC population varied markedly, but vital dye staining showed greater than 99% of the NACs to be viable.

In terms of the number of ducts that were responsive to DCE, over 95% of the DCE-treated wells (n>10 experiments, single duct per well) gave rise to at least a 2-fold increase in NACs over control wells. Each treated well in a normal culture (8–16 ducts per well) yielded 3,000–18,000 NACs after 48 hours in DCE (n=9 experiments) with an average yield of about 7000 per well or approximately $1 \times 10^5$ NAC cells per prep. BrdU incorporation experiments demonstrated that one of the effects of DCE is to stimulate cell division. Pulsing at the end of the 48 hours showed 4-fold more BrdU-positive cells in the DCE-treated monolayers than in controls, indicating a long-lasting stimulation of proliferation (not shown). When pulsed at the beginning of DCE addition, 10% of the NACs recovered at 48 hours were BrdU-positive, indicating that these cells may derive from a DCE-responsive, cycling cell. DCE does not appear simply to stimulate the loss of cell adhesion.

Hormone Expression in NACs

Analysis of the monolayer demonstrated that approximately 0.02% of the cells in FBS culture expressed insulin (see Table 1), with DCE addition increasing that number 2–3 fold to give an average of 59±52 (range 5–196) insulin-positive cells per well. In addition to analysis of the monolayer, NACs were analyzed for expression of insulin and other endocrine markers. Since NACs are free-floating in the media, they were collected by aspiration at 48 hours post DCE addition, when their appearance was maximal. All four islet endocrine cell types could be detected immunocytochemically in this population. FIG. 5 shows NAC immunostaining for insulin, PDX-1, glucagon, somatostatin, and pancreatic polypeptide. As shown in FIG. 5A, insulin labeling demonstrated a continuum of fluorescence intensity with approximately 4–5% of the cells consistently bright (range 2.5–13%, n=6 measurements), and the majority of positive cells (>30–40% of the total cell population) exhibiting low levels of immunofluorescence (A, C) that were still above background (B). This number of low-insulin-expressing cells was confirmed by FACS analysis (data to be described elsewhere). Cells expressing PDX-1, glucagon, somatostatin, and pancreatic polypeptide were also present in the population (D, E, F and G respectively), with glucagon-positive cells being the next most frequent (6%), followed by somatostatin (3%) and pancreatic polypeptide cells the rarest (2%). The NAC population thus constitutes an enrichment from a cultured monolayer of the full set of islet endocrine cell types.

Transcriptional Profiling

As a further determination of the number of insulin-expressing cells within the NAC population, we also performed semi-quantitative single-cell PCR (Brady et al. 1993, Dulac & Axel, 1995) to detect insulin mRNA in randomly selected individual NACs. FIG. 6 shows that 15 of 40 or >35% of the cells analyzed contained insulin mRNA. Panel A demonstrates that cDNA was amplified from each single cell sample. Panel B shows that the insulin message varied in intensity among the positive cells. This variation in signal intensity, similar to that observed by immunocytochemisty, was also observed and verified by array hybridization analysis (data not shown). Two of the 40 selected cells contained glucagon message (Panel C) with one of them also containing insulin and PDX-1 message. Panel D shows that greater than 80% ($^{35}/_{40}$) of the cells analyzed contained PDX-1 message. Only one of the insulin-positive cells did not express PDX1, whereas there were many cells that were PDX-1 positive with no detectable insulin or glucagon message. The absolute and relative numbers of insulin and glucagon cells are in good agreement with that observed by immunocytochemistry, and in the case of insulin, with flow analysis as well. Interestingly, there were a number of NACs that did not express any of the three markers. The identities of these cells is currently unknown. Array hybridization analysis of the 40 cDNAs with a labeled probe to the ribosomal component S6 (RPS6) demonstrated its presence in all samples (not shown). Transcriptional profiling confirms the immunocytochemistry results that many of the NACs express PDX-1, that approximately 40% of the cells are both insulin mRNA and protein positive, albeit at varying levels, and that the majority of NACs appear to have a beta cell phenotype. In addition, there is a significant fraction of cells that are PDX-1 positive but insulin-negative, which might indicate progenitor cell status. SC-PCR of monolayer cells showed 23/23 actin-positive, 0/23 insulin positive cells (not shown), demonstrating the relative enrichment of endocrine phenotypes in the NAC population.

Insulin Content and Glucose-stimulated Insulin Secretion

A hallmark of functional beta cells is their ability to secrete insulin in response to elevated glucose levels. In order to determine whether there are functional beta cells within the duct cultures, we performed static insulin release assays on both the monolayer and the NAC populations to determine their responses to glucose challenge. We also measured total insulin content by RIA in order to determine the relative increase in insulin expression due culture. FIG. 7 shows the glucose-induced insulin release in isolated time zero ducts, DCE-cultured monolayer, and harvested NACs. The NAC population demonstrated a 3-fold increase in secreted insulin in response to elevated glucose. In contrast, the cells contained in the monolayer exhibited little glucose response and secreted far less insulin in either high or low glucose conditions. Analysis of the time zero ducts (n=3) showed no glucose-stimulated insulin secretion and acid-ethanol extraction of the ducts showed no detectable insulin within the level of sensitivity (approx. 100 $\mu$g/ml) of the RIA. Extraction for total insulin showed a content of 1.34 ng of insulin per 50,000 cells on the monolayer, and 25.0 ng of insulin per 50,000 NAC cells. In comparison, a normal rat islet of approximately 1000 cells typically contains about 20 ng of insulin (data not shown). Furthermore, when NACs recovered from cultures exposed to DCE for 24, 48, or 72 hours were compared, only the NACs from the 48-hour cultures demonstrated a reliable glucose-stimulated insulin response. The data thus show a large increase in the amount of insulin produced through duct culture and that the insulin can be productively released in response to glucose, demonstrating the presence of functional beta cells. Current studies in are focused on further understanding of the variables leading to increased cell number, insulin content and/or functionality.

Demonstration of a Glucose-stimulated Reversible Calcium Current

A key question to address is how many of the insulin-containing cells generated in culture possess a functional glucose response. One way to determine this is to measure the number of cells capable of generating an inward calcium current in response to glucose administration. Insulin secretion is known to be mediated by an inward calcium current linked to glucose metabolism (Kalkhoff & Siegesmund, 1981, Wang & McDaniel, 1990). To assess the presence and number of functional beta cells within the culture, we measured cytosolic calcium influx in response to glucose using the calcium-dependent fluorescent dye Fluo-3. The results of a representative experiment (n>10) using NACs is shown in FIG. 8. In this example 33% of the sampled cells showed strong amplitude and kinetics of calcium current induction in response to elevated glucose. Measurements of cells still attached to the monolayer failed to detect glucose-induced changes in intracellular calcium.

The amplitude and kinetics of the glucose-induced calcium current that we observe in our duct culture-derived beta cells are similar with those documented to occur in islet-derived beta cells (Asada et al. 1998; Schuit, 1996). Cell-to-cell variations in the amplitude and kinetics of glucose induced calcium currents have been interpreted as evidence of heterogeneity in beta cell physiology. Single beta cells studied in isolation have been shown to have altered insulin secretion rates and glucose sensitivity in comparison to intact islets (Halban et al. 1982; Bosco et al. 1989), and individual beta cells have been shown to have markedly different rates of insulin synthesis (Moitoso de Vargas et al. 1997), all of which are observed in our culture. The amplitude variation in calcium currents might also be explained by differences in Fluo-3 dye loading.

The characteristic calcium current profile was not induced by 2-deoxyglucose, a non-metabolized glucose analog (Niki et al. 1974, 1993; Malaisse 1979). It was completely inhibited by diazoxide, a high affinity inhibitor of the SUR-linked potassium channel (Thomas et al. 1996) that is necessary for calcium-induced insulin secretion (Henquin et al. 1982; Trube et al. 1986), and was also inhibited by EGTA (Wollheim & Sharp 1981; Wang & McDaniel, 1990), which sequesters extracellular calcium (not shown). It could however be activated by tolbutamide, a high-affinity activator of the SUR-linked potassium channel, which is used specifically to stimulate insulin secretion in diabetics (Sato et al. 1999; Melander, 1998). The reversibility of this stimulated calcium current is demonstrated in FIG. 8B. In these experiments (n=3) 10% of the cells could respond reversibly to glucose and be stimulated finally by the insulin secretagogue tolbutamide. Fifty-five percent of the cells did not respond to either stimulus, and the remaining 35% of the cells responded either to glucose but not tolbutamide, or to tolbutamide but not glucose, indicating a heterogeneous and complex population. We conclude that, despite having heterogeneous insulin expression levels, 10–40% of the NACs could respond to glucose and thus behave like functional beta cells.

DISCUSSION

We describe here an in vitro culture system that allows the study of functional beta cell formation from a purified pancreatic duct population. Culture of such ducts resulted both in an increase in insulin-positive cells over time and an increase in the total number of duct fragments that became insulin-positive. This latter result indicates that cells capable of expressing insulin may become activated during culture. In addition to these results, we describe the appearance of an interesting population of non-adherent cells that arises during culture, and whose numbers and emergence can be directly regulated by addition of factors and agents.

These non-adherent cells, which we refer to as NACs, are heterogeneous in size, granularity, and marker expression. Immunocytochemical analysis shows that all four islet endocrine markers can be detected within this population. Our analysis also shows that these cells appear in ratios similar to their ratios in the adult pancreatic islet, with the insulin expressing cells being the most numerous, followed by glucagon, somatostatin, and pancreatic polypeptide. Because of their relevance to human disease, assessing the number and functionality of the insulin-expressing cells has been our major focus.

The handpicked duct material contained very few insulin-positive cells at the start of culture. Analysis of the number of insulin-positive cells at the start and endpoint of culture demonstrated an increase of up to 500-fold, primarily in the new nonadherent cell population. Since the insulin-positive cells observed early in culture rarely incorporated BrdU, we propose that the majority of the observed beta-like cells arose from an expanding precursor within the duct.

The mechanism of DCE stimulation of insulin expression and NAC formation is not known. One of the components, dexamethasone, is a glucocorticoid analog known to have multiple effects on pancreas, including stimulation of fetal islet differentiation (Korsgren et al. 1993), stimulation of pancreatic tumor cell growth (Brons et al. 1984), and upregulation of exocrine marker expression (Rall et al. 1977; Van Nest et al. 1983), but surprisingly also suppresses insulin expression in mature mouse islets (Lambillotte et al. 1997). Glucocorticoids have also been shown to upregulate EGF receptor expression in some cell types such as hepatocytes (Gladhaug et al. 1989). EGF is an important mitogen and regulator of gastric and pancreatic epithelium (Meittinen 1997), and in fact has been shown to stimulate epithelial-like outgrowths in cultured pancreatic ducts (Heimann & Githens 1991). Agents such as cholera toxin which raise intracellular cAMP levels have been shown to stimulate epithelial cell properties (Rindler et al. 1979), and cholera toxin in combination with EGF has been shown to induce cyst formation in pancreatic duct and islet cultures (Heimann & Githens, 1991; Yuan et al. 1996). Interestingly, Heimann and Githens (1991) used this combination of DCE to identify and purify ductal epithelium from fibroblasts through the stimulation of cyst formation in collagen or agarose-embedded cultures. In our hands, continuous culture of ducts in DCE also leads to monolayer formation, but without NAC formation. It may be that the choices of culture architecture (embedded versus flat monolayer) and the timing of factor addition are responsible for these differences, and these are currently being investigated.

Perhaps due to the early and possibly immature nature of the generated cells, or the fact that the cells have not yet formed the electrical contacts required for full islet function, the level of hormone expression found within individual monolayer or NAC cells was much lower than in adult beta cells. Our insulin extraction studies indicated that the average NAC cell contains 20–50 fold less insulin than a comparable adult rat beta cell. It may be that only the insulin ebrighti cells possess a glucose response and that the edimi cells represent less mature, non-glucose responsive pre-beta cells. Nonetheless, a much larger proportion of cells could be demonstrated to possess a glucose-stimulated insulin secretion response in the NAC population than in a randomly selected population of monolayer cells. It is. likely that our culture system is missing the trophic influences necessary for stimulating cell-cell contact, full hormone expression and complete beta cell maturation. A number of factors have been shown to increase fetal beta cell insulin expression and enhance insulin secretion (Otonkoski et al., 1993, 1994; Huotari et al., 1998; Sorenson & Brelje, 1997) and these are currently being tested in our system.

The system we describe herein allows for the first time the in vitro study of regenerative and neogenic events that until now have only been described in vivo. We show that the system can be manipulated to give a range of cell identities, that a significant increasie in insulin-positive cells can be obtained and that within this population of cells, beta cell-like function can be detected. Our studies indicate that much of the regenerative and stem cell activities ascribed to the pancreatic duct system by in vivo manipulations can be recapitulated through in vitro culture. This system now makes possible a systematic search for those cells responsible for these activities as well as the identification of factors that influence their numbers, hormone content, and functionality. In addition, this system constitutes the first step towards achieving the goal of a controlled and defined process to create functional beta cells through a naturally occurring, non-cell-engineered process as a therapeutic pathway for the treatment of insulin-dependent diabetes.

EXAMPLE 2

Induction of Pancreatic Progenitor Cell Differentiation

The monolayer can be grown in the presence of EGF (10 ng/ml) or TGF-a (10 ng/ml) to enhance growth. Induction of differentiation is believed to be cAMP dependent. Agents which induce an increase in intracellular cAMP levels are anticipated to induce differentiation.

The cocktail DCE (1 µM Dexamethasone, 100 ng/ml Cholera toxin, 10 ng/ml EGF induces an increase in the number of insulin positive cells in the cultured duct monolayers. FIG. 9 shows the comparison of monolayers treated with DCE+5% FCS versus 5% FCS alone. Ducts were cultured for five days and then treated for an additional 48 hours. Note that there is an approximate 5-fold increase in the total number of insulin positive cells in the culture in response to DCE treatment. The total number of cells in the culture also increases by approximately 20%. The bars represent the average of quadruplicate wells.

Dexamethasone, Cholera toxin, Forskolin, Dibutyrl cAMP and Na-Butyrate have all been tested and found to induce differentiation. FIG. 10 shows that Forskolin, Dibutyrl cAMP and Na-Butyrate can substitute for DCE in inducing the appearance of floating progenitor cells. Briefly, monolayers of ductal fragments induced after 5 days culture with the cAMP agonists forskolin and dibutyryl cAMP as well as the fetal islet differentiating agent sodium butyrate. Both low and high concentrations of each factor were applied to the duct monolayer. After 48 hours, the resultant NACS were collected and counted. Treatments are shown on the x-axis and number of floating progenitor cells is shown on the y-axis. Each bar is the added total of duplicate wells.

We have also observed that secretin can induce differentiation of the monolayer and the appearance on pancreatic progenitor cells. In FIG. 11, after 5 days of culture, secretin was added to the monolayers in a dose range of 1–100 nM. The number of floating progenitor cells was determined after 48 hours of treatment. Each bar represents the total of two combined 1.9 cm$^2$ wells.

The duct cultures used in FIG. 12 were cultured as described above. After 48 hours in varying secretin doses, both the number of insulin positive cells on the monolayer and the total number of floating progenitor cells were counted and scored. Scoring of insulin was done by immunocytochemistry. Note that there is a dose dependent increase in the number of floating progenitor cells. The number of insulin positive cells in the monolayer also increases with secretin dose and the apparent decrease in insulin positive cells at the 50 nm dose is anomalous. Each point represents the average of duplicate wells. The left hand y-axis denotes the total number of obtained floating progenitor cells, and the right hand y-axis denotes the number of insulin positive cells per well. Secretin dose is shown on the x-axis.

FIG. 13 demonstrates that Vasoactive Intestinal Peptide (VIP) also differentiates duct monolayers by inducing the appearance of floating progenitor cells. After five days in culture, VIP was added to the cultures and the number of induced floating progenitor cells was determined after 48 hours of treatment. C=control and is 5%FCS. The optimal dosage in this experiment was 50 ng/ml of VIP, which induced a >3-fold increase int he number of floating progenitor cells versus control. The y-axis denotes the number of such cells (×100). Each bar is the total of two pooled wells.

We also observed that the presence of insulin diminishes secretin-induced differentiation. See FIG. 14. Floating progenitor cells were induced with secretin (100 nM). Simultaneous addition of insulin (10 ng/ml) with secretin diminished the overall induction of floating progenitor cells. Each bar represents the total of two pooled duplicate wells and the number is expressed on the y-axis as number cells (×100).

EXAMPLE 3

Isolation of Pancreatic Progenitor Cells using Lectin Cell-surface Marker

We also set out to identify cell-type specific markers which could be used to isolate/purify pancreatic progenitor cells, or the pancreatic/ductal epithelial which gives rise to such progenitor cells. Amongs the various canidate reagents we tested, we discovered that certain lectins preferentially bound to, and therefor facilitate the isolation of, duct epithelial cells ultimately able to produce pancreatic progenitor cells.

*Arachis hypogaea* (Peanut Agglutinin, PNA) is a plant lectin that binds to specific carbohydrate groups on cell surfaces. PNA binds to galactosyl (β1,3) N-acetyl galactosamine. It was initially selected for study as a beta cell marker (ref: Heald K A, Hail C A, Hurst R P, Kane N, Downing R, *Diabetes Res* 1991 May;17(1):1–6, Separation of beta-cells from dispersed porcine pancreas by selective lectin binding); however, in our hands, PNA did NOT label islet cells from rat, but DID label duct epithelial cells.

PNA (*Arachis hypogaea*, Peanut Agglutinin) was obtained from Vector Laboratories., FITC-conjugated (Cat.# FL-1071) and used at 1:250–500 dilution.

Paraffin sections of adult human pancreas were obtained from Carolina Biological Supply.

Protocol for Histochemistry:

Paraffin sections of adult human pancreas, adult rat pancreas, embryonic rat pancreas, or cryosections of adult mouse pancreas were used. Alternatively, Time 0 duct or cultured duct preparations from 2 week old rat pancreas were examined, with or without paraformaldehyde fixation. PNA-FITC was used usually at 1:250 dilution in PBS or DMEM/HEPES medium and incubated for 1 hr to overnight at 4° C., then washed and mounted under VectaShield mounting medium containing DAPI. Cells stained without prior fixation were post-fixed before addition of mounting medium.

Protocol for FACS:

PNA-FITC was diluted 1:250 in sterile wash buffer (Ca++ Mg++-free PBS containing 1% FBS). Dispersed live cells (approx. 2×106 cells) were spun down and resuspended in 100 µl of lectin and incubated for 30–45 min at 4° C. Cells were then washed twice with sterile wash buffer, resuspended in 2 ml of Iscoveis modified DMEM containing 5% FBS, Pen/Strep, 1 mM glutamine, and held on ice until run on the FACSVantage. Standard FACS procedures were used.

FACS sorted cells were collected into tubes or delivered directly into multiwell culture plates containing complete Iscoveis medium (see above). Cell density at seeding, surface, substrates, and culture times were varied. Some cultures were re-analyzed by FACS, and some were analyzed by histochemistry.

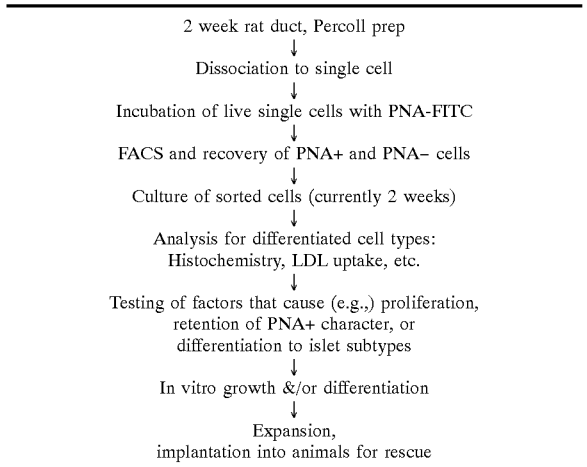

Using PNA, we made the following observations:
  (i) PNA as a marker for Epithelial Cells. PNA marks the single layer of epithelial cells in the pancreatic duct. It does NOT mark islet cells in rat, in contrast to the report in the literature of beta cell marking in porcine islets. It does not mark blood vessels or stromal cells, by immunohistochemistry. PNA marks the epithelial cells of pancreatic duct in adult animals as well as the epithelial sheet in embryogenesis (shown at stages e15, e16 and e18 in rat).
  (ii) PNA labels cell surfaces.
  (iii) PNA labels live, unfixed, unpermeabilized cells.
  (iv) PNA does not mark the major pancreatic duct (common bile duct, CBD). PNA marks primarily the medium-sized interlobular ducts and many of the larger intralobular ducts.
  (v) PNA is a suitable reagent for Fluorescence Activated Cell Sorting. PNA allows a viable cell sorting and recovery by FACS (Becton Dickinson FACSVantage); PNA-positive cells can be sorted directly into multiwell plates. We have applied PNA labeling to RIN, islet cells, T0 duct, and cultured duct monolayers. Approximately 5–15% of a T0 duct prep is PNA-positive by FACS analysis. The percentage does not seem to change very much with culture (over 4 days in FBS). PNA-positive sorted cells are 76–94+% pure upon reanalysis, depending on the selectivity of the sort (events per drop, sort selection mode, etc.). The PNA-negative population is 99+% negative.
  (vi) PNA-sorted cells have favorable Growth Characteristics. Cells are viable but nonadherent after sorting. Dispersed duct cells take a minimum of 7 days to adhere to substrate and begin to grow. In contrast, whole single ducts sit and begin to spread after 24 hr. Cell viability is dependent on plating density in the absence of culture additives. An unsorted population of cells (ıPreSortı) proliferates readily; PNA-positive sorts are slowest. The implication is that other cell types besides the PNA-positive cells are required for maintaining healthy outgrowth, as well as certain cell characteristics (below). PNA-positive cells in culture do not remain PNA-positive (cells restained with PNA-FITC).

A distinct population of cuboidal endothelial-like cells is prominent; also flatter, larger, more fibroblastic cells are present. The former exhibit uptake of DiI-conjugated acetylated-LDL, a characteristic of endothelial cells, while the larger flatter cells do not.

The unsorted and PNA-negative populations grow into cultures of very mixed phenotype and morphologies. A very small percentage of cells in these cultures are diI-Ac-LDL-positive (i.e., endothelial-like).

PNA-positive cells in culture are NOT insulin or PDX-1 positive. Many cells in the mixed PreSort population are positive for both of these beta cell markers. By and large, the strong PDX-positive cells are weak or negative for PNA. Strongly PNA-positive cells are not PDX-positive. This suggests a progression from one cell type to another.

A small number of cells in the PNA-negative cell cultures are positive for Insulin and PDX-1. This suggests either that a small number of PDX+cells (that were PNA-negative) were recovered, or that the presence of the other cell types has activated PDX-1 expression, perhaps from a small carryover of PNA-positive progenitor cells.

PDX-1 expression is much higher (more numerous and relatively brighter) than Insulin expression in these cultured duct preps. Since PDX-1 protein is a regulator of Insulin expression, this finding also suggests a progression, from PDX-1 positive to Insulin-positive.

Glucagon-positive cells outnumber PYY-positive cells, although both are rare in all sort fractions. Previous work has indicated that PYY-positive cells precede appearance of Glucagon cells; thus these results would suggest progenitor cells have already progressed beyond this point.

Based on these findings, we conlude that the ability of PNA to selectively detect pancreatic duct epithelial cells may permit the recovery of a population of cells containing an islet progenitor cell type. These cells in themselves appear to be insufficient to survive and differentiate; that is, other cells or factors may potentiate proliferation and differentiation. Nonetheless, PNA-selection represents a large step forward in being able to perform recombination experiments to identify the components necessary to grow pancreatic islets.

FIGS. 15–17 illustate the phenotype of cells which have been cultured for two weeks after being sorted on the basis of PNA staining.

EXAMPLE 4

Identification of Genotype of Pancreatic Progenitor Cells

In order to improve our technique for isolating pancreatic progenitor cells, we have designed a protocol for determining the identity of a pancreatic beta cell, or it precursor, in terms of its gene expression profile. In general, the method applies single cell cDNA amplification to gene expression analysis. In such a manner, the gene expression "fingerprint" for a cell at a particular stage of development can be obtained by arrayed hybridization.

Briefly, single cells are isolated, e.g., from pancreatic tissue, The cDNA from each cell are amplified by the single cell PCR developed by Brail et al. (1999) *Mutat Res* 406: 45–54, and labelled with $P^{32}$. The cDNAs are then selected for existence of particular messages, e.g., insulin and PDX1.

CDNAs of known pancreatic markers are generated by PCR and arrayed on nylon membranes. The resulting assays are used to hybridize with the labelled single cell cDNAs. The autoradiograph images of the array can be used to define and identify the gene expression profile for an individual cell.

Figure 1:
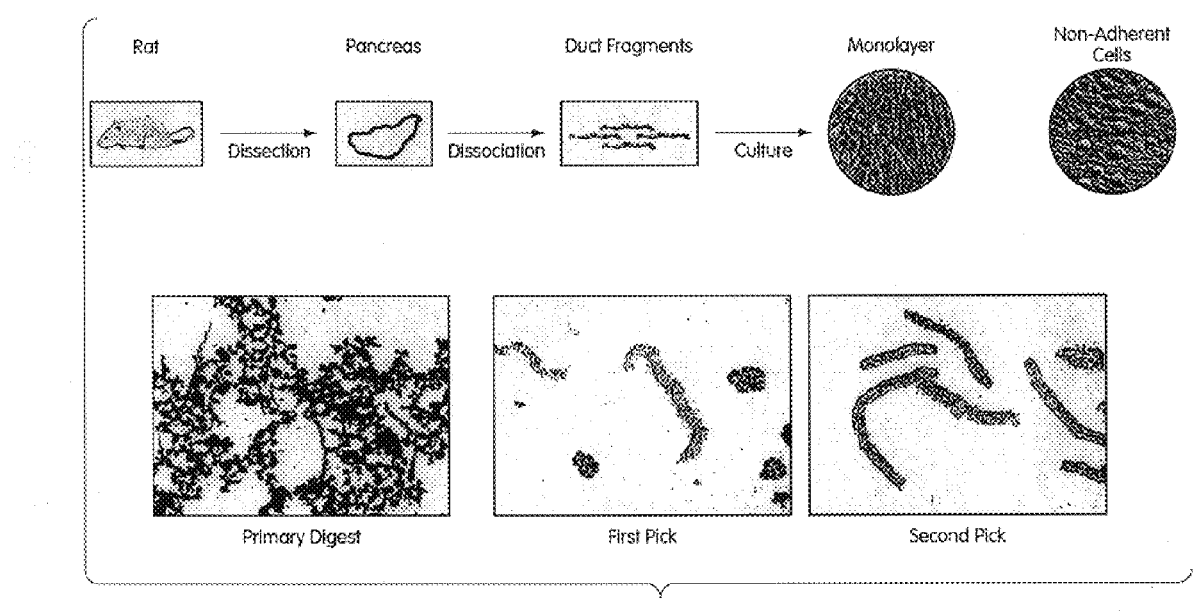
Figure 2:
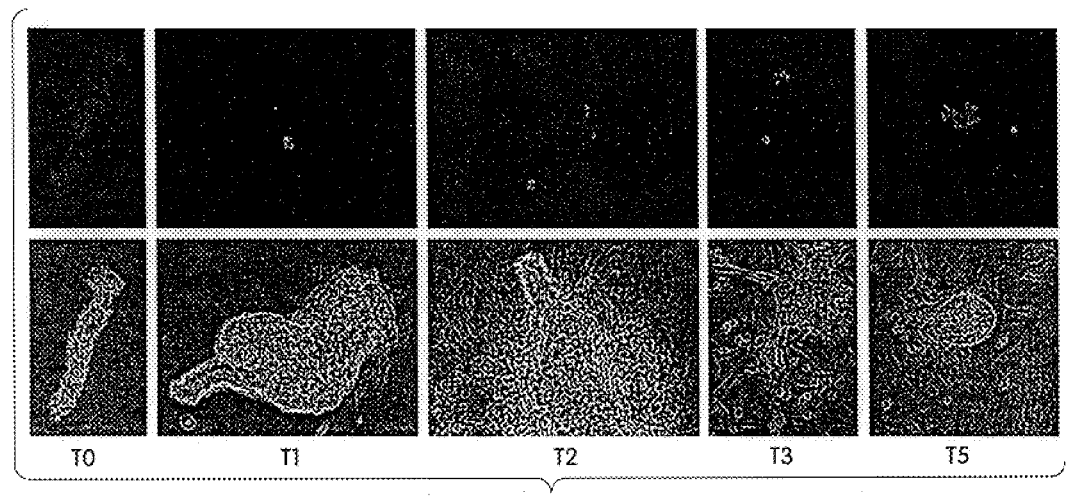
Figure 3A:
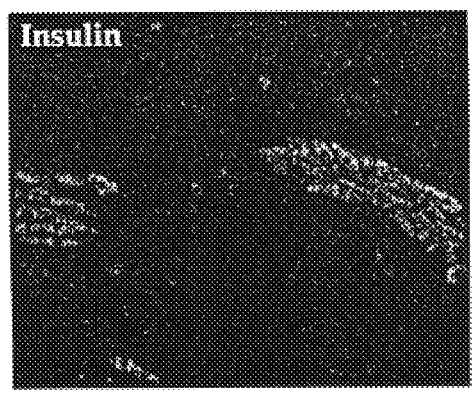
Figure 3B:
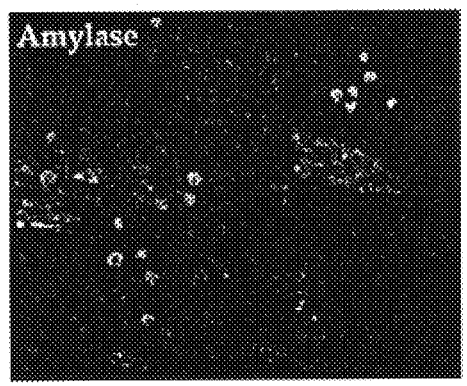
Figure 3C:
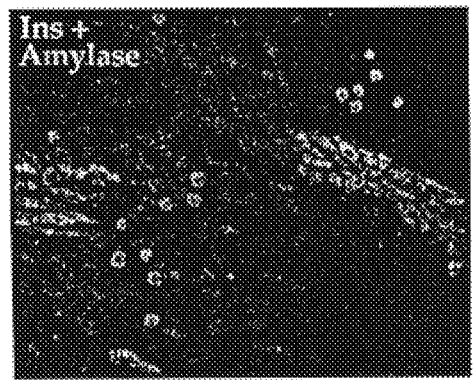
Figure 3D:
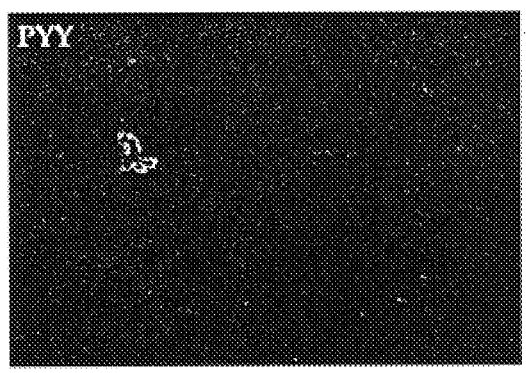
Figure 3E:
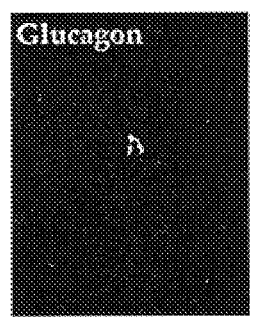
Figure 3F:
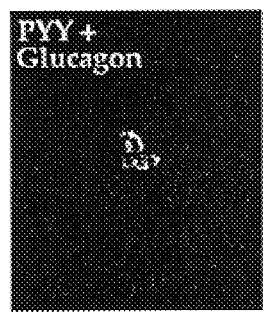
Figure 3G:
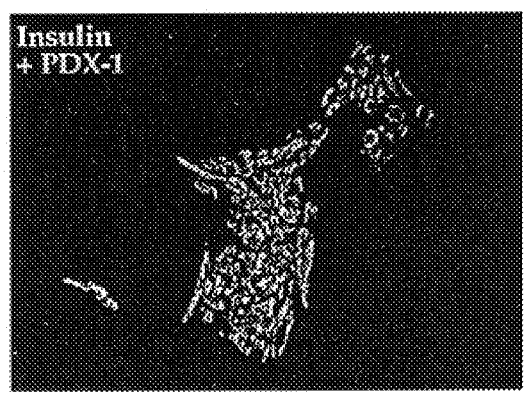
Figure 4A:
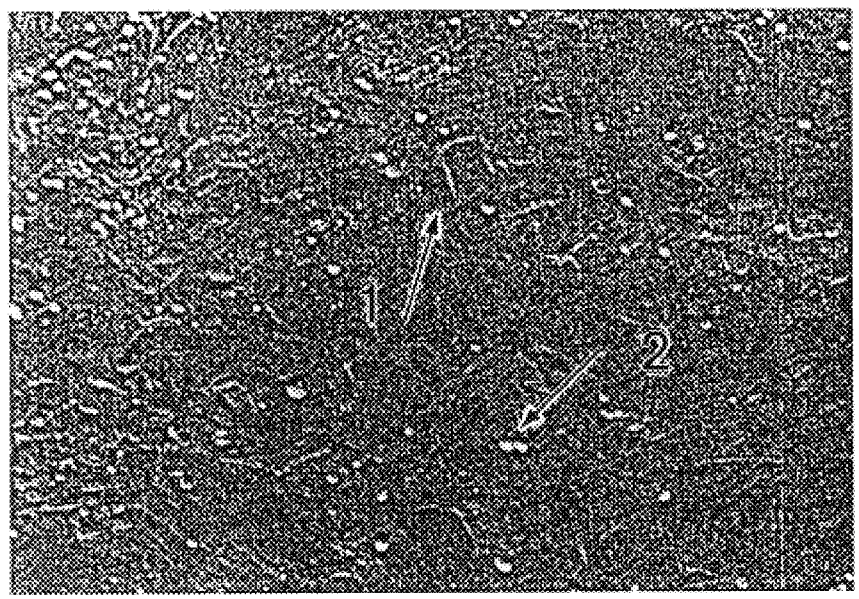
Figure 4B:
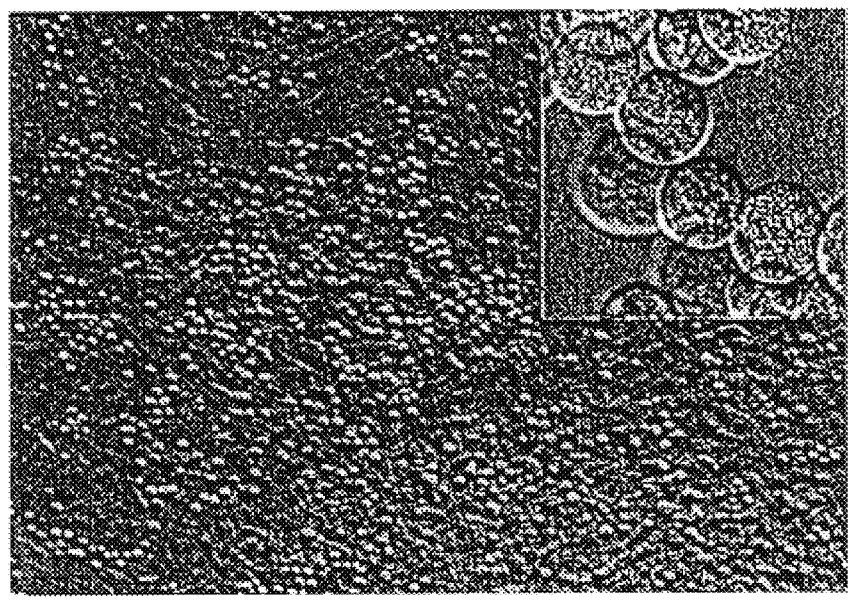
Figure 4C:
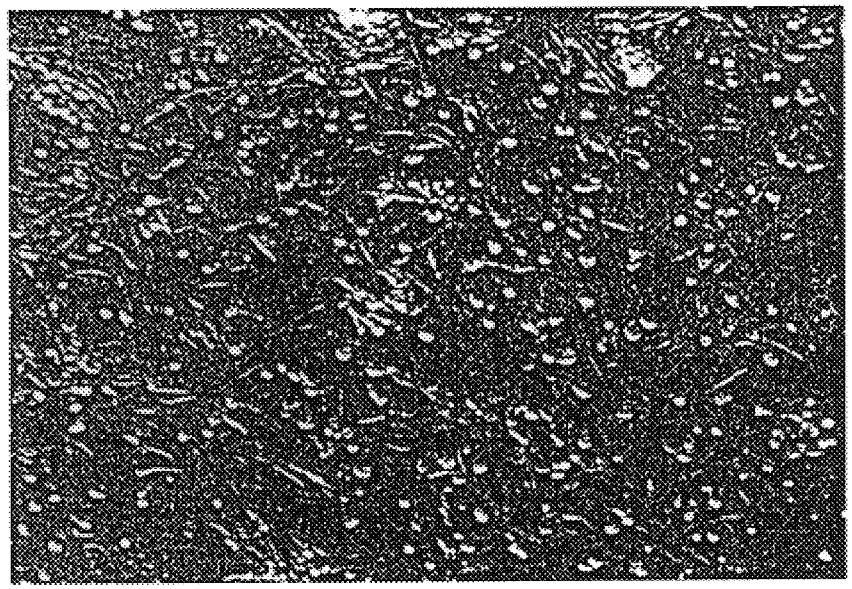
Figure 4D:
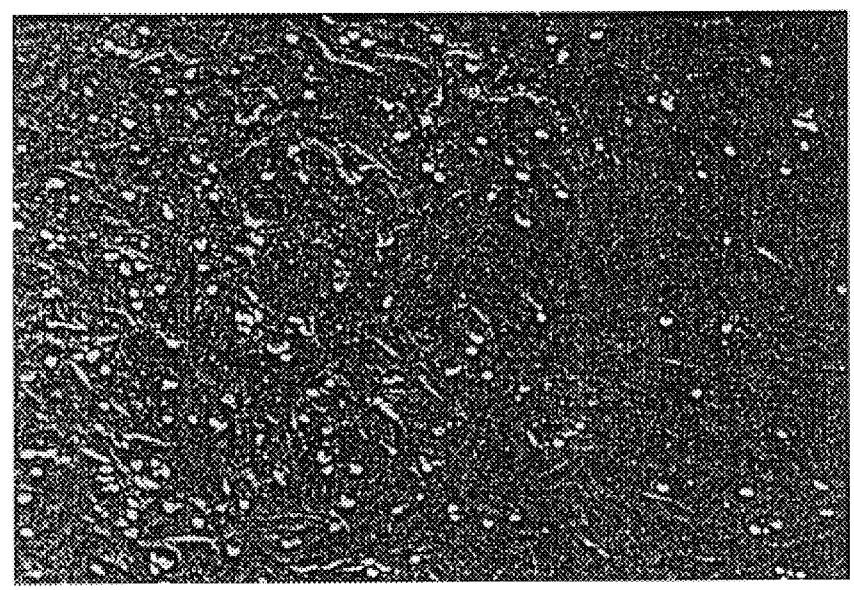
Figure 5A:
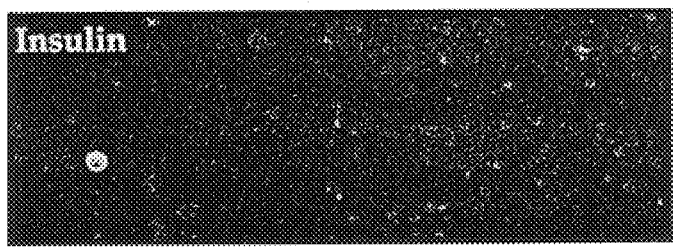
Figure 5B:
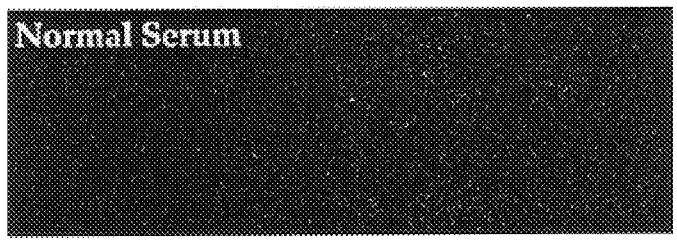
Figure 5C:
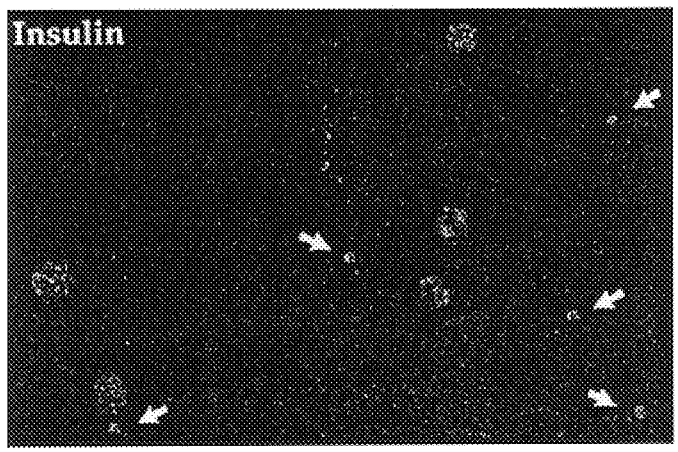
Figure 5D:
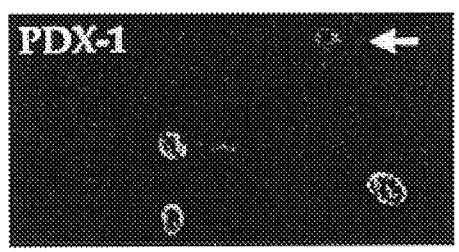
Figure 5E:
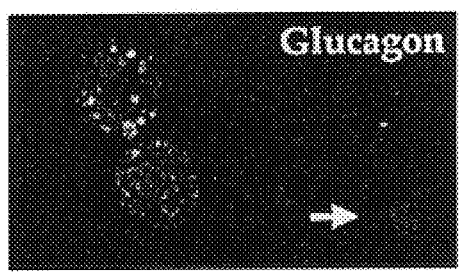
Figure 5F:
Figure 5G:
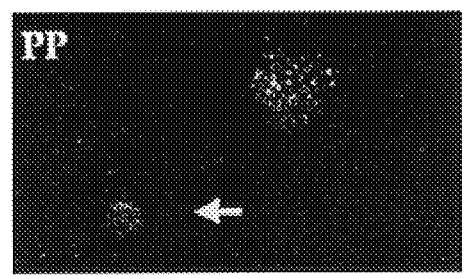
Figure 6A:
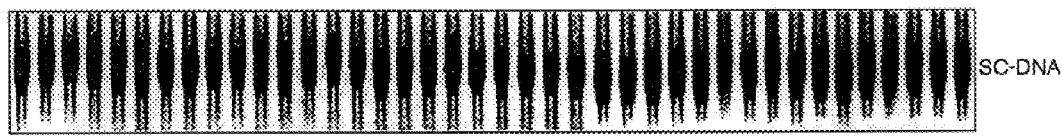
Figure 6B:
Figure 6C:
Figure 6D:
Figure 7:
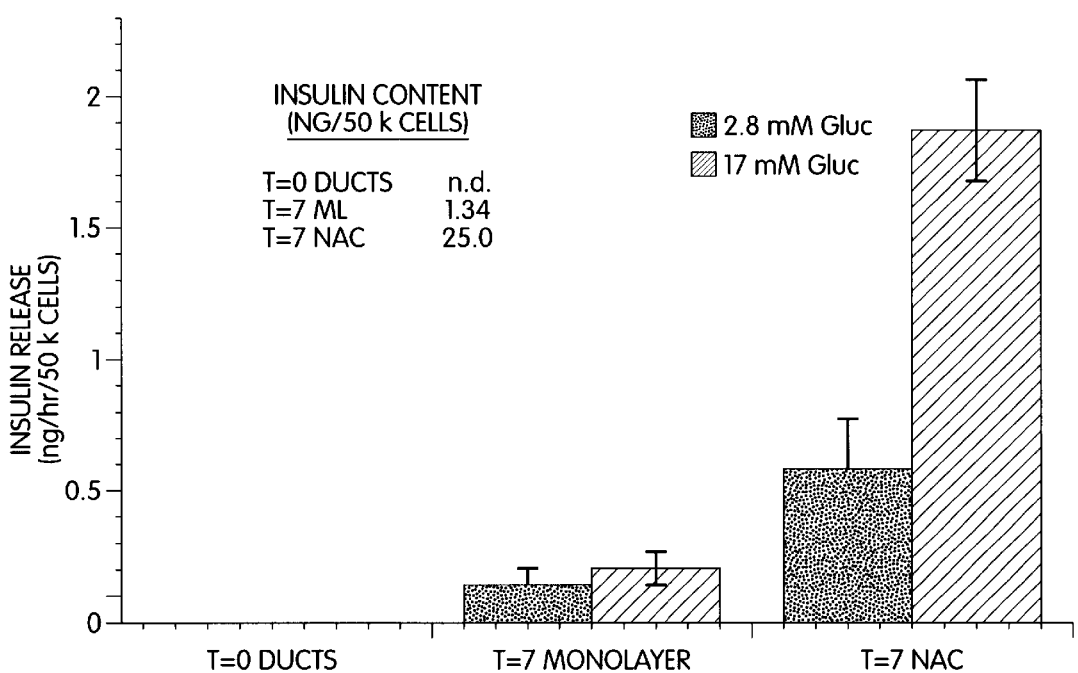
Figure 8A:
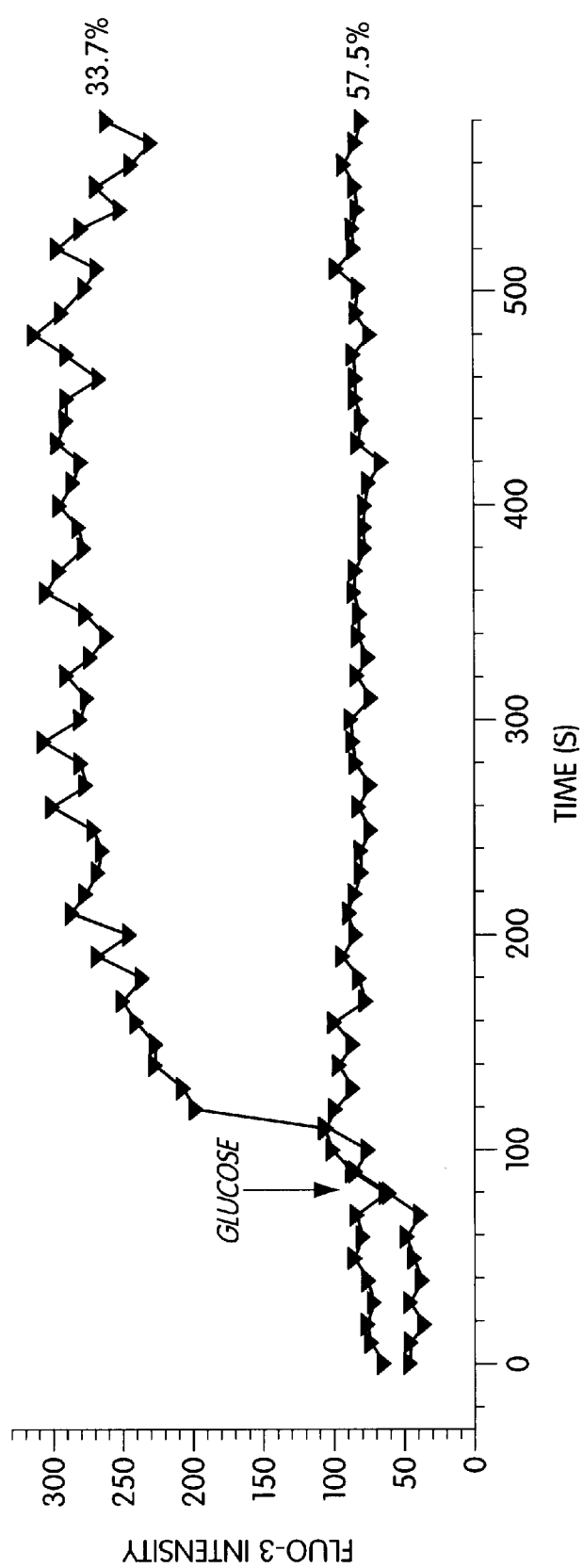
Figure 8B:
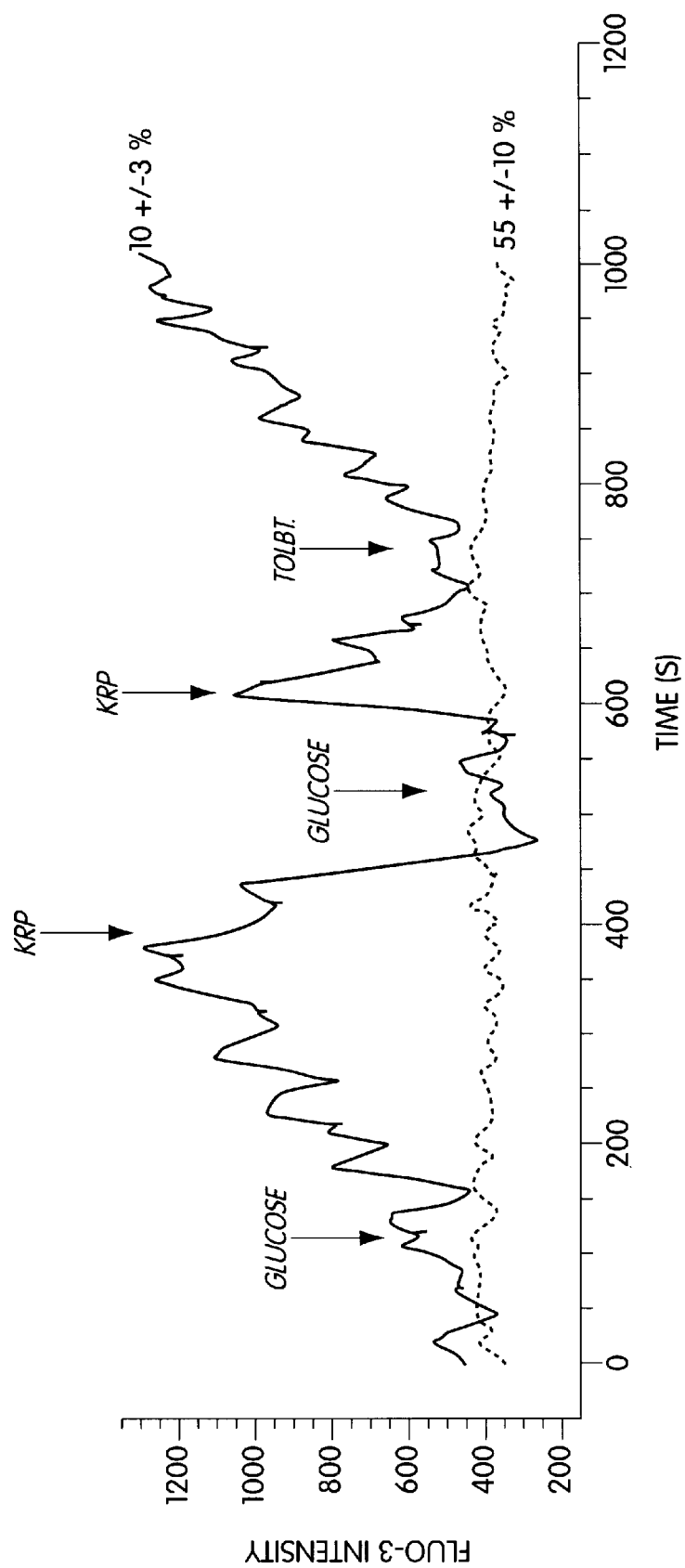
Figure 9:
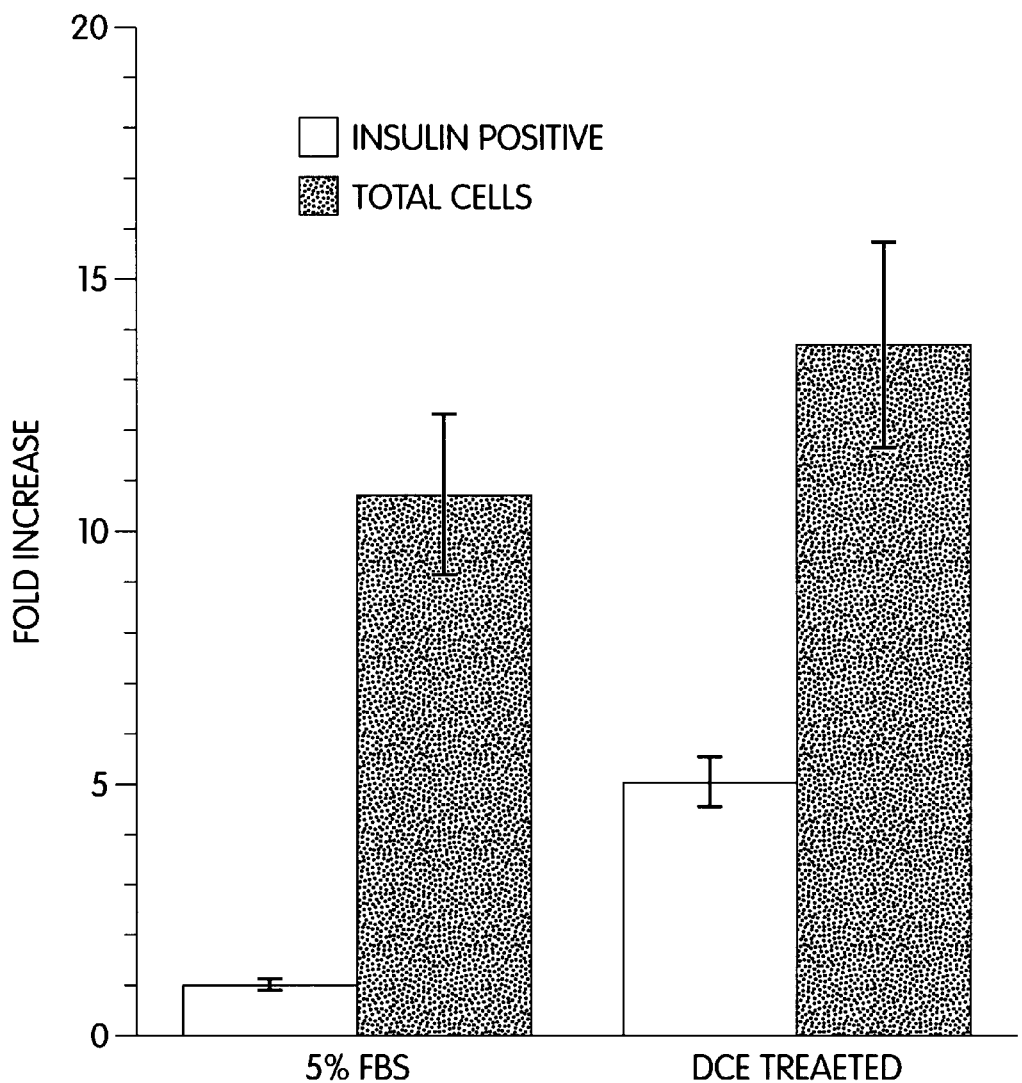
Figure 10:
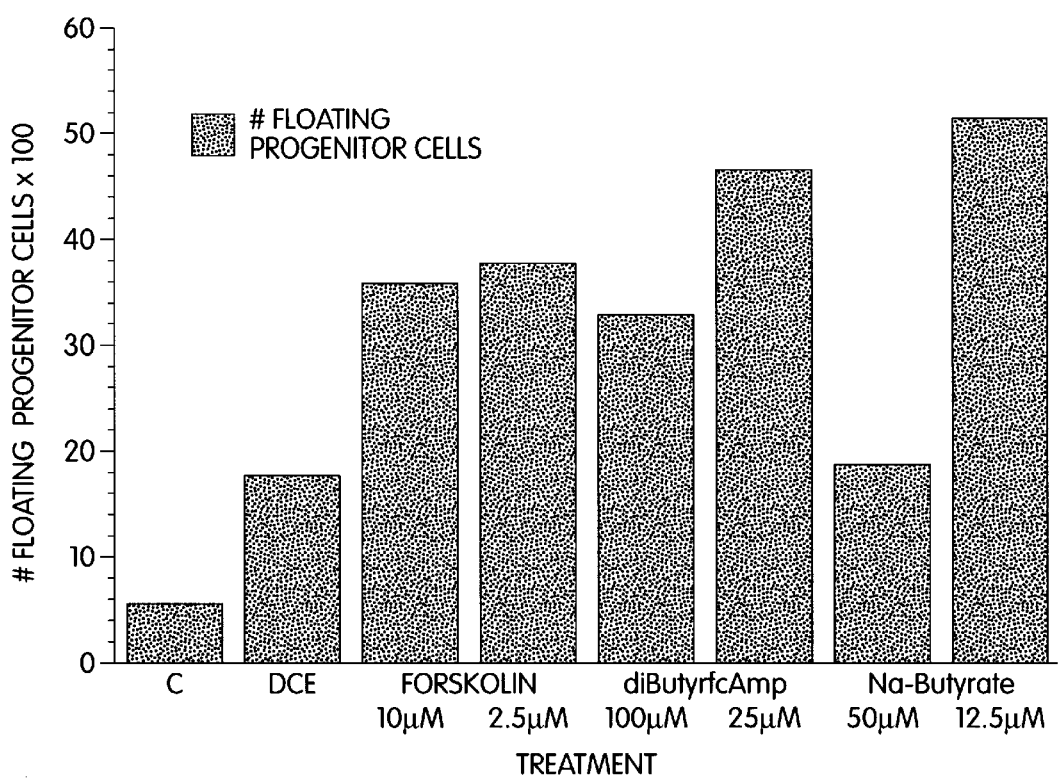
Figure 11:
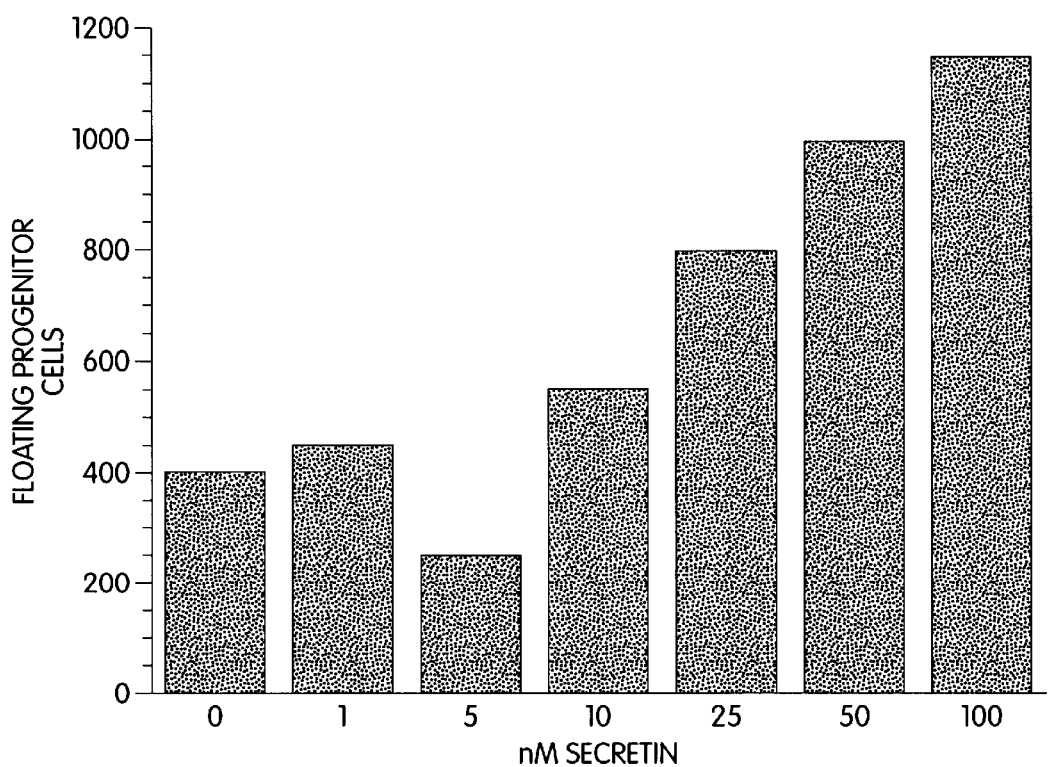
Figure 12:
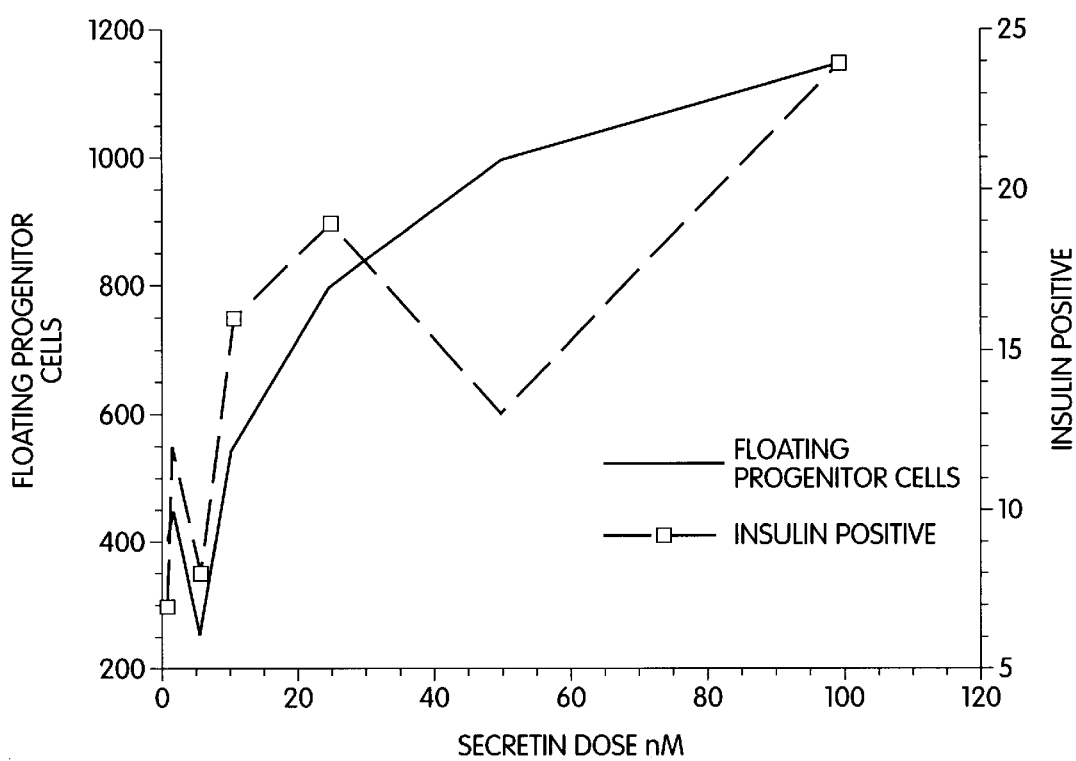
Figure 13:
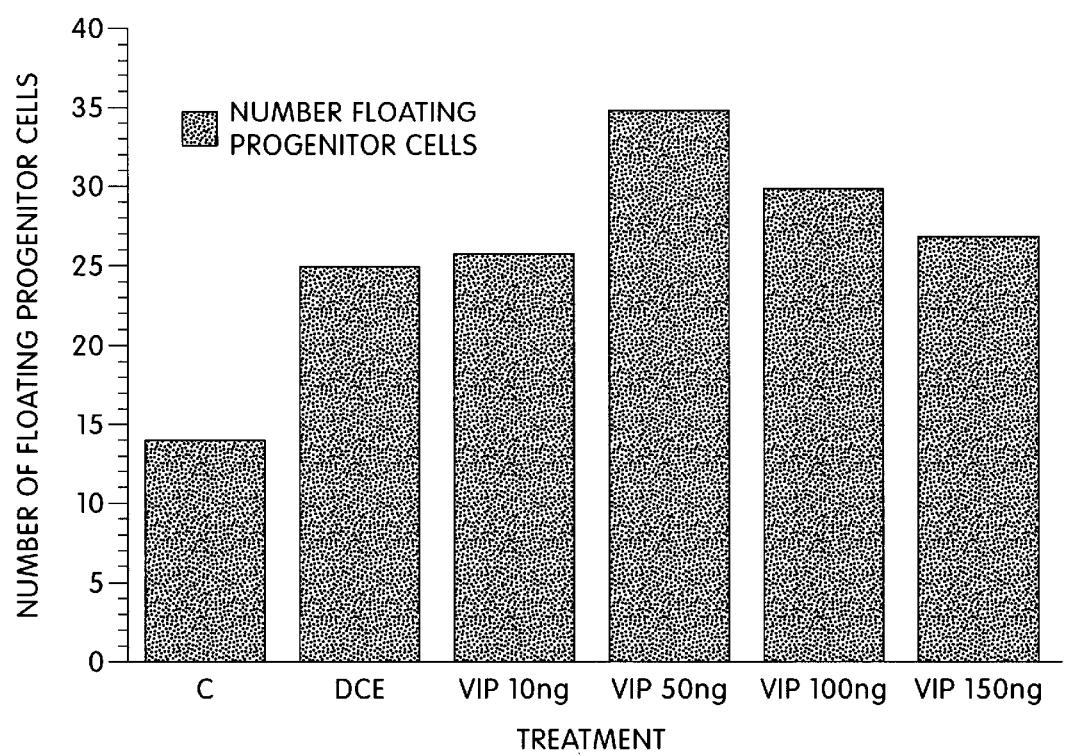
Figure 14:
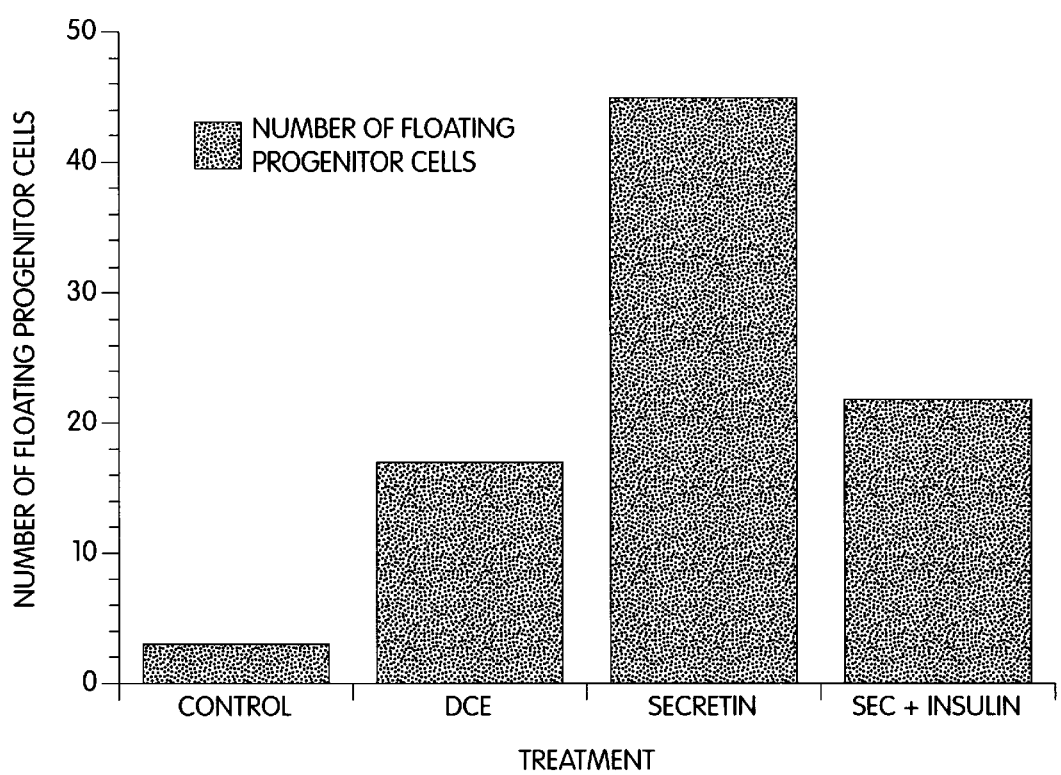
Figure 15:
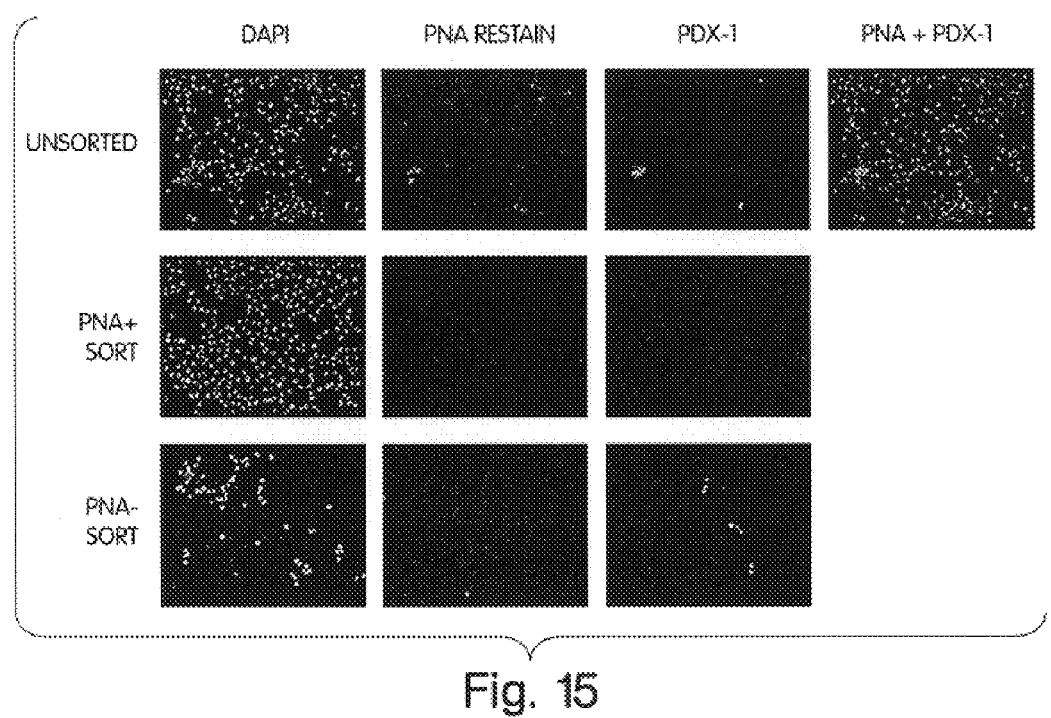
Figure 16:
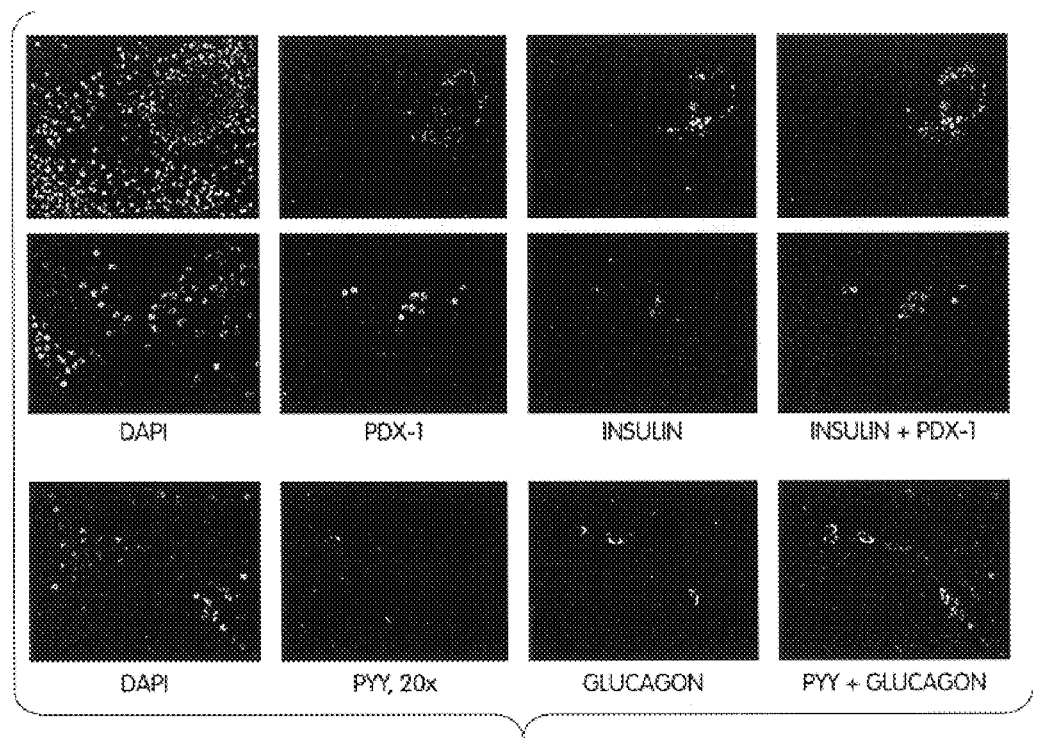
Figure 17:
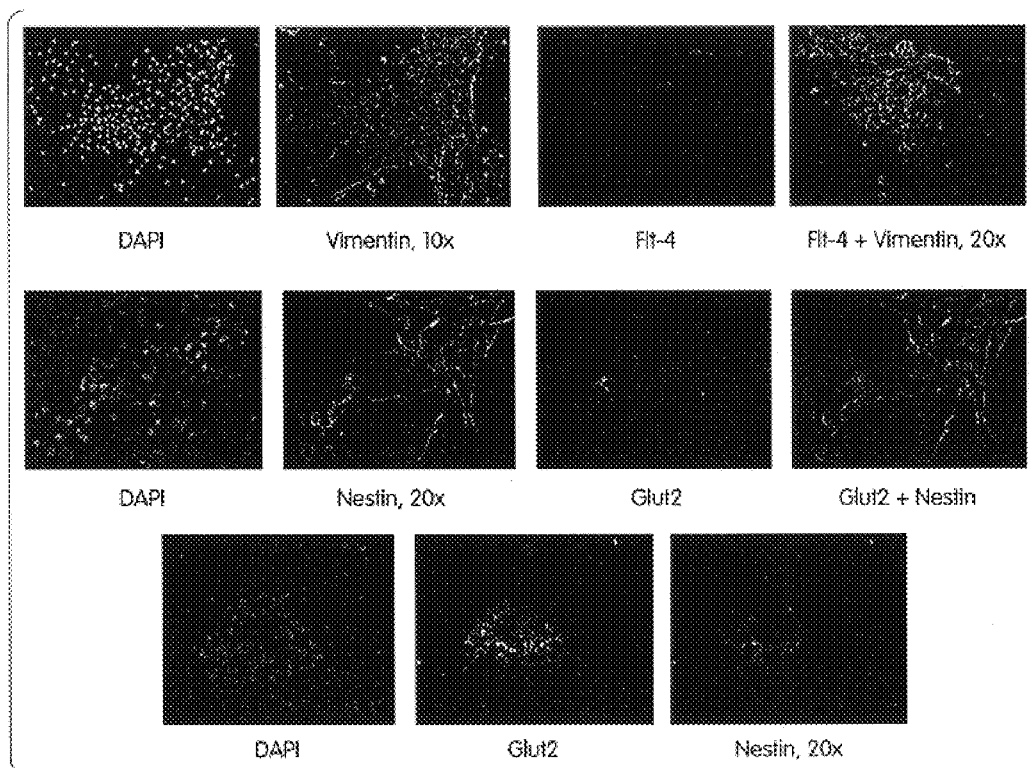
Figure 18:
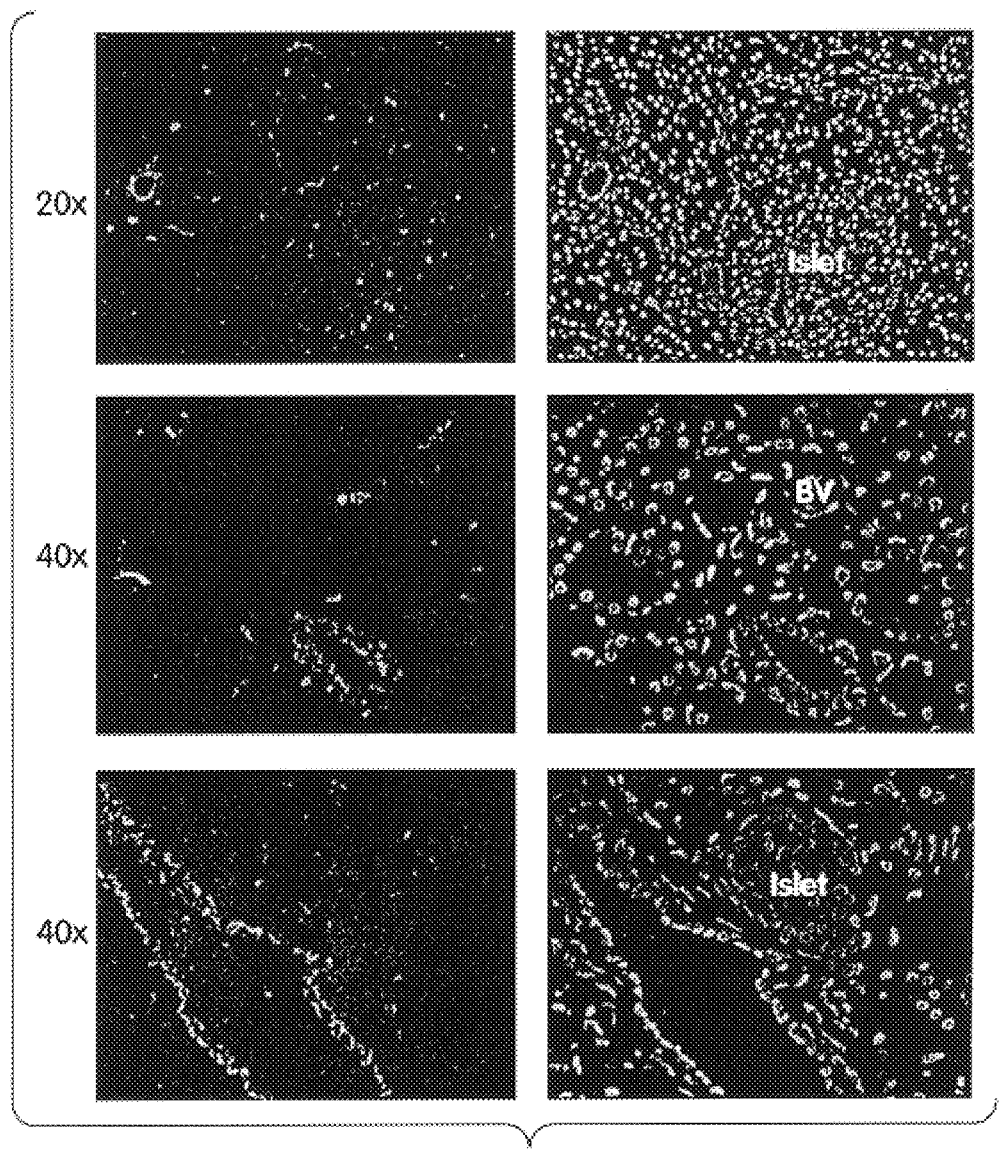
FIGS. 18 and 19 illustrate the specificity of PNA in adult and embryonic pancreas.
Figure 19:
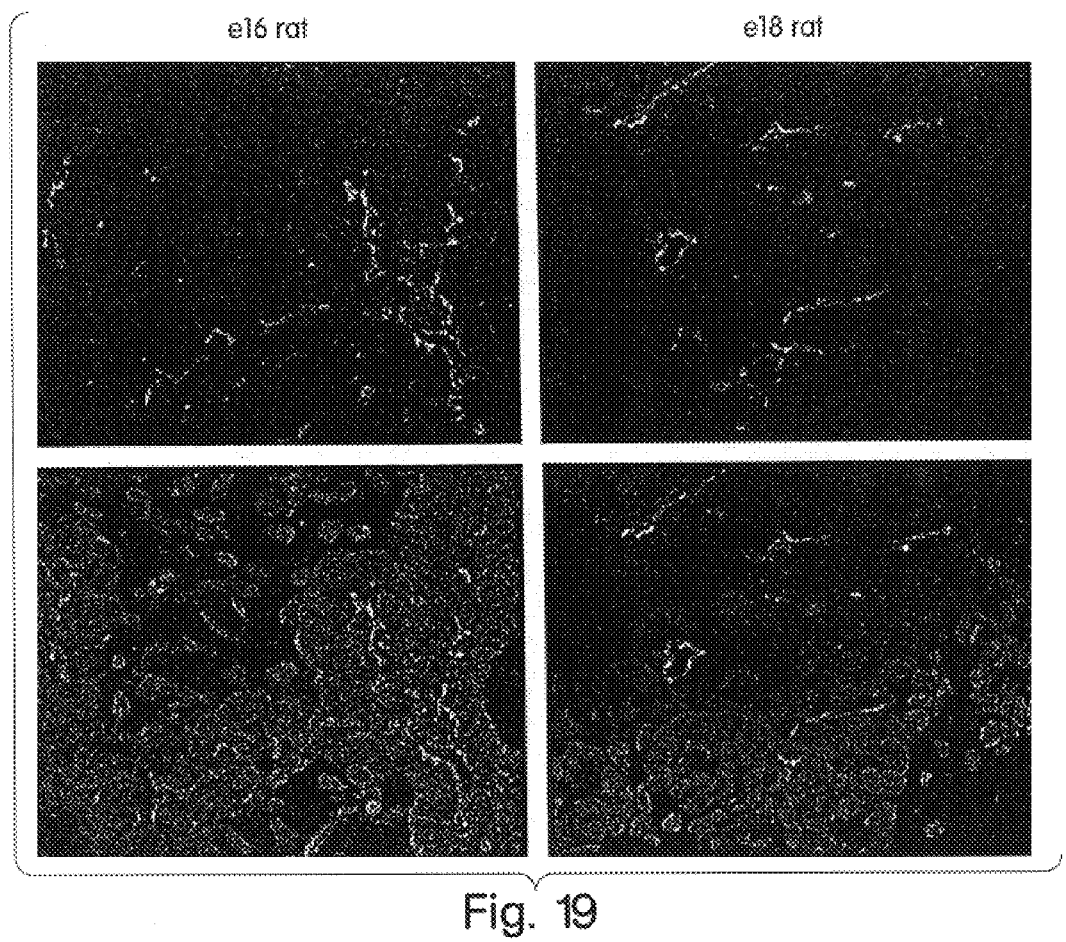
Figure 20:
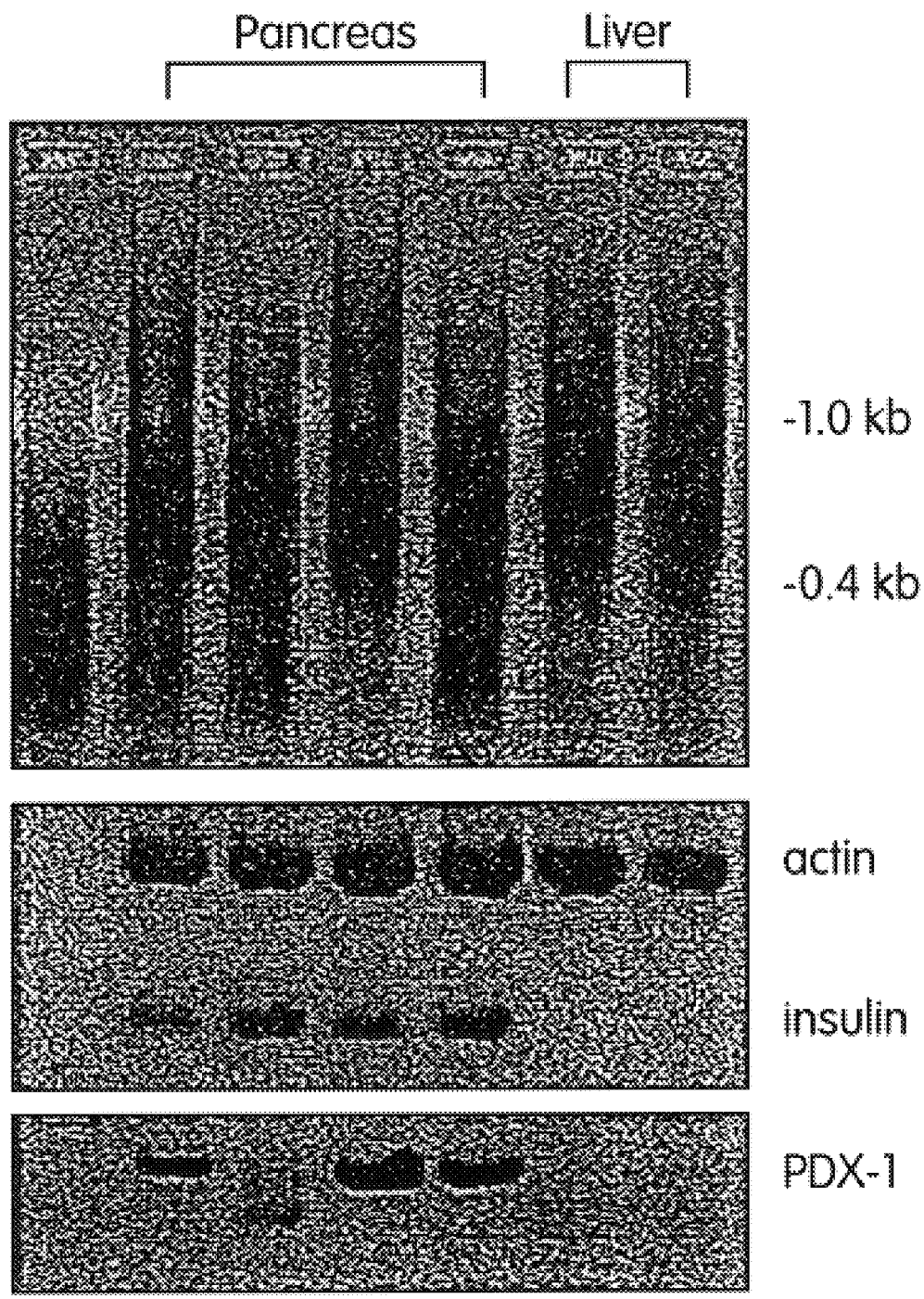

FIGS. 20–29 further illustate the protocol. FIG. 20 shows the results of typical single cell mRNA PCR amplification reactions. FIG. 21 illustrates the changes in the gene expression during pancreatic development, as determined by the subject method. FIG. 22 illustrates one embodiment of an array of markers for detecting beta cells and precursors thereof.

Figure 23:
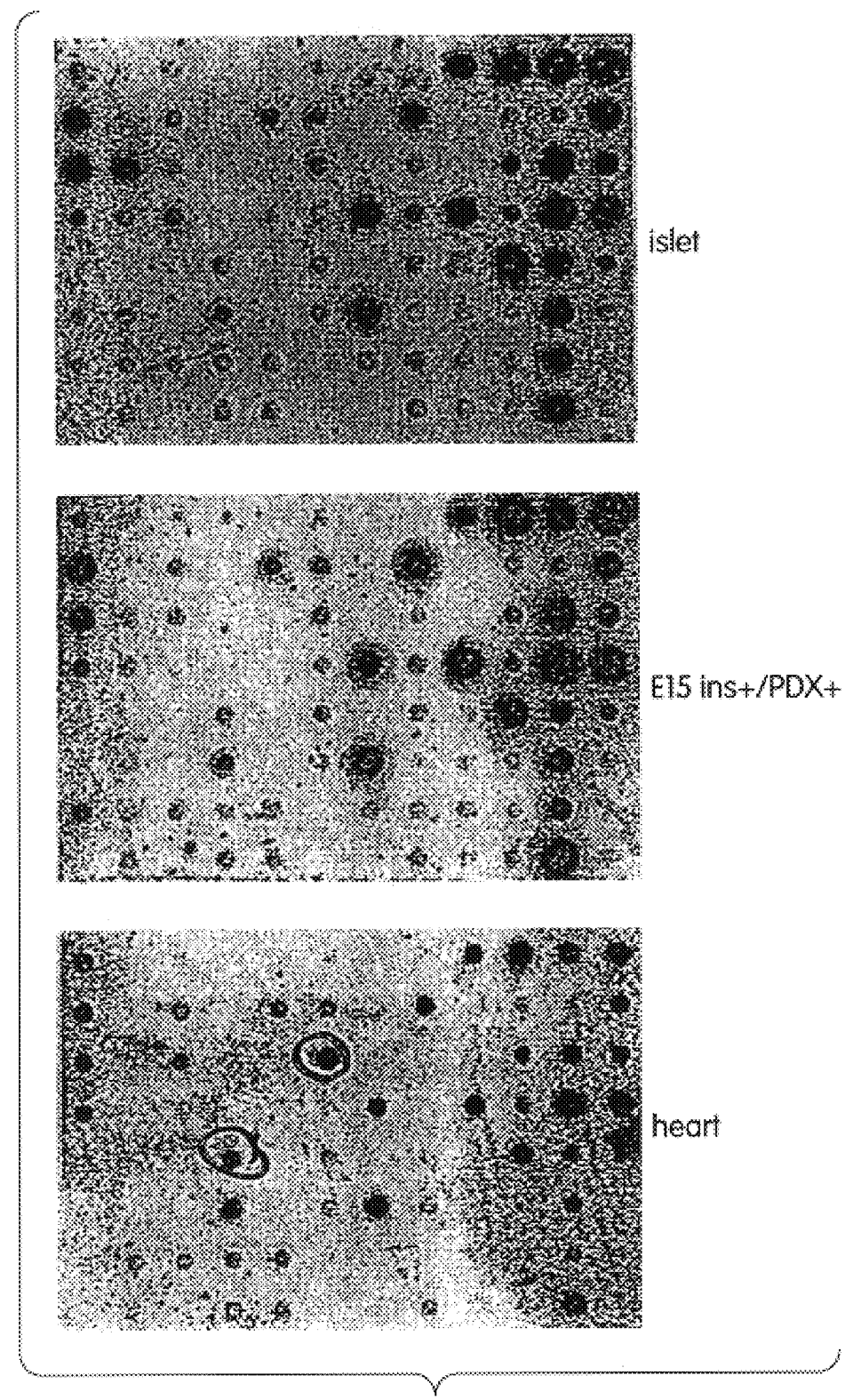
Figure 24A:
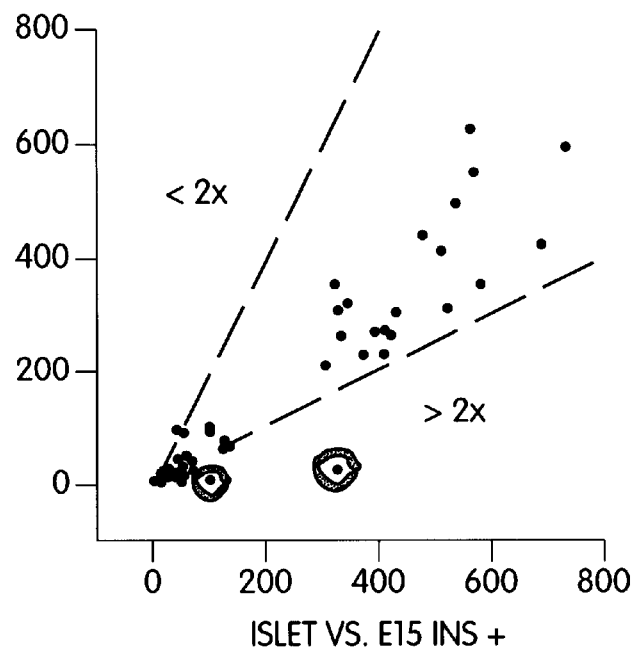
Figure 24B:
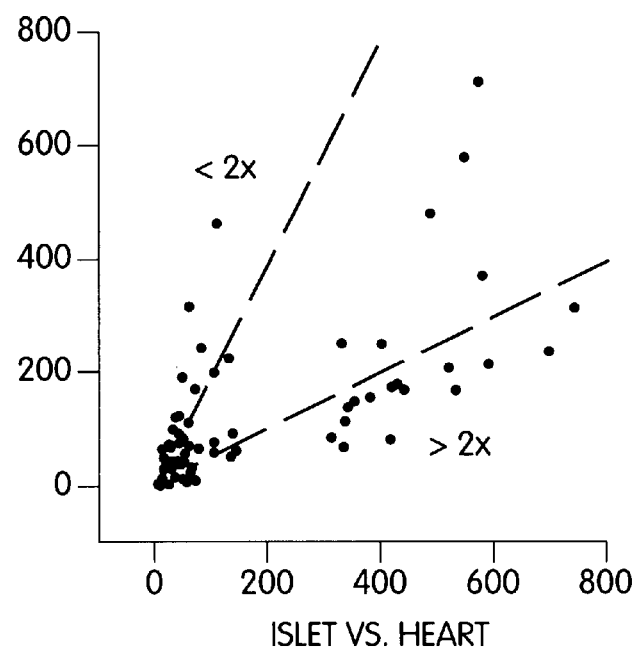
Figure 25:
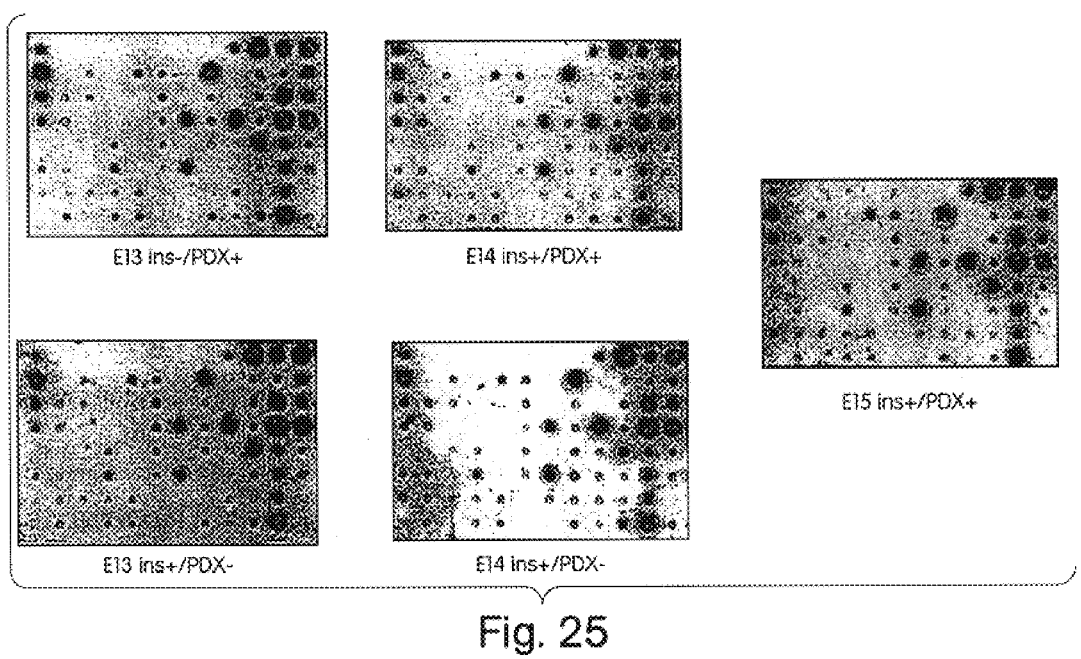
Figure 26A:
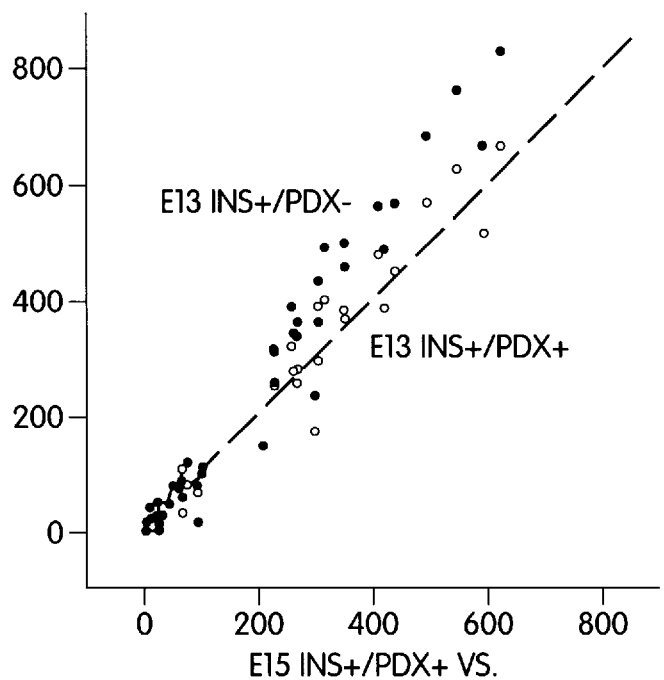
Figure 26B:
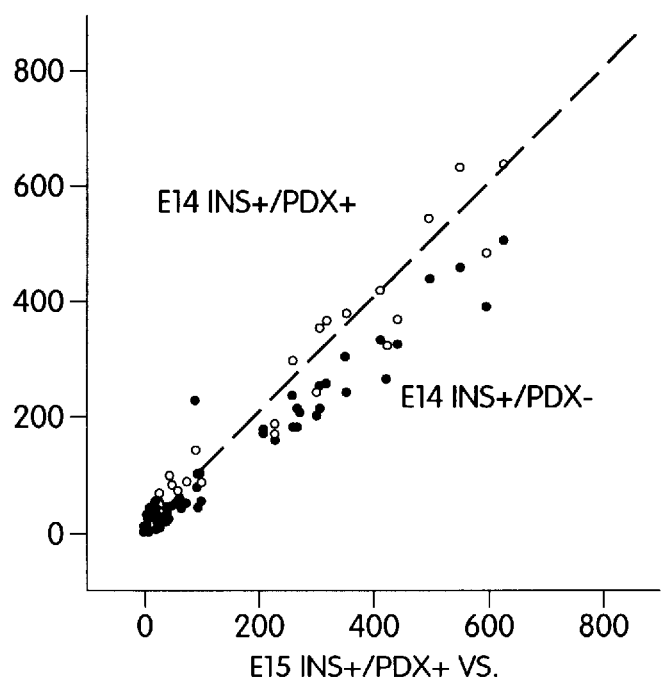

FIG. 23 shows typical autoradiographs profiling gene expression in adult and embryonic pancreatic tissue, and heart. FIG. 24 demonstates how quantatitve analysis of gene expression can be carried out as part of a determination of the gene expression profile of a cell. Likewise, FIG. 25 shows autoradiographs profiling gene expression in embryonic pancreatic tissue at different stages and after different stimulus; FIG. 26 illustate the quantatitve analysis of the autoradiagraphs.

Figure 27:
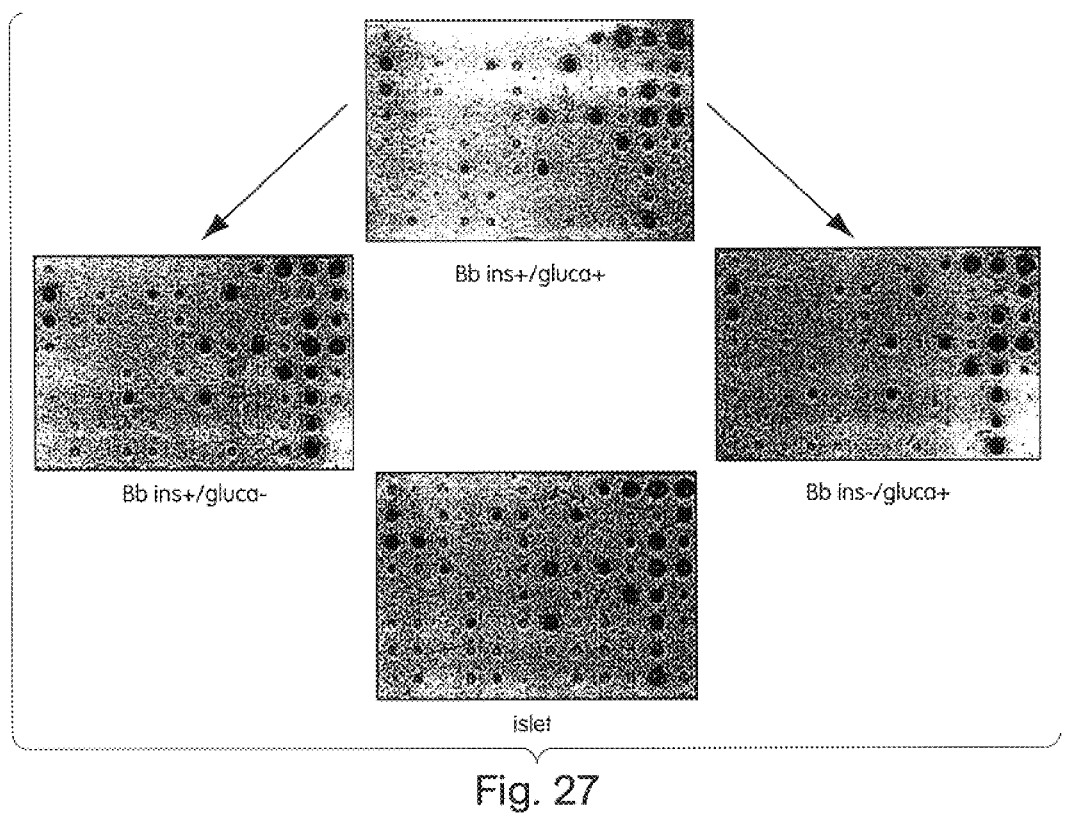
Figure 28A:
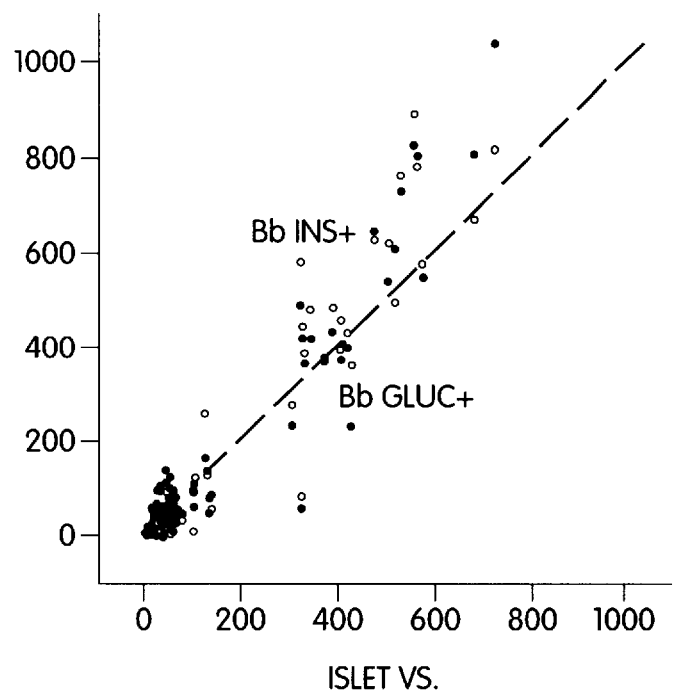
Figure 28B:
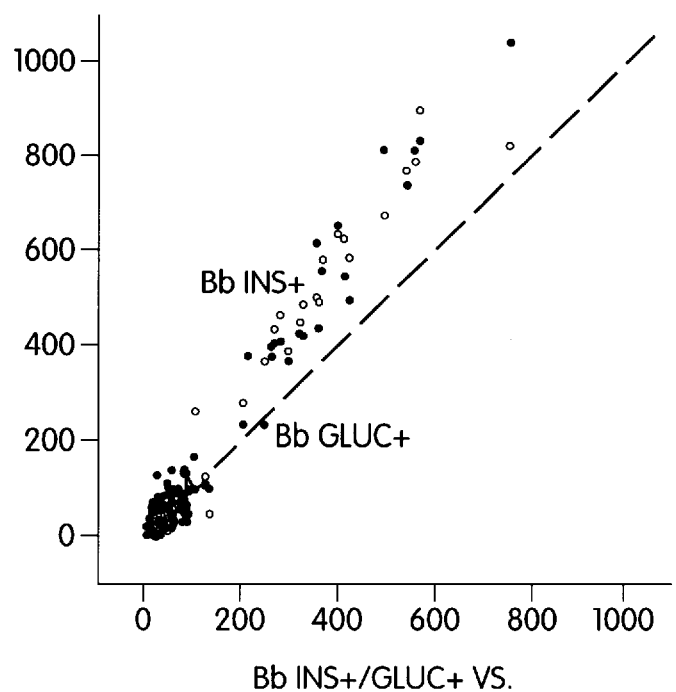
Figure 30:
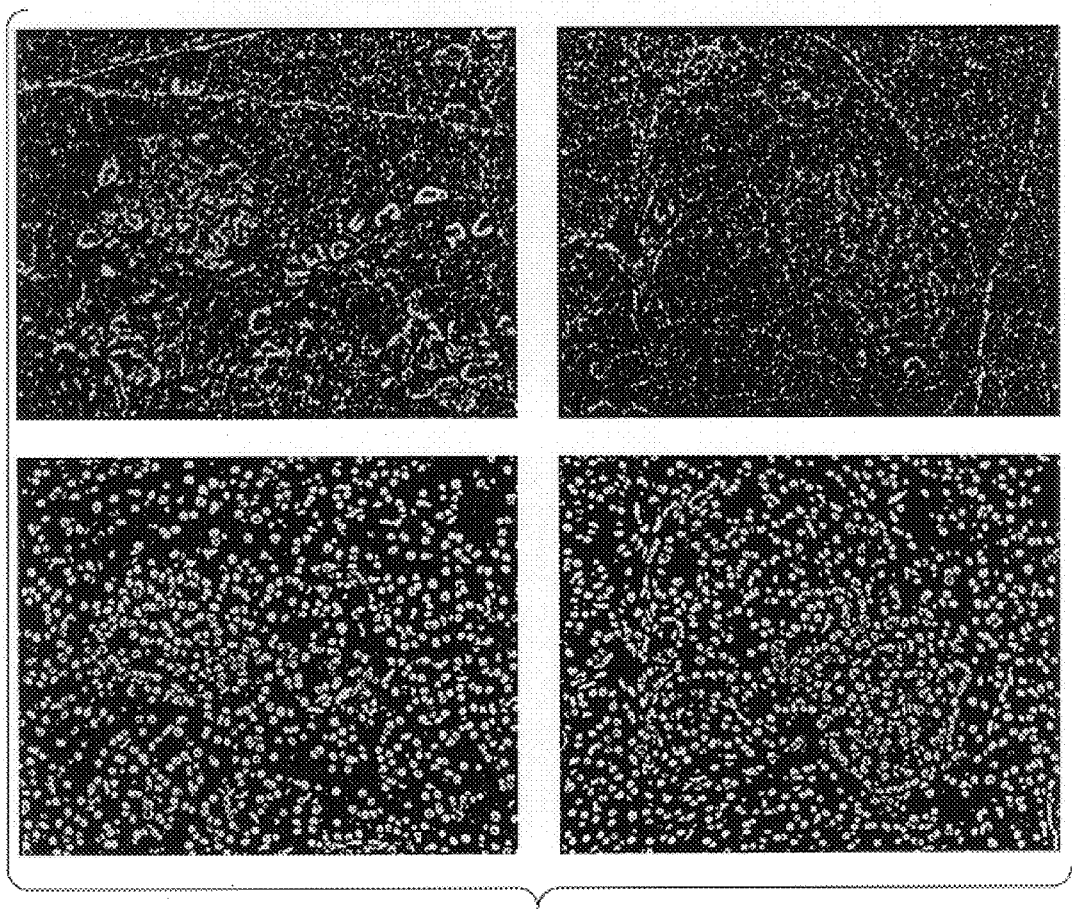
FIGS. 30 and 31 illustrate the binding of other lectins to adult rat pancreas.
Figure 31:
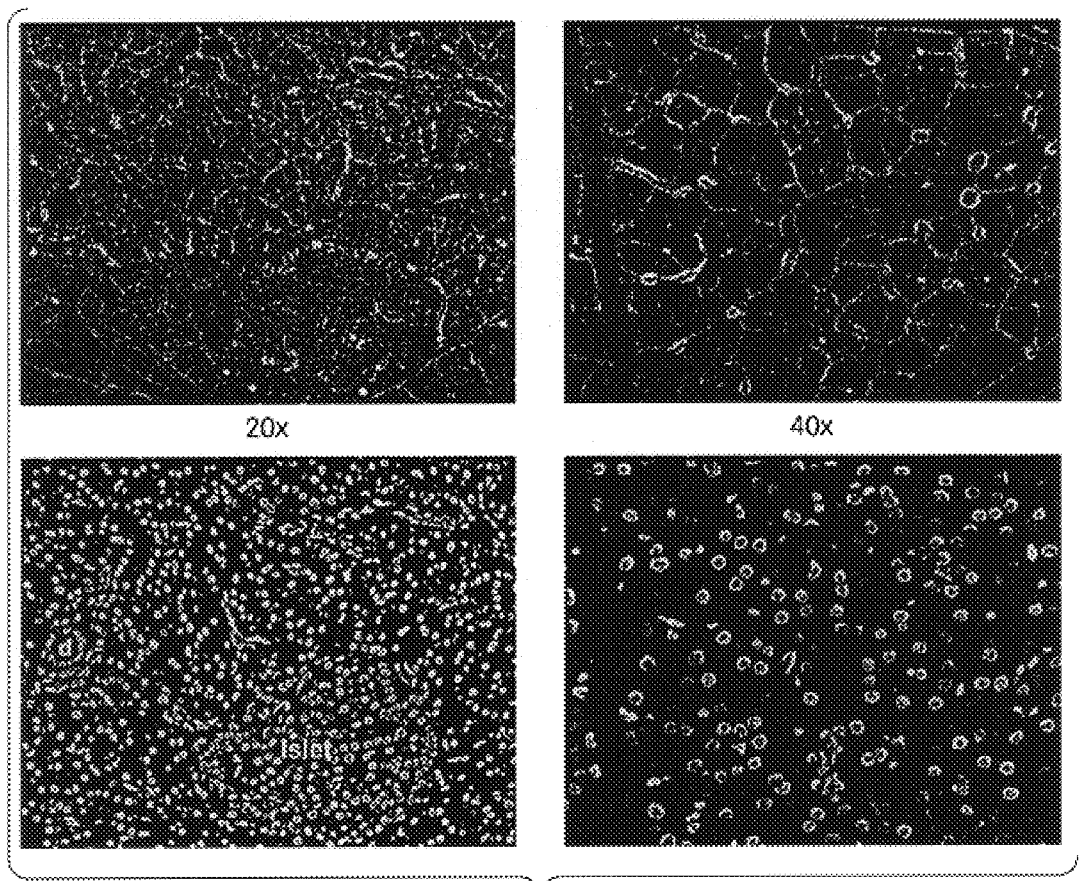
Figure 32:
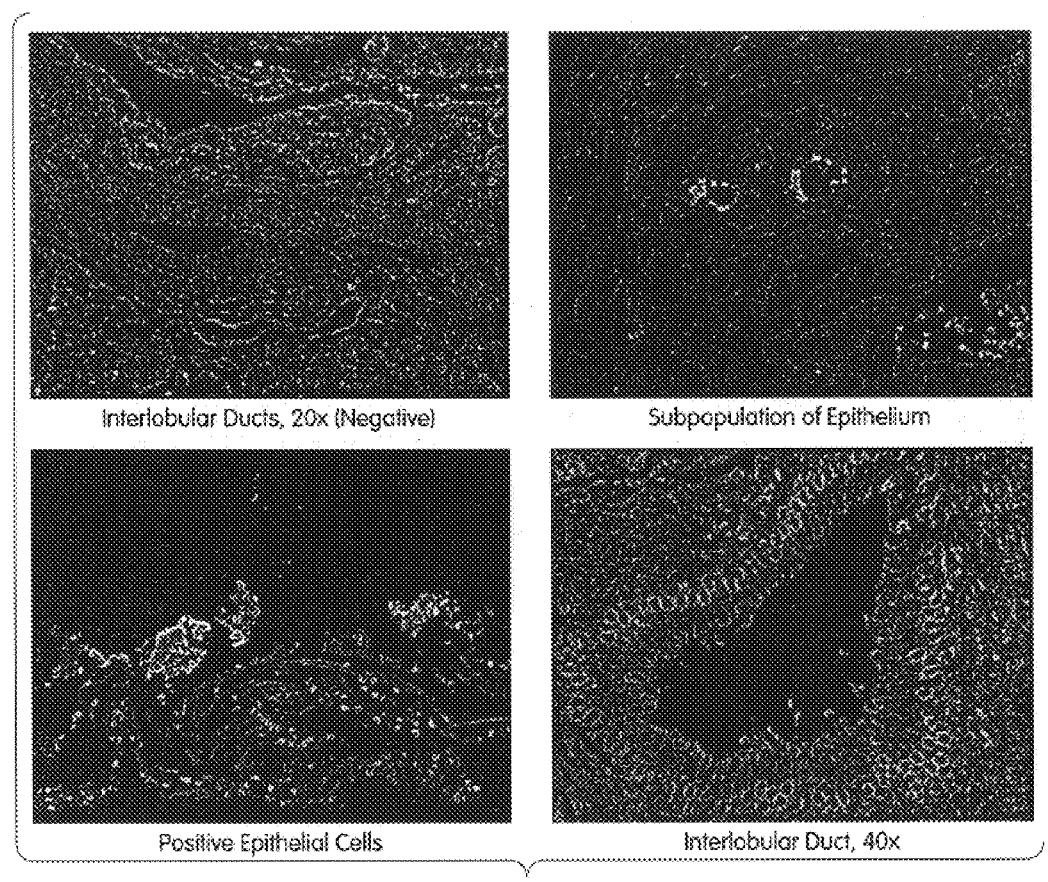
FIGS. 32–39 illustrate the specificity of binding of lectins to adult human pancreas.
Figure 33:
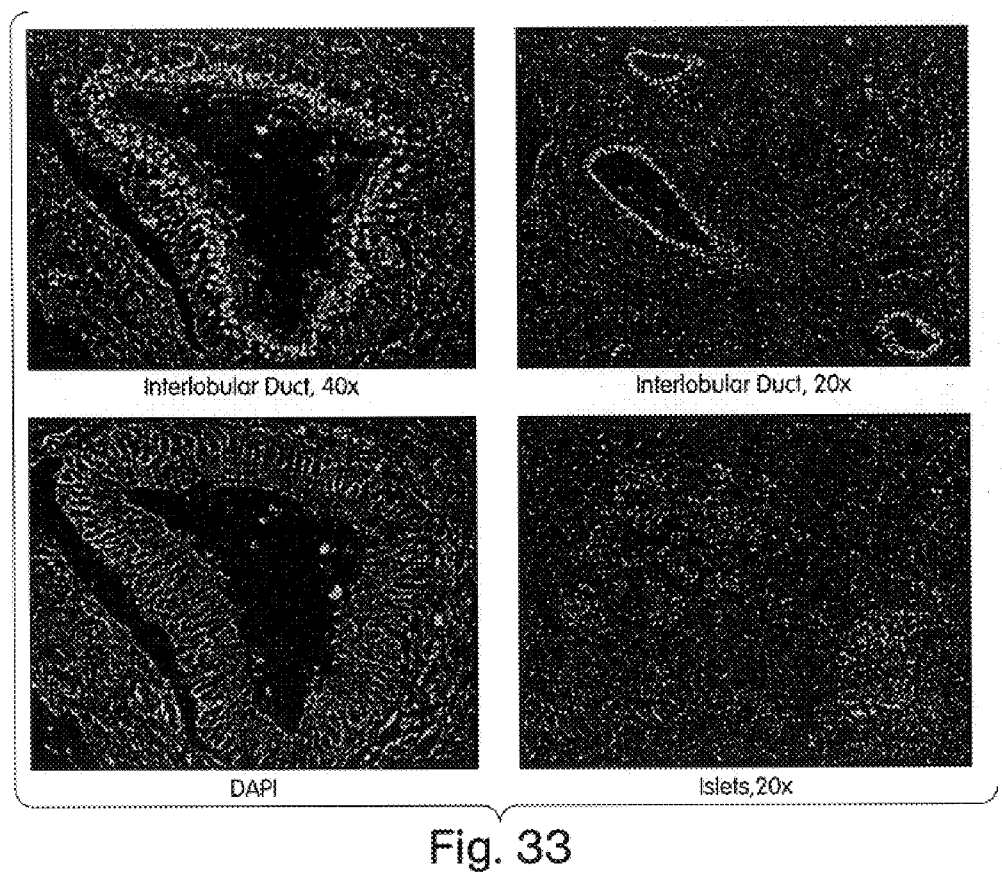
Figure 34:
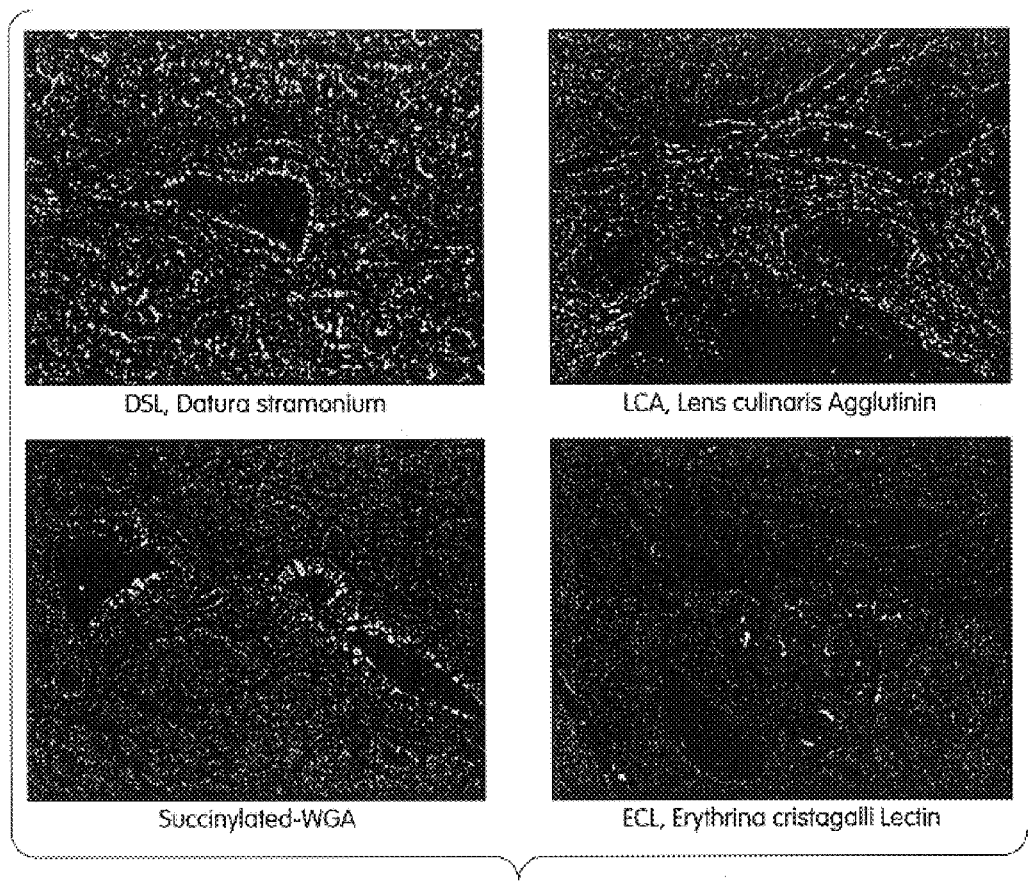
Figure 35:
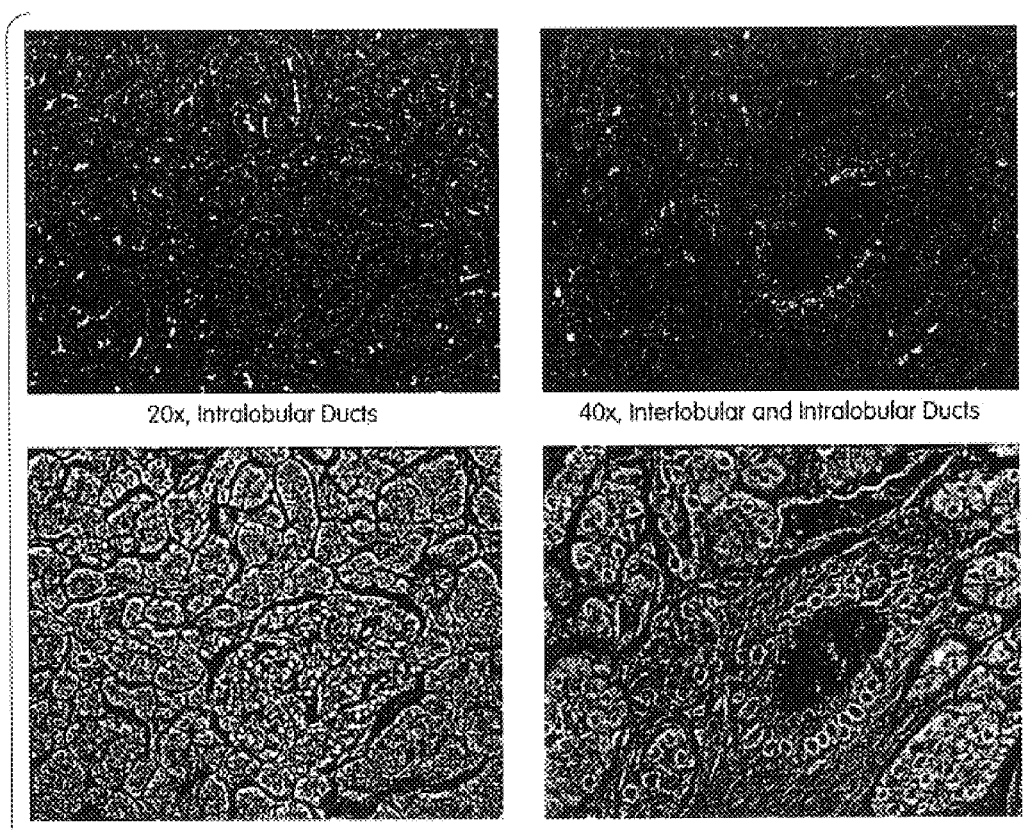
Figure 36:
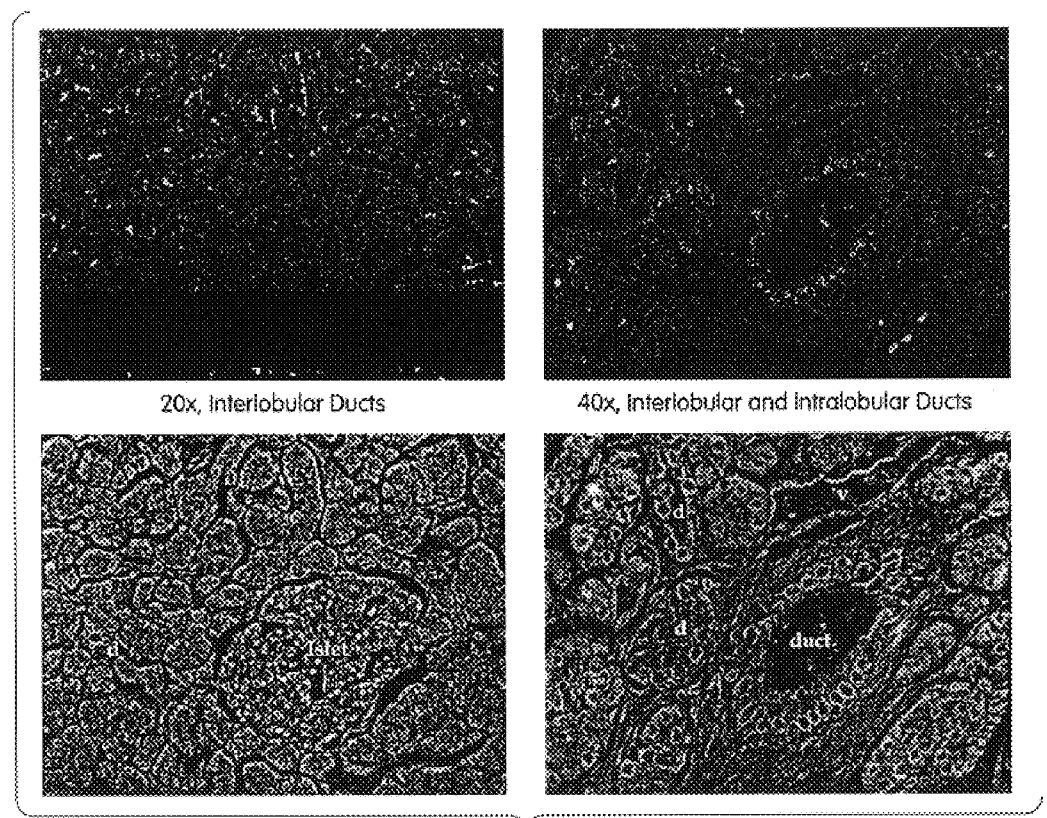
Figure 37:
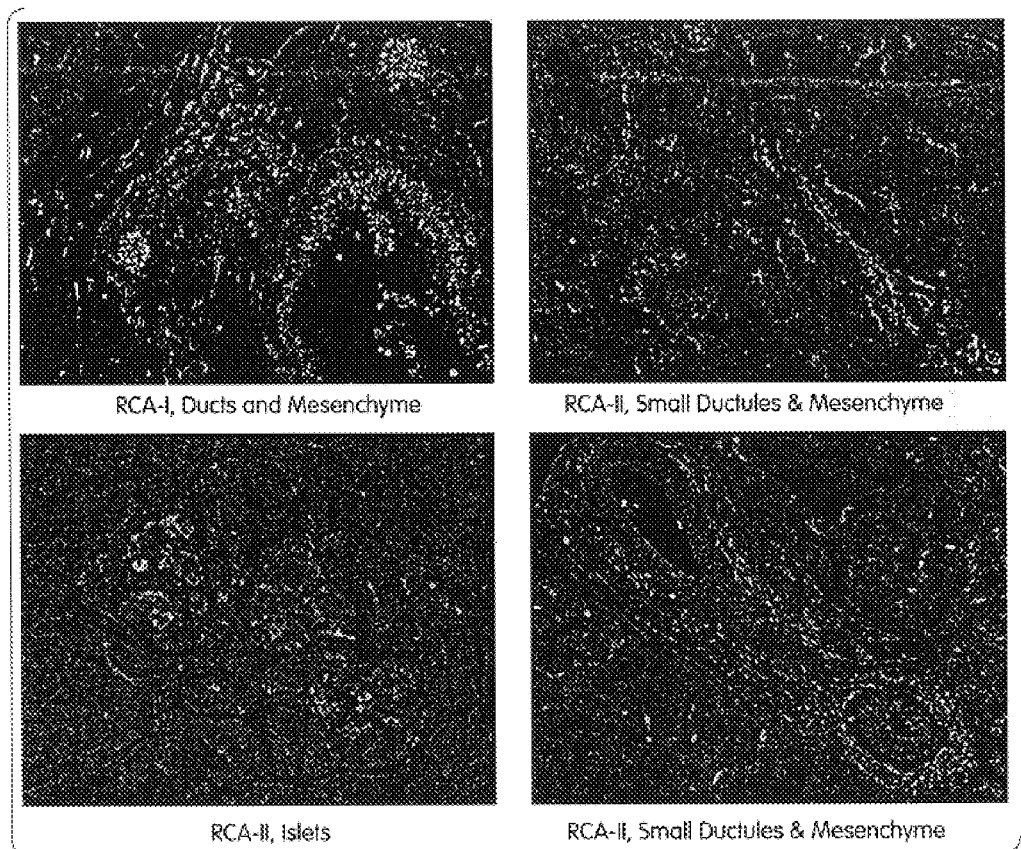
Figure 38:
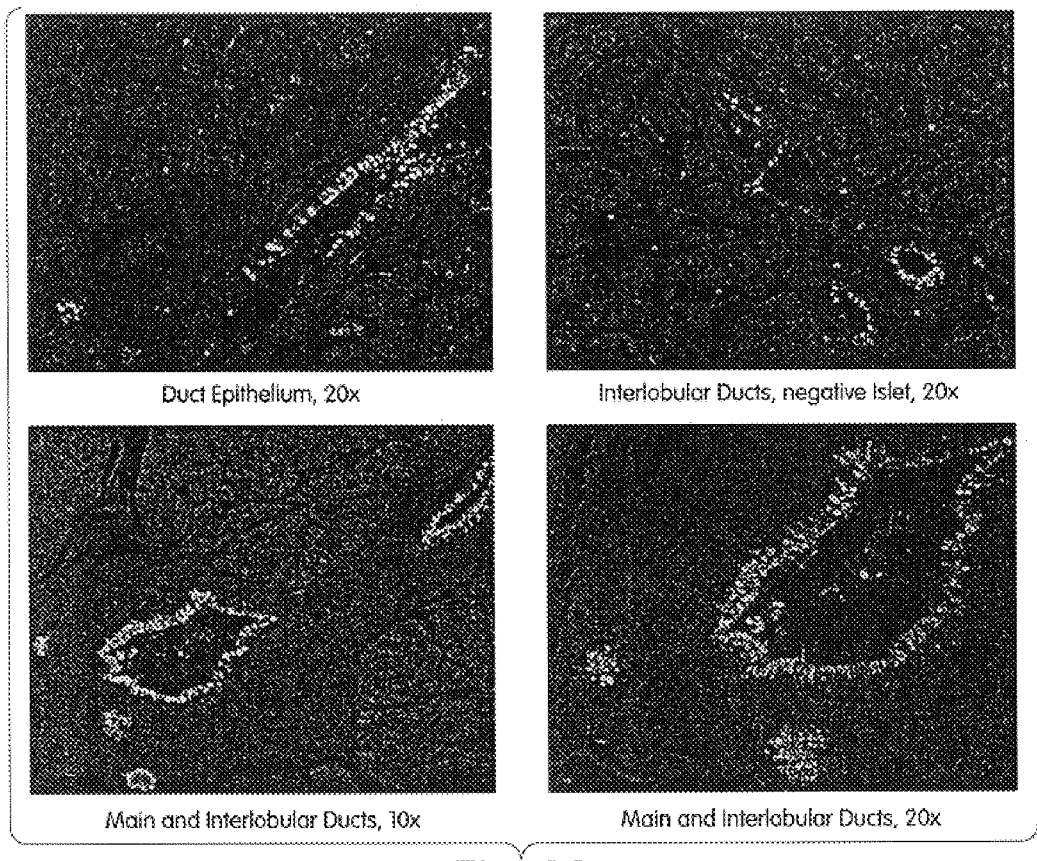
Figure 39:
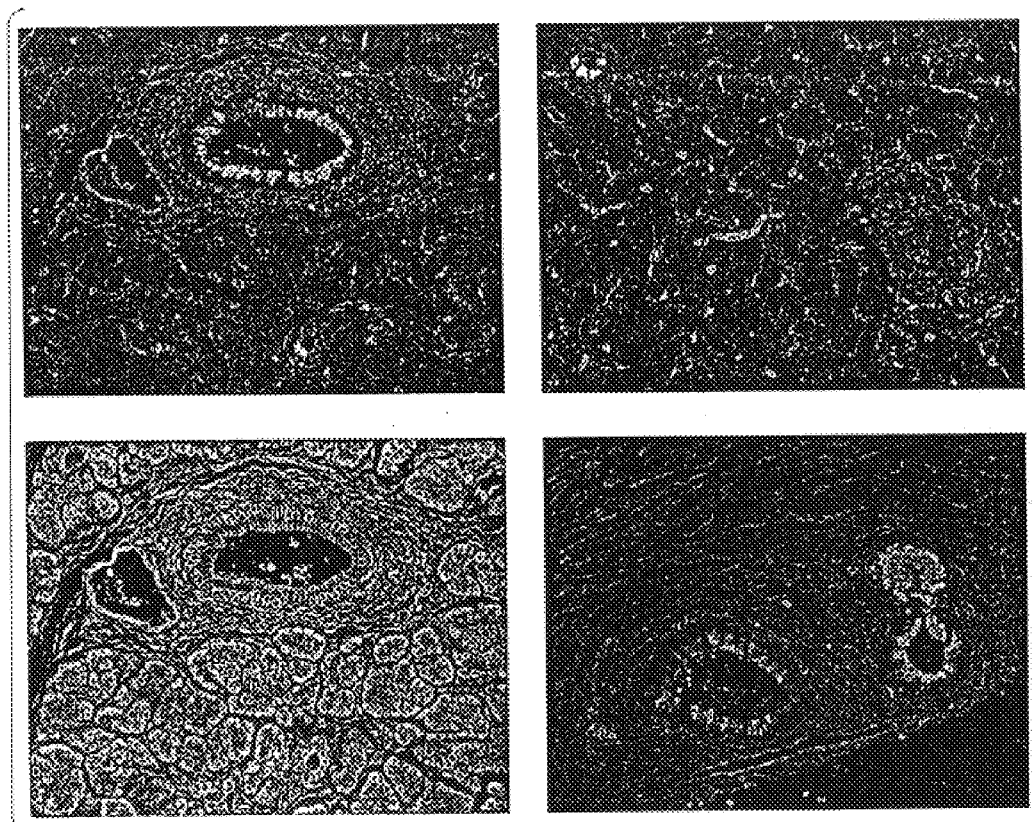

FIG. 27 shows autoradiographs profiling gene expression in the so-called floating progenitor cells described in the examples above; and FIG. 28 illustate the quantatitve analysis of the autoradiagraphs of FIG. 27. Using the subject method, we have demonstrated that our pancreatic progenitor cells are $PNA^+$ and $PDX1^-$ when they are first isolated. As the cells differentiate to insulin-secreting cells ($insulin^+$), they become $PNA^+$, $PDX1^+$. The earlier progenitor cells, in addition to being $PNA^+$, $PDX1^-$, $insulin^-$, $PYY^-$, $glucagon^-$ and $cytokeratin^+$.

FIG. 29 shows the relative levels of expression of certain genes between adult islets and during pancreatis development.

EXAMPLE 5

Implanted Cells from a Pancreatic Duct-derived Culture Transiently Rescues the Diabetic State SCID/icrl mice were obtained from Taconic. Average weight per mouse was 25 g. Streptozotocin (STZ) was purchased from Sigma and made into a 30 mg/ml solution in 20 mM sodium citrate buffer, pH 4.5. Each animal received STZ at a dose of 200 mg/kg and fed ad libitum prior to fasting blood glucose (food removed the previous evening) on the morning of the $3^{rd}$ day post injection. Diabetic animals were those found to have blood glucose in excess of 200 mg/dl with the average centering around 300 mg/dl. Insulin pellets (Innovative Research of America) that released 1.2 U of porcine insulin per day for 7 days were then implanted via trochar subcutaneously over the scapula. After monitoring for recovery from the diabetic state (blood glucose=100 mg/dl), either cells derived from pancreatic duct culture, or isolated adult pancreatic islets were then implanted under the renal capsule using standard surgical procedures. Either 500,000 or $10^6$ cells (non-adherent cell (NAC) fraction of duct culture) were implanted into mice. All operated mice survived in placebo, islet, and insulin pellet only groups. 6/7 cell implanted mice died 48–72 hours post implantation. For all groups fasting blood glucose was measured at standard intervals by tail bleed.

Figure 40:
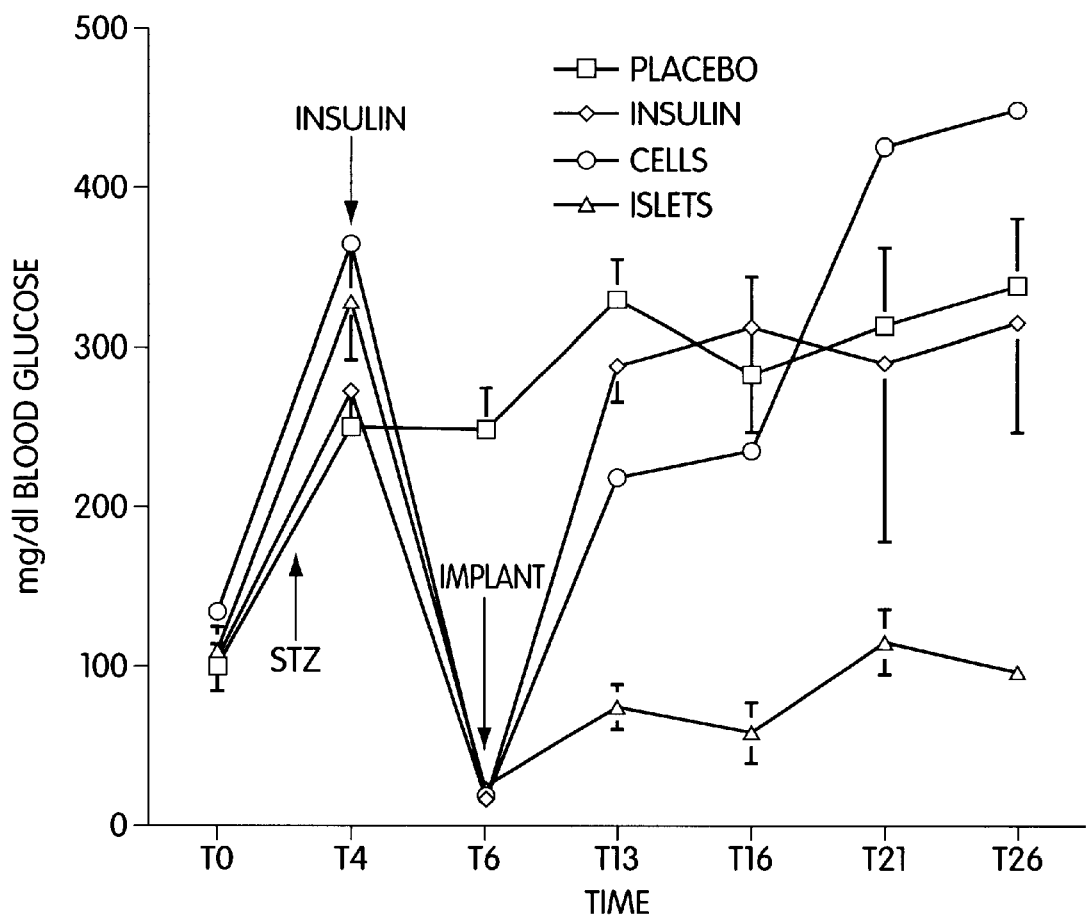

As shown in FIG. 40, a heterogeneous population containing functional beta cells derived from the non-adherent portion of a differentiated pancreatic duct monolayer was implanted into streptozotocin (STZ)-treated diabetic mice. SCID mice injected with STZ became diabetic within 48 hours. Insulin containing pellets were then implanted subcutaneously to stabilize the blood glucose and create a more stable environment for cell implantation. The insulin pellet was designed to expire 7 days post-implantation at T=11 days (T11). Within 48 hours of pellet implant the fasting blood glucose of these animals were reduced from a range of 280–380 mg/dl blood glucose to less than 50 mg/dl. In test groups either cells or adult islets as positive control were then implanted under the renal capsule. One week later (T13) fasting blood glucose was measured and again at days 16, 21, and 28. Black squares represent placebo group (n=5 mice) and as expected, in the absence of insulin, the blood glucose slowly climbed over time to well over 300 mg/dl. Animals (n=5) implanted with insulin pellets only and no cell implants also performed as expected, with a transient rescue followed by diabetic rebound after the insulin release tablet had expired (red diamonds). Animals receiving islets (blue triangles, n=5, 400 islets per animal) showed perfect long term rescue with fasting blood glucose being maintained at approximately 100 mg/dl. The single surviving animal receiving duct-derived cells (green circles, n=1 of 7) showed a transient rescue of the diabetic state. The single animal demonstrated a 4–5 day lowering of >150 mg/dl blood glucose before rebounding to pre-implant blood glucose levels.

References for Examples

King, H., Aubert, R. E., Herman, W. H. Global burden of diabetes, 1995–2025: prevalence, numerical estimates, and projections. Diabetes Care 1998;21:1414–1431.

1998 Disease Management Handbook, Diabetes Statistics; prevalence of diabetes in the United States. National Diabetes Information Clearinghouse. NIH Publication No. 96–3926, October 1995.

Korbutt, G. S., Warlock, G. L. & Rajotte, R. V. Islet transplantation. Adv. Exp. Med. Biol. 426, 397–410 (1997).

Secchi, A., Di Carlo, V. & Pozza, G. Pancreas and islet transplantation: current progresses, problems and perspectives. Horm. Metab. Res. 29, 1–8 (1997).

Sutherland, D. E., Pancreas and islet cell transplantation: now and then. Transplant Proc. 28, 2131–2133 (1996).

Weir, G. C. & Bonner-Weir, S. Scientific and political impediments to successful islet transplantation. Diabetes 1997;46:1247–1256.

Bensley, R. R. Studies on the pancreas of the guinea pig. Amer. J. Anat. 12, 297–388 (1911).

Shaw, J. W. & Latimer, E. O. Regeneration of pancreatic tissue from the transplanted pancreatic duct in the dog. Am. J. Physiol. 76, 49–53 (1926).

Warren, S. & Root, H. F. The pathology of diabetes, with special reference to pancreatic regeneration. Am. J. Pathol. 1, 415–429 (1925).

Bonner-Weir, S., Baxtyer, L. A., Schuppin G. T. & Smith, F. E. A second pathway for regeneration of adult exocrine and endocrine pancreas. A possible recapitulation of embryonic development. Diabetes. 42, 1715–1720, 1993.

Gu, D. & Sarvetnick, N. Epithelial cell proliferation and islet neogenesis in IFN-g transgenic mice. Development 118, 33–46, 1993.

Fernandes, A., et al. Differentiation of new insulin-producing cells is induced by injury in adult pancreatic islets. Endocrinology 1997;138:1750–1762.

Githens, S. The pancreatic duct cell: proliferative capabilities, specific characteristics, metaplasia, isolation, and culture. J. Ped. Gastroenterol. and Nutr. 1988;7:486–506.

Lampeter, E. F. et al. Regeneration of beta-cells in response to islet inflammation. Exp. Clin. Endocrinol. Diabetes 103 (suppl 2), 74–78, 1995.

Wang, R. N., Kloppel, G. & Bouwens, L. Duct- to islet-cell differentiation and islet growth in the pancreas of duct-ligated adult rats. Diabetologia 38, 1405–1411, 1995.

Rosenberg L. In vivo cell transformation: neogenesis of beta cells from pancreatic ductal cells. Cell Transplant. 4, 371–383, 1995.

Melmed, R. N. Intermediate cells of the pancreas. Gastroenterology 76, 196–201, 1979.

Cossel, L. Intermediate cells in the adult human pancreas. Virchows Arch [Cell Pathol.] 47, 313–328, 1984.

Gu, D., Lee, M.-S., Krahl, T. & Sarvetnick, N. Transitional cells in the regenerating pancreas. Development 120, 1873–1881, 1994.

Ohlsson, H., Karlsson, K., Edlund, T. IPF1, a homeodomain-containing transactivator of the insulin gene. EMBO J. 12: 4251–4259 (1993).

Offield, M. F. et al. PDX-1 is required for pancreatic outgrowth and differentiation of the rostral duodenum. Development 122: 983–995 (1996).

Ahlgren, U., Jonsson, J., Edlund, H. Arrested development of the pancreas in IPF1/PDX1 deficient mice reveals that the pancreatic mesenchyme develops independently of the pancreatic epithelium. Development 1996;122:1409–1416.

Madsen, O. D. et al. Pancreatic development and maturation of the islet B cell. Eur. J. Biochem. 1996;242:435–445.

Edlund, H. Transcribing pancreas. Diabetes 1998;47;1817–1823.

Upchurch, B. H., Aponte, G. W., Leiter, A. B. Expression of peptide YY in all four islet cell types in the developing mouse pancreas suggests a common peptide YY-producing progenitor. Development 1994;120:245–252.

Githens, S. et al. Biochemical and histochemical characterization of cultured rat and hamster pancreatic ducts. Pancreas 2, 427–438, 1987.

Githens, S., Schexnayder, J. A., Desai, K. & Patke, C. L. Rat pancreatic interlobular duct epithelium: isolation and culture in collagen gel. In Vitro Cell Dev. Biol. 25, 679–688, 1989.

Goloslow, N. & Grobstein, C. Epitheliomesenchymal interactions in pancreatic morphogenesis. Dev. Biol. 4, 242–255, 1962.

Wessels, N. K. & Cohen, J. H. Early pancreas morphogenesis: morphogenesis, tissue interactions and mass effects. Dev. Biol. 15, 237–270, 1967.

Apelqvist, A., Ahlgren, U., Edlund, H. Sonic hedgehog directs specialised mesoderm differentiation in the intestine and pancreas. Curr. Biol. 1997;7:801–804.

Githens, S. & Whelan, J. F. Isolation and culture of hamster pancreatic ducts. J. Tissue Cult. Methods 1983;8:97–102.

Sjoholm, A. diabetes mellitus and impaired pancreatic beta-cell proliferation. J. Intern. Med. 1996; 239: 211–220.

Nielsen, J H., Svensson, C., Galsgaard, E D., Moldrup, A., Billestrup, N. Beta cell proliferation and growth factors. J. Mol. Med. 1999; 77: 62–66.

Otonkoski, T. et al. Hepatocyte growth factor/scatter factor has insulinotropic activity in human fetal pancreatic cells. Diabetes 1994;43:947–953.

Sanvito, F. et al. TGF-beta 1 influences the relative development of the exocrine and endocrine pancreas in vitro. Development 1994;120:3451–3462.

Brady, G., et al. Analysis of gene expression in a complex differentiation hierarchy by global amplification of cDNA from single cells. Current Biology 5: 909–922, 1995.

Dulac, C., & Axel, R. A novel family of genes encoding putative pheromone receptors in mammals. Cell 83: 195–206, 1995.

Wang, J.-L. & McDaniel, M. L. Secretagogue-induced oscillations of cytoplasmic Ca2+ in single_ and a-cells obtained from pancreatic islets by fluorescence-acfivated cell sorting. Biochem. Biophys. Res. Comm. 166: 813–818, 1990.

Kalkhoff, R. K. & Siegesmund, K. A. Fluctuations of calcium, phosphorus, sodium, potassium, and chlorine in single alpha and beta cells during glucose perifusion of rat islets. J. Clin. Invest. 68: 517–524, 1981.

Asada, N., Shibuya, I., Iwanaga, T., Niwa, K., Kanno, T. Identification of a- and _-cells in intact isolated islets of langerhans by their characteristic cytoplasmic Ca2+ concentration dynamics and immunocytochemical staining. Diabetes 1998;37:751–757.

Schuitt, F. Factors determining the glucose sensitivity and glucose responsiveness of pancreatic beta cells. Horm. Res. 1996;46:99–106.

Halban, P. A. et al. The possible importance of contact between pancreatic islet cells for the control of insulin release. Endocrinology 1982; 111:86–94.

Bosco, D., Orci, L., Meda, P. Homologous but not heterologous contact increases the insulin secretion of individual pancreatic B-cells. Exp. Cell Res. 1989; 184:72–80.

Moitoso de Vargas, L., Sobolewski, J., Siegel, R., Moss, L. R. Individual_cells within the intact islet differentially respond to glucose. J. Biol. Chem. 1997; 272: 26573–26577.

Niki A., Niki, H., Miwa, I., Okuda, J. Insulin secretion by anomers of glucose. Science 1974;186:150–151.

Niki, A., Niki, H., Hashioka, T. Effects of specific inhibitors of sweet taste response on glucose-induced insulin release. Biomed. Res. 1993;14:13–18.

Malaisse, W. J., Sener, A., Herchuelz, A., Hutton, J. C. Insulin release: The fuel hypothesis. Metabolism 1979;28:373–386.

Thomas, P., Ye, Y., Lightner, E. Mutation of the pancreatic islet inward rectifier Kir6.2 also leads to familial persistent hyperinsulinemic hypoglycemia of infancy. Hum. Mol. Genet. 1996;5:1809–1812.

Henquin J. C. & Meissner H. P. Opposite effects of tolbutamide and diazoxide on 86Rb+ fluxes and membrane potential in pancreatic_-cells. Biochem. Pharmacol. 1982;31:1407–1415.

Trube, G., Rorsman, P., Shosaku, O. Opposite effects of tolbutamide and diazoxide on the ATP-dependent K+ channel in mouse pancreatic_-cells. Pfluegers Arch. Eur. J. Physiol. 1986;407:493–499.

Wollheim, C. B. & Sharp, G. W. G. Regulation of insulin release by calcium. Physiol. Rev. 1981;61:914–973.

Sato, Y., Anello, M., Henquin, J. C. Glucose regulation of insulin secretion independent of the opening or closure of adenosine triphosphate-sensitive K+ channels in beta cells. Endocrinology 1999; 140: 2252–2257.

Melander, A. Pharmacological intervention: the antidiabetic approach. Eur. J. clin. Invest. 1998; Suppl 2: 23–26.

Korsgren, O., Andersson, A., Sandler, S. In vitro screening of putative compounds inducing fetal porcine pancreatic beta-cell differentiation: Implications for cell transplantation in insulin-dependent diabetes mellitus. Ups. J. Med. Sci. 1993;98:39–52.

Brons, G., Newby, A. C. Hales, C. N. Glucocorticoids stimulate the division of rat pancreatic islet tumour cells in tissue culture. Daibetologia 1984; 27:540–544.

Rall, L., Pictet, R., Githens, S., Rutter, W. J. Glucocorticoids modulate the in vitro development of the embryonic rat pancreas. J. Cell Biol. 1977;75(2 Pt 1):398–409.

Van Nest, G., Raman, R. K., Rutter, W. J. Effects of dexamethasone and 5-bromodeoxyuridine on protein synthesis and secretion during in vitro pancreatic development. Dev. Biol. 1983;98:295–303.

Lambillote C., Gilon, P., Henquin, J. C. Direct glucocorticoid inhibition of insulin secretion. An in vitro study of dexamethasone effects in mouse islets. J. Clin. Invest. 1997;99:414–423.

Gladhaug I. P., Refsnes, M., Christoffersen, T. Regulation of surface expression of high-affinity receptors for epidermal growth factor (EGF) in hepatocytes by hormones, differentiating agents, and phorbol ester. Dig. Dis. Sci. 1992;37:233–239.

Miettinen, P. J. Epidermal growth factor receptor in mice and men—any applications to clinical practice? Ann. Med. 1997;29:531–534.

Heimann T. G., Githens, S. Rat pancreatic duct epithelium cultured on a porous support coated with extracellular matrix. Pancreas 1991;6:514–521.

Rindler, M. J., Chuman, L. M., Shaffer, L., Saier, M. H. Jr. Retention of differentiated properties in an established dog kidney epithelial cell line (MDCK). J. Cell Biol. 1979;81:635–648.

Yuan, S. et al. Transdifferentiation of human islets to pancreatic ductal cells in collagen matrix culture. Differentiation 1996;61:67–75.

Otonkoski, T., Beattie, G. M., Mally, M. I., Ricordi, C., Hayek, A. Nicotinamide is a potent inducer of endocrine differentiation in cultured human fetal pancreatic cells. J. Clin. Invest. 92: 1459–1466, (1993).

Huotari, M. A., Plagi, J., Otonkoski, T. Growth factor-mediated proliferation and differentiation of insulin-producing INS-1 and RINm5F cells: identification of beta-cellulin as a novel beta-cell mitogen. Endocrinology 139: 1494–1499, (1998).

Sorenson, R. L. & Brelje, T. C. Adaptation of islets of Langerhans to pregnancy: beta-cell growth, enhanced insulin secretion and the role of lactogenic hormones. Horm. Metab. Res. 29: 301–307, (1997).

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

TABLE 1

Immunostaining in Duct Cultures
Marker expression in isolated ducts and Insulin in duct cultures.

Marker Expression in Pancreatic Ducts at the Start of Culture

|  | Insulin | PDX-1 | PYY | Amylase |
|---|---|---|---|---|
| % Positive Ducts | 7.8% | 5.3% | 8.3%% | 14.5% |
| % Positive Cells | 0.01% | 0.01% | 0.015% | 0.02% |

Immunostaining for Insulin in Duct Cultures

|  | TotalCells Prep | Total Ins Positive Cells/Prep | % Insulin-Positive |
|---|---|---|---|
| T = 0, Primary Ducts T = 7 days | 800K | 80 | 0.01% |
| Control Monolayer Activated (+ DCE) | 2,000K | 400 (5x ↑) | 0.02% |
| Monolayer | 2,400K | 1000 (12.5x ↑) | 0.04% |
| NACs | 100K | 40,000 (500x ↑) | 40% |

TABLE 1-continued

Immunostaining in Duct Cultures
Marker expression in isolated ducts and Insulin in duct cultures.

The average cell number per duct fragment was 3450 ± 1860 (n = 10), comprising a single layer of epithelial cells surrounded by mesenchymal/stromal cells.
Positive immunostaining on whole isolated ducts (n = 60–90) was as follows:
Insulin 7/90 ducts, 32 positive cells;
PDX-1 4/75 ducts, 15 positive cells;
PYY 5/60 ducts, 31 cells;
Amylase 10/69 ducts, 49 cells.
n = 2 isolations for PDX-1, PYY, amylase;
n = 4 isolations for insulin.
NAC yield generally ranged from 80,000 to 130,000 cells/prep; maximum seen was 160,000 although theoretical maximum based on an observed cell density is estimated to be 300,000 cells/prep (10,000 NACs/cm$^2$).

TABLE 2

Immunostaining for PDX-1, PYY and Amylase in Duct Cultures

|  | Total PDX-1 Positive Cells/Prep | % PDX-1 Positive |
|---|---|---|
| T = 0, Primary Ducts T = 7 days | 80 | 0.01% |
| Control Monolayer Activated (+ DCE) | 480 (6x ↑) | 0.02% |
| Monolayer | 1200 (15x ↑) | 0.05% |

|  | Total PYY Positive Cells/Prep | % PYY Positive |
|---|---|---|
| T = 0, Primary Ducts T = 7 days | 120 | 0.015% |
| Control Monolayer Activated (+DCE) | 60 (2x ↓) | 0.003% |
| Monolayer | 100 (approx. no change) | 0.004% |

|  | Total Amylase Positive Cells/Prep | % Amylase Positive |
|---|---|---|
| T = 0, Primary Ducts T = 7 days | 160 | 0.02% |
| Control Monolayer Activated (+ DCE) | * (>10x ↓) | ** |
| Monolayer | ND | ND |

96–100% of Insulin-positive cells in culture were also PDX-1-positive.
In addition, PDX-1-positive, insulin-negative cells appear in all states of culture; however, in DCE-activated monolayers, the number of these cells is increased (20–50% more cells) and there are more cytoplasmic PDX-1 cells.
There is little or no apparent change in PYY in the monolayer; however, PYY appears to be present in emerging NACs.
*Only two out of ten preparations contained any Amylase-positive cells at all.
**% Amylase-positive is on the order of 0.001% for the positive preps.
ND, not detected.

What is claimed is:

1. A method of isolating progenitor cells comprising:
   i) obtaining pancreatic ductal tissue substantially free of tissues other than the ductal epithelium and surrounding mesenchyme,
   ii) obtaining dissociated pancreatic ductal cells from the pancreatic ductal tissue;
   iii) culturing said pancreatic ductal cells in a suitable nutrient medium; and
   iv) isolating a population of progenitor cells from said culture.

2. A method of claim 1, wherein obtaining pancreatic ductal cells comprises obtaining pancreatic intralobular ductal epithelial cells.

3. A method of claim 1, wherein said pancreatic ductal cells are obtained by explant or by enzymatic digestion.

4. A method of claim 1, wherein culturing said pancreatic ductal cells comprises growing said cells to confluence.

5. A method of claim 1, wherein said progenitor cells are isolated by mechanical separation.

6. A method for preparing a composition comprising progenitor cells, comprising
   i) isolating pancreatic progenitor cells by the method of claim 1, and
   ii) combining the pancreatic progenitor cells with a pharmaceutically acceptable excipient.

7. The method of claim 1, wherein the pancreatic ducts are substantially free of islet tissue.

8. A method of claim 4, wherein isolating a population of progenitor cells comprises isolating non-adherent cells, and wherein the method further comprises treating the isolated cells with an agent.

9. The method of claim 6, which progenitor cells are mammalian.

10. The method of claim 6, which progenitor cells differentiate to pancreatic lineages.

11. The method of claim 6, which progenitor cells can be maintained in culture for at least about 7 days.

12. The method of claim 6, which progenitor cells are inducible to differentiate into pancreatic islet cells.

13. The method of claim 6, further comprising combining the cells and/or the excipient with an agent that induces differentiation of the progenitor cells.

14. A method of claim 8, wherein said agent induces differentiation and is selected from forskolin, dibutyryl cAMP, Na-butyrate, dexametbasone, and cholera toxin.

15. A method of claim 8, wherein said agent is a growth factor.

16. The method of claim 9, wherein the progenitor cells are transgenic mammalian cells.

17. The method of claim 9, wherein the progenitor cells are primate cells.

18. The method of claim 9, wherein the progenitor cells are miniature swine cells.

19. The method of claim 10, which progenitor cells differentiate to β islet cells, α cells, δ islet cells, φ islet cells, or exocrine cells.

20. The method of claim 12, which islet cells are pancreatic β islet cells.

21. The method of claim 12, which islet cells are pancreatic α islet cells.

22. The method of claim 12, which islet cells are pancreatic δ islet cells.

23. The method of claim 12, which islet cells are pancreatic φ islet cells.

24. The method of claim 13, wherein said agent is selected from forskolin, dibutyryl cAMP, Na-butyrate, dexamethasone, and cholera toxin.

25. A method of claim 15, wherein said growth factor is selected from insulinlike growth factor (IGF), transforming growth factor (TGF), fibroblast growth factor (EGF), epidermal growth factor (EGF), hepatocyte growth factor (HGP), hedgehog, and vascular endothelial growth factor (VEGF).

26. A method of claim 15, wherein said growth factor is selected from the transforming growth factor-β (TGFβ) superfamily, bone morphogenic protein-2 (BMP2) and bone morphogenic protein-7 (BMP7).

27. The method of claim 17, wherein the progenitor cells are human cells.

28. A method for stimulating the ex vivo proliferation of mammalian pancreatic β-islet cells, comprising the steps of:

(a) preparing a primary culture of mammalian pancreatic cells; and (b) contacting said primary culture cells with a cAMP agonist in an amount sufficient to induce the primary culture to differentiate to β-islet cells.

29. The method of claim 28, wherein the mammalian pancreatic cells are human pancreatic cells.

30. The method of claim 28, wherein inducing the primary culture to differentiate comprises inducing an increase in average cellular insulin production.

31. The method of claim 28, further comprising growing said primary culture cells in a monolayer on an extracellular matrix in the presence of a growth factor.

32. The method of claim 28, further comprising contacting said primary culture cells or β-islet cells with an agent that upregulates the insulin gene.

33. A method for preparing a composition comprising β-islet cells, comprising i) isolating β-islet cells by the method of claim 28, and ii) combining the β-islet cells with a pharmaceutically acceptable excipient.

34. The method of claim 32, wherein the agent is a poly (ADP-ribose) synthetase inhibitor.

35. The method of claim 34, wherein the poly(ADP-ribose)synthetase inhibitor is nicotinamide or a benzamide.

36. A method for stimulating the ex vivo proliferation of human adult pancreatic beta islet-cells, comprising the steps of:

(a) preparing a monolayer culture of primary human adult pancreatic cells; and (b) culturing said cells with a cAMP agonist in an amount sufficient to induce the primary culture to produce insulin-producing cells.

37. A method for preparing a composition comprising insulin-producing cells, comprising i) producing insulin-producing cells by the method of claim 36, and ii) combining the insulin-producing cells with a pharmaceutically acceptable excipient.

38. A method of producing human adult pancreatic islet cells in clinically useful quantities, comprising:

(a) seeding a bioreactor with a human pancreatic cell culture;

(b) perfusing said bioreactor with a complete growth medium supplemented with an amount of a cAMP agonist sufficient to induce cells in the bioreactor to proliferate and differentiate into insulin-secreting cells; and (c) harvesting insulin-secreting cells from said bioreactor.

39. A method for preparing a composition comprising insulin-secreting cells, comprising i) producing insulin-secreting cells by the method of claim 38, and ii) combining the insulin-secreting cells with a pharmaceutically acceptable excipient.

* * * * *

UNITED STATES PATENT AND TRADEMARK OFFICE
CERTIFICATE OF CORRECTION

PATENT NO. : 6,326,201 B1
DATED : December 4, 2001
INVENTOR(S) : Brenda Fung, Kevin Pang and David Kagan It is certified that error appears in the above-identified patent and that said Letters Patent is hereby corrected as shown below:

Column 46,
Line 40, replace "dexametbasone" with -- dexamethasone --.
Line 64, after "fibroblast growth factor" replace "(EGF)" with -- (FGF) --.

Signed and Sealed this

Seventh Day of May, 2002

Attest:

JAMES E. ROGAN
Attesting Officer — Director of the United States Patent and Trademark Office

SEQUENCE LISTING

<160> NUMBER OF SEQ ID NOS: 9

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: primer

<400> SEQUENCE: 1
atgtcgtcca ggccgctctg gacaaaatat gaattctttt tttttttttt tttttttttt    60

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 2
cacaactgga gctgggtgga g                                               21

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 3
caaaggcttt attcattgca gagg                                            24

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 4
gaccgcaggc tgagggtgag                                                 20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 5
cagaggtctg ccagcatctc g                                               21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 6
tcccagaaga agtcgccatt g                                               21

<210> SEQ ID NO 7
<211> LENGTH: 22

```
<212> TYPE: DNA
<213> ORGANISM: Artificial Sequence
<220> FEATURE:
<223> OTHER INFORMATION: Description of Artificial Sequence: primer

<400> SEQUENCE: 7
ttcattccgc agagatgttg tg                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 8
aagtccctca ccctcccaaa ag                                              22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 9
aacacctcaa accactccca gg                                              22
```